US011479759B2

(12) United States Patent
Flyckt et al.

(10) Patent No.: US 11,479,759 B2
(45) Date of Patent: Oct. 25, 2022

(54) MODIFIED SEED OIL CONTENT BY GENE EDITING

(71) Applicant: PIONEER HI-BRED INTERNATIONAL, INC., Johnston, IA (US)

(72) Inventors: Kayla S Flyckt, Ankeny, IA (US); Kristin Haug Collet, Des Moines, IA (US); Zhan-Bin Liu, Clive, IA (US); Keith R Roesler, Urbandale, IA (US); Bo Shen, Johnston, IA (US); Laura L Wayne, Des Moines, IA (US)

(73) Assignee: PIONEER HI-BRED INTERNATIONAL, INC.

( * ) Notice: Subject to any disclaimer, the term of this patent is extended or adjusted under 35 U.S.C. 154(b) by 0 days.

(21) Appl. No.: 17/057,056

(22) PCT Filed: May 30, 2019

(86) PCT No.: PCT/US2019/034606
§ 371 (c)(1),
(2) Date: Nov. 19, 2020

(87) PCT Pub. No.: WO2019/232182
PCT Pub. Date: Dec. 5, 2019

(65) Prior Publication Data

US 2021/0207103 A1 Jul. 8, 2021

Related U.S. Application Data

(60) Provisional application No. 62/796,847, filed on Jan. 25, 2019, provisional application No. 62/679,116, filed on Jun. 1, 2018.

(51) Int. Cl.
*C12N 9/10* (2006.01)
*C12N 15/82* (2006.01)

(52) U.S. Cl.
CPC ....... *C12N 9/1029* (2013.01); *C12N 15/8213* (2013.01); *C12N 15/8247* (2013.01); *C12Y 203/0102* (2013.01)

(58) Field of Classification Search
None
See application file for complete search history.

(56) References Cited

U.S. PATENT DOCUMENTS

2009/0293152 A1 11/2009 Roesler et al.
2015/0275223 A1 10/2015 Roberts et al.
2016/0348124 A1* 12/2016 Roesler ............. C12N 15/8247

FOREIGN PATENT DOCUMENTS

WO 2009/143397 A2 11/2009

OTHER PUBLICATIONS

Luo, Applications of CRISPR/Cas9 technology for targeted mutagenesis, gene replacement and stacking of genes in higher plants, Plant Cell Reports, 2016 (Year: 2016).*
Caldo, Diacylglycerol Acyltransferase 1 Is Regulated by Its N-Terminal Domain in Response to Allosteric Effectors, Plant Physiology, Oct. 2017 (Year: 2016).*
Lung, Diacylglycerol Acyltransferase: A Key Mediator of Plant Triacylglycerol Synthesis, Lipids, vol. 41, No. 12, 2006, pp. 1073 1088. (Year: 2006).*
Lam, H. M.; et al.: Diacylglycerol O-acyltransferase 1 [Glycine soja]. Genbank Entry [online], Dec. 17, 2014 (Dec. 17, 2014), [Retrieved on Aug. 26, 2019], Retrieved from the Internet: <URL: https://www.ncbi.nlm.nih.gov/protein/KHN06629.1>: p. 1.
Roesler, K.; et al.: "An Improved Variant of Soybean Type 1 Diacylglycerol Acyltransferase Increases the Oil Content and Decreases the Soluble Carbohydrate Content of Soybeans", Plant Physiology, Jun. 2016, Epub Apr. 19, 2016 (Apr. 19, 2016), vol. 171, No. 2, pp. 878-893.
International Search Report and Written Opinion for International Application No. PCT/US19/34606, dated Sep. 24, 2019.

* cited by examiner

*Primary Examiner* — Matthew R Keogh
*Assistant Examiner* — Brian James Sullivan

(57) ABSTRACT

Provided are compositions comprising polynucleotides encoding modified diacylglycerol acyltransferase-1 (DGAT1) polypeptides having improved properties, such as increased enzymatic activity and/or increased stability. Plants, plant cells, seed, grain and comprising the polynucleotides are provided which have one or more of increased fatty acid or protein content. Methods of generating the polynucleotides in plant cells include transformation and genetic modification. Methods of employing the polynucleotides in plants, methods for increasing DGAT1 activity in a plant, and methods for increasing fatty acid content or protein content in a plant are provided.

20 Claims, 13 Drawing Sheets

Figure 1:
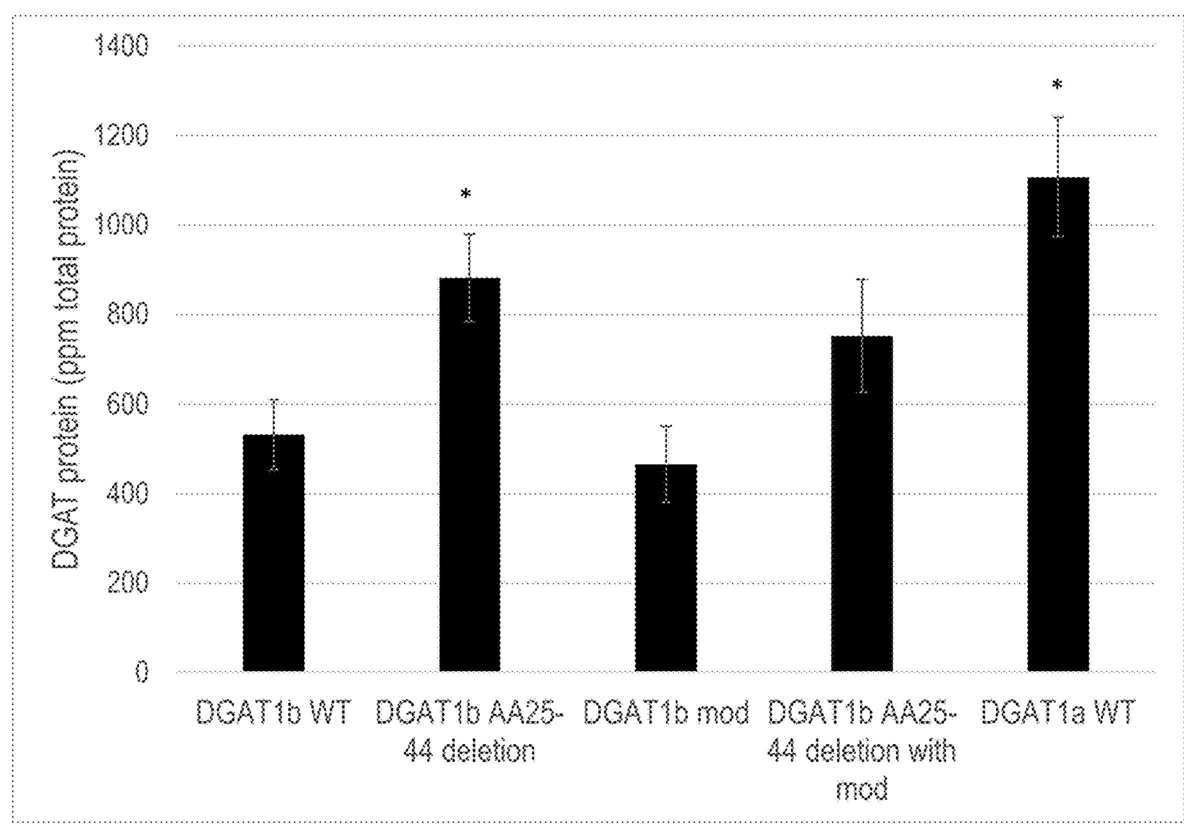

Specification includes a Sequence Listing.

```
                       1                                                50
 GmDGAT1A      (1)  --------------MAISDEPE--------TVATALNHSSLRRRP-----
 GmDGAT1B      (1)  --------------MAISDEPE--------SVATALNHSSLRRRPSA--T
 GmGDAT1c      (1)  --------------MAISDVPAAAG-----TTATTTSDSDLRQPSLRRRS
 BnDGAT1a      (1)  --------------MAILDSGG------VAVPPTENGVADLDRLHRRK--
 EgDGAT1-1     (1)  --------------MAVSKNPE-----TLAPDQEPSKESDLRRRPASSPS
 HvDGAT1       (1)  -------------------------------------------MAPPPSV
 TaDGAT1       (1)  -MSKGNPDPPPPRQLPPFPRRAAHRNPKPRPEPS-GTSPPVPPMAPPPSV
 ZmDGAT1-2     (1)  -------------------------------------------MAPPPSM
 OsDGAT1       (1)  MVGSDGDGDGGGGEAHAPAAPAHHHRRPPRPRGGSGAIVEGFAAALRRRI
 SbDGAT1b      (1)  ----------MADTDDAPPAPAVHRR-PPRPARG-AAAAQGFAAKLRRRL
 HaDGAT1       (1)  ----MALLDTSDIGDSTAIRGEIRRRRSVKPDAG-FGIGDGLYDSSSSSR
 GhDGAT1       (1)  --------------MAMFESPEISGSSTATVIGTSRSESDLNHFAPRR-R
 Substitution       ---------------------------------------------*----

                       51                                              100
 GmDGAT1A     (24)  TAAGLFNSP-------ETTTDSSGDDLAKDSG-SDDSISSDAANSQPQQ-
 GmDGAT1B     (27)  STAGLFNSP-------ETTTDSSGDDLAKDSG-SDDSINSDDAAVNSQQQ
 GmGDAT1c     (32)  SAGVLFDAARDSGSDNSLTGKITDDDNIKDHKPNNHAASDDNVGAAANDA
 BnDGAT1a     (29)  SSS---DSSNG---LLSDTSPSDDVGAAAAERDRVDSAAEEEAQGTANLA
 EgDGAT1-1    (32)  STAASPAVPDSSSRTSSSITGSWTTALDGDSGAGAVRIGDPKDRIGEAND
 HvDGAT1       (8)  AAAHDCDDP---------SLRLRRADG---------GSSGVHGEARPQE-
 TaDGAT1      (49)  AAAHDRDDP---------SLRLRRAP----------AADGVHGEAEPQE-
 ZmDGAT1-2     (8)  PAASDRAGPGRDA-GDSSSLRLRRAPSADAGDLAGDSSGGLRENGEPQSP
 OsDGAT1      (51)  RSGAAAAARASFG-GDSGDEAASGEPSSSSSSSPSRRRGGDSNGAEASSA
 SbDGAT1b     (39)  SSGAAAAARASFA-ADSGDESGPGEPSS------SRRR---DNGGDASSA
 HaDGAT1      (46)  TNSSEEEGE---------SLTNGFDENER------IRAGDETQTTQENKQ
 GhDGAT1      (36)  AVNNAVDAG-----TRVVERNNSGNGETVDARDRMESANFSRENVNENP-
 Substitution       -------*------------------------------*-----------

                       101                                             150
 GmDGAT1A     (65)  -----KQDTDFSVLKFAYRPSVPAHRKVKESPLSSDTIFRQSHAGLFNLC
 GmDGAT1B     (69)  N---EKQDTDFSVLKFAYRPSVPAHRKVKESPLSSDTIFRQSHAGLFNLC
 GmGDAT1c     (82)  G---QEHRQPVADFKYAYRPSVPAHRRIKESPLSSDNIFRQSHAGLFNLC
 BnDGAT1a     (73)  GGDAETRESAGGDVRFTYRPSVPAHRRTRESPLSSDAIFKQSHAGLFNLC
 EgDGAT1-1    (82)  IGEKKKACSGEVPVGFVDRPSAPVHVRVVESPLSSDTIFQQSHAGLLNLC
 HvDGAT1      (39)  -------QPQRQHEMPCYRASAPAHRRVKESPLSSDAIFRQSHAGLLNLC
 TaDGAT1      (79)  -------QPQRQHEMPCYRASAPAHRRVKESPLSSDAIFRQSHAGLLNLC
 ZmDGAT1-2    (57)  TNP--PPQEQQQHEMLYYRASAPAHRRVKESPLSSDAIFRQSHAGLLNLC
 OsDGAT1     (100)  AGGGGGRGGGGDFSAFTFRAAAPVHRKAKESPLSSDAIFKQSHAGLFNLC
 SbDGAT1b     (79)  ADG--GRGGAGDFSAFTFRAAAPVHRKAKESPLSSDAIFKQSHAGLFNLC
 HaDGAT1      (81)  KTD--QRRDKTSLLQYAYRASSPAHRRIKESPLSSDAIFKQSHAGLFNLC
 GhDGAT1      (80)  ---------TNSDTRFTYRPSVPAHWRIKESPLSSDNIFQQSHAGLFNLC
 Substitution       --------------------------------------------------
```

FIG. 4A

```
                      151                                               200
 GmDGAT1A     (110)  IVVLVAVNSRLIIENLMKYGWLIKSGFWFSSKSLRDWPLFMCCLSLVVFP
 GmDGAT1B     (116)  IVVLVAVNSRLIIENLMKYGWLIKSGFWFSSKSLRDWPLFMCCLSLVVFP
 GmGDAT1c     (129)  IVVLVAVNSRLIIENLMKYGWLIKYGFWFSSKSLRDWPLFMCCLSLAIFP
 BnDGAT1a     (123)  VVVLVAVNSRLIIENLMKYGWLIRTDFWFSSTSLRDWPLFMCCLSLSVFP
EgDGAT1-1     (132)  VVVLIAVNSRLIIENLMKYGLLIGSGFFFSSRLLRDWPLLICSLTLPVFP
  HvDGAT1      (82)  IVVLIAVNSRLIIENLMKYGLLIRAGFWFSARSLGDWPLLMCCLTLPIFP
  TaDGAT1     (122)  IVVLIAVNSRLIIENLMKYGLLIRAGFWFSARSLGDWPLLMCCLTLPIFP
ZmDGAT1-2     (105)  IVVLIAVNSRLIIENLMKYGLLIRAGFWFSARSLGDWPLLMCCLTLPVFP
  OsDGAT1     (150)  IVVLVAVNSRLIIENLMKYGLLIRAGFWFNDKSLRDWPLLMCCLSLPAFP
 SbDGAT1b     (127)  IVVLVAVNSRLIIENLMKYGLLIRSGFWFNATSLRDWPLLMCCLSLPVFP
  HaDGAT1     (129)  IVVLVAVNGRLIIENLMKYGLLINSNFWFSSRSLRDWPLLMCCVSLLFFP
  GhDGAT1     (121)  VVVLVAVNSRLIIENLMKYGWLIRTGFWFSSRSLRDWPLFMCCLSLPIFP
Substitution         --------------------------------------------------

                      201                                               250
 GmDGAT1A     (160)  FAAFIVEKLAQQKCIPEPVVVVLHIIITSASLFYPVLVILRCDSAFLSGV
 GmDGAT1B     (166)  FAAFIVEKLAQRKCIPEPVVVVLHIIITSTSLFYPVLVILRCDSAFVSGV
 GmGDAT1c     (179)  LAAFVVERLAQQKCISEPVVVLLHLIISTVELCYPVLVILRCDSAFVSGV
 BnDGAT1a     (173)  LAAFTVEKMVLQKFISEPVAIILHVIITMTEVLYPVYVTLRCDSAFLSGV
EgDGAT1-1     (182)  LGSYMVEKLAYKKFISEPVVVSLHVILIIATIMYPVFVILRCDSPILSGI
  HvDGAT1     (132)  LAALMTEKWAQRKLIRDHVSILLHIIITATVLIYPVVVILKCESAVLSGF
  TaDGAT1     (172)  LAALMTEKWAQRKLIRDHVSILLHIIITTTVLIYPVVVILKCESAVLSGF
ZmDGAT1-2     (155)  LVALMAEKLITRKLIGEHVVILLHIIITTSAIVYPVVVTLKCDSAVLSGF
  OsDGAT1     (200)  LGAFAVEKLAFNNVITDAVATCLHIFLSTTEIVYPVLVILKCDSAVLSGF
 SbDGAT1b     (177)  LGAFAVEKLAFNNLITDAAATCFHIFLTTLEIVYPVLVILKCDSAVLSGF
  HaDGAT1     (179)  LAAYIVEKLAWKKRISDPVVITLHVIVTTTAILYPVFMILRVDSVVLSGV
  GhDGAT1     (171)  IAAFVVEKLLQQNQISERTLILLHILISTLAVLYPVVVILRCDSAFLSGI
Substitution         ---------------*----------------------------*-----

                      251                                               300
 GmDGAT1A     (210)  TLMLFACVVWLKLVSYAHTNYDMRALTKSVEKGEALPDTLNMDYPYNVSF
 GmDGAT1B     (216)  TLMLFSCVVWLKLVSYAHTNYDMRALTKLVEKGEALLDTLNMDYPYNVSF
 GmGDAT1c     (229)  TLMLLTCIVWLKLVSYAHTNYDMRALTVSNEKGETLPNTLIMEYPYTVTF
 BnDGAT1a     (223)  TLMLLTCIVWLKLVSYAHTSYDIRTLANSADKVDP-------EISYYVSL
EgDGAT1-1     (232)  NLMLFVSSICLKLVSYAHANYDLRSSSNSIDKGIHK--------SQGVSF
  HvDGAT1     (182)  VLMFIASITWLKLVSFAHTNHDIRVLSQSIEKGATHGSSIDEETIKGPTT
  TaDGAT1     (222)  VLMFIASITWLKLVSFAHTNYDIRVLSQSIEKGATHGSSIDEENIKGPTI
ZmDGAT1-2     (205)  VLMFLASIMWMKLVSYAHTNYDIRVLSKSTEKGAAYGNYVDPENMKDPTF
  OsDGAT1     (250)  LLIFIACIVWLKLVSFAHTNHDIRQLTMGGKKVDNELSTVDMDNLQPPTL
 SbDGAT1b     (227)  VLMFIACIVWLKLVSFAHTNHDIRKLITSGKKVDNELTVADIDNLQAPTL
  HaDGAT1     (229)  SLMLCACINWLKLTSFVHTSYDMRSLVNSTDKGETESESLDIELFYDADF
  GhDGAT1     (221)  ALMLFACIVWLKLVSYAHTNSDMRSVAKSTEKG-------SEGCMYNVSF
Substitution         *---------------------------*-------------*-----*-
```

FIG. 4B

```
                     301                                              350
  GmDGAT1A   (260)   KSLAYFLVAPTLCYQPSYPRTPYIRKGWLFRQLVKLIIFTGVMGFIIEQY
  GmDGAT1B   (266)   KSLAYFLVAPTLCYQPSYPRTPYIRKGWLFRQLVKLIIFTGVMGFIIEQY
  GmGDAT1c   (279)   RSLAYFMVAPTLCYQTSYPRTPSVRKGWVFRQLVKLIIFTGVMGFIIEQY
  BnDGAT1a   (266)   KSLAYFMVAPTLCYQPSYPRSPCIRKGWVARQLAKLVIFTGLMGFIIEQY
 EgDGAT1-1   (274)   KSLVYFIMAPTLCYQPSYPRTTCIRKGWVICQLVKLVIFTGVMGFIIEQY
   HvDGAT1   (232)   NSVVYFMLAPTLCYQPSYPRTAFVRKGWVAQQLIKCIVFTGLMGFIIEQY
   TaDGAT1   (272)   NSVVYFMLAPTLCYQPSYPRTAFTRKGWVTRQLIKCVVFTGLMGFIIEQY
 ZmDGAT1-2   (255)   KSLVYFMLAPTLCYQPTYPQTTCIRKGWVTQQLIKCVVFTGLMGFIIEQY
   OsDGAT1   (300)   GNLIYFMMAPTLCYQPSYPRTSCVRKGWLIRQIILYLIFTGLQGFIIEQY
  SbDGAT1b   (277)   GSLTYFMMAPTLCYQPSYPRTPYVRKGWLVRQVILYLIFTGLQGFIIEQY
   HaDGAT1   (279)   KSLVYFLLAPTLCYQLRYPRTAFIRKGWVLRQLIKLIIFTGLMGFIIEQY
   GhDGAT1   (264)   RSLAYFMAAPTLCYQTSYPRTASIRKNWVVRQFIKLIIFTGLMGFIIEQY
Substitution         --------------------------------------------------

                     351                                              400
  GmDGAT1A   (310)   INPIVQNSQHPLKGNLLYAIERVLKLSVPNLYVWLCMFYCFFHLWLNILA
  GmDGAT1B   (316)   INPIVQNSQHPLKGNLLYATERVLKLSVPNLYVWLCMFYCFFHLWLNILA
  GmGDAT1c   (329)   MNPIVQNSTHPLKGNLLYAIERILKLSVPNVYVWLCMFYCFFHLWLNILA
  BnDGAT1a   (316)   INPIVRNSKHPLKGDLLYAIERVLKLSVPNLYVWLCMFYCFFHLWLNILA
 EgDGAT1-1   (324)   IDPIIKNSQHPLKGNVLNAMERVLKLSIPTLYVWLCVFYCTFHLWLNILA
   HvDGAT1   (282)   INPIVQNSKHPLKGNFLDAIERVLKLSVPTLYVWLCMFYCFFHLWLNILA
   TaDGAT1   (322)   INPIVQNSKHPLKGNFLDAIERVLKLSVPTLYVWLCMFYSFFHLWLNILA
 ZmDGAT1-2   (305)   INPIVKNSKHPLKGNFLNAIERVLKLSVPTLYVWLCMFYCFFHLWLNIVA
   OsDGAT1   (350)   INPIVVNSQHPLKGGLLNAVETVLKLSLPNVYLWLCMFYAFFHLWLSILA
  SbDGAT1b   (327)   INPIVVNSQHPLKGGLLNAVETVLKLSLPNVYLWLCMFYCLFHLWLNILA
   HaDGAT1   (329)   INPIVQNSQHPLNGDILYAIERVLKLSVPNLYVWLCMFYCFFHLWLNILA
   GhDGAT1   (314)   INPIVQNSQHPLKANFLYAIERILKLSVPNTYVWLCMFYSFFHLWLNILA
Substitution         ------------*--------------------------*--------*-

                     401                                              450
  GmDGAT1A   (360)   ELLRFGDREFYQDWWNAKTVEDYWRMWNMPVHKWMIRHLYFPCLRHGIPK
  GmDGAT1B   (366)   ELLRFGDREFYKDWWNAKTVEDYWRMWNMPVHKWMIRHLYFPCLRHGLPK
  GmGDAT1c   (379)   ELVRFGDREFYKDWWNAKTVEEYWRMWNMPVHKWMVRHIYFPCLRRGIPK
  BnDGAT1a   (366)   ELLCFGDREFYKDWWNAKSVGDYWRMWNMPVHKWMVRHVYFPCLRIKIPK
 EgDGAT1-1   (374)   ELLCFGDREFYKDWWNAKTIEEYWRMWNMPVHKWMLRHVYLPCIRNGIPK
   HvDGAT1   (332)   ELLRFGDREFYKDWWNARTVEEYWRMWNMPVHKWIVRHIYFPCIRNGLSK
   TaDGAT1   (372)   ELLRFGDREFYKDWWNAKTVEEYWRMWNMPVHKWIVRHIYFPCIRNGLSK
 ZmDGAT1-2   (355)   ELLCFGDREFYKDWWNAKTVEEYWRMWNMPVHKWIIRHIYFPCIRKGFSR
   OsDGAT1   (400)   EILRFGDREFYKDWWNAKTIDEYWRKWNMPVHKWVVRHIYFPCMRNGISK
  SbDGAT1b   (377)   EILRFGDREFYKDWWNAKTIDEYWRKWNMPVHKWMLRHIYFPCIRNGISK
   HaDGAT1   (379)   ELLRFGDREFYKDWWNAQTIEEYWRLWNMPVHKWIVRHLYFPCLRNGIPK
   GhDGAT1   (364)   ELLRFGDREFYKDWWNAKTVEEYWRMWNMPVHKWMVRHIYLPCLRNGIPK
Substitution         ---------------------*----------------------------
```

FIG. 4C

```
                      451                                                500
  GmDGAT1A   (410) AVALLIAFLVSALFHELCIAVPCHIFKLWAFGGIMFQVPLVFITNYLQNK
  GmDGAT1B   (416) AAALLIAFLVSALFHELCIAVPCHIFKLWAFGGIMFQVPLVLITNYLQNK
  GmGDAT1c   (429) GAASLIAFLVSAVFHELCIAVPCHMFKLWAFIGIMFQVPLVLITNYLQNK
  BnDGAT1a   (416) VPAIIIAFLVSAVFHELCIAVPCRLFNLWAFMGIMFQVPLVFITNFLQER
 EgDGAT1-1   (424) GVAMVISFFISAIFHELCIGIPCHIFKFWAFIGIMFQVPLVILTKYLQNK
    HvDGAT1  (382) GCAILISFLVSAVFHELCIAVPCHIFKLWAFSGIMFQIPLLFLTKYLQDK
    TaDGAT1  (422) GCAILIAFLVSAVFHELCIAVPCHIFKLWAFSGIMFQIPLLFLTKYLQEK
 ZmDGAT1-2   (405) GVAILISFLVSAVFHEICIAVPCHIFKFWAFSGIMFQIPLVFLTRYLHAT
    OsDGAT1  (450) EVAVLISFLVSAVLHEICVAVPCRILKFWAFLGIMLQIPLIVLTAYLKSK
  SbDGAT1b   (427) EVAAFIAFFVSAVFHELCVAVPCHILKFWAFLGIMLQIPLIILTSYLKNK
    HaDGAT1  (429) GAAILVAFFMSAVFHELCIAVPCHIFKFWAFIGIMFQVPLVLLTNYLQNK
    GhDGAT1  (414) GVAILIAFLVSAIFHELCIAVPCHLFKLWAFFGIMFQAPLVLITSYLQNK
 Substitution      -----------------------*--------------------------

                    501                                      541
 GmDGAT1A (460)FRNSMVGNMIFWFIFSILGQPMCVLLYYHDLMNRKGKLD--(SEQ ID NO: 4)
 GmDGAT1B (466)FRNSMVGNMIFWFIFSILGQPMCVLLYYHDLMNRKGKLD--(SEQ ID NO: 2)
 GmGDAT1c (479)YRNSMVGNMIFWFIFCILGQPMSVLLYYHDLMNRKGEVD--(SEQ ID NO: 6)
 BnDGAT1a (466)FG-SMVGNMIFGSASCIFGQPMCGLLYYHDLMNRKGSMS--(SEQ ID NO: 8)
 EgDGAT1-1(474)FKSAMVGNMIFWFFFSIYGQPMCVLLYYHDVMNRKVGTE--(SEQ ID NO: 24)
 HvDGAT1  (432)FKNTMAGNMIFWFFFSIVGQPMCVLLYYHDVMNRQAQTNG-(SEQ ID NO: 14)
 TaDGAT1  (472)FKNTMVGNMIFWFFFSIVGQPMCVLLYYHDVMNRQAQTNG-(SEQ ID NO: 20)
 ZmDGAT1-2(455)FKHVMVGNMIFWFFFSIVGQPMCVLLYYHDVMNRQAQASR-(SEQ ID NO: 22)
 OsDGAT1  (500)FRDTMVGNMIFWFFFCIYGQPMCLLLYYHDVMNRIEKAR--(SEQ ID NO: 16)
 SbDGAT1b (477)FNDTMVGNMIFWFFFCIYGQPMCVLLYYHDVMNRTEKTK--(SEQ ID NO: 18)
 HaDGAT1  (479)FQNSMVGNIIFWCFFSILGQPMCVLLYYHDVMNQKVNSK--(SEQ ID NO: 12)
 GhDGAT1  (464)FQSSMVGNMIFWFIFCILGQPTCVLLYYHDLMNRKGSAD--(SEQ ID NO: 10)
```

FIG. 4D

MODIFIED SEED OIL CONTENT BY GENE EDITING

CROSS-REFERENCE TO RELATED APPLICATIONS

This application is a national stage application of PCT/US19/34606 filed May 30, 2019 which claims the benefit of priority to U.S. Provisional Application Nos. 62/679,116 filed on Jun. 1, 2018 and 62/796,847 filed on Jan. 25, 2019, each of which is incorporated herein by reference in its entirety.

REFERENCE TO SEQUENCE LISTING SUBMITTED ELECTRONICALLY

The official copy of the sequence listing is submitted electronically via EFS-Web as an ASCII formatted sequence listing with a file named "7776WOPCT_SEQLIST_ST25.txt" created on May 30, 2019 and having a size of 113 kilobytes and is filed concurrently with the specification. The sequence listing contained in this ASCII formatted document is part of the specification and is herein incorporated by reference in its entirety.

BACKGROUND

Plant oils are a major product of oil seed crops such as soybean, sunflower and canola. Oils, such as soybean oil, produced in the US are extracted from seeds and have a major use in food products such as cooking oils, shortenings and margarines. The oils can be refined, bleached and deodorized (RBD) and may be hydrogenated to facilitate use in shortenings. Plant genetic engineering has facilitated the engineering of plants to have improved seed composition, such as improved oils and fatty acid content.

SUMMARY

Provided are modified polynucleotides encoding a diacylglycerol acyltransferase-1 (DGAT1) polypeptide having a deletion of at least 1 and less than 107 amino acids in the N-terminal region corresponding to the region at positions 1 to 107 of SEQ ID NO: 2. The DGAT1 polypeptide can have increased stability, increased activity or effect an increase in fatty acid or fatty acid and protein content when expressed in a plant cell. Also provided are modified polynucleotides comprising, either in combination with an N-terminal deletion or without a N-terminal deletion, at least one amino acid substitution selected from a substitution at the position corresponding to position 24, 34, 58, 181, 210, 216, 244, 258, 264, 328, 355, 364, 387, 440, 467, 473 or 479, or any combination thereof of SEQ ID NO:2. The modified polynucleotides may share at least about 40%, 45%, 50%, 55%, 60%, 65%, 70%, 75%, 80%, 85%, 90%, 955, 96%, 97%, 98% or 99% identity to the corresponding genomic sequences, such as SEQ ID NO: 29 or 30. The deletion can represent a sequence encoding a polypeptide of at least or at least about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 amino acids, and less than or less than about 107, 106, 105, 100, 95, 90, 85, 80, 75, 70, 65, 60, 55, 50, 45, 40, 35, 30, 25, 20, 15, 10, 9, 8, 7, 6, 5, 4, 3 or 2 amino acids. The deletion can occur in a sequence encoding a polypeptide corresponding to SEQ ID NO: 2 at positions corresponding to position 1 to position 108 of SEQ ID NO: 2. The modified polynucleotide may encode a polypeptide having at least 70%, 75%, 80%, 85%, 90%, or 95% identity to positions 108 to 504 of SEQ ID NO: 2. The deletion can include a deletion corresponding to the N-terminal region of the coding sequence or encoded polypeptide of at least or at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 49, 49, 50, 51, 52, 53, 55, 55, 56, 57, 58, 59, 60, 65, 70, 75, 80, 85, 90, 95, 100, 105, 110, 115, 120, 125, 130, 135, 140, 145, 150, 160, 170, 180, 190, 200, 210, 220, 230, 240, 250, 260, 265, 270, 280, 290, or 300 nucleotides and less than or less than about 321, 320, 310, 300, 290, 280, 270, 260, 250, 240, 230, 220, 210, 200, 190, 180, 170, 160, 150, 145, 140, 135, 130, 125, 120, 115, 110, 95, 90, 85, 80, 75, 70, 65, 60, 55, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, or 6 nucleotides, for example the deletion can occur in a location corresponding to from position 1 to position 321 of SEQ ID NO: 1.

The modified polynucleotides can encode polypeptides which comprise one or more or all three signature motifs such as APTLCYQ (SEQ ID NO: 38, corresponding to position 274-280 of SEQ ID NO: 2), FGDREFYXDWWNA (SEQ ID NO: 39; corresponding to position 370-382 of SEQ ID NO: 2) and LLYYHD (SEQ ID NO: 40; position 390-395 of SEQ ID NO: 2), where X is any amino acid, such as K or Q. Other amino acid motifs in the polypeptides disclosed herein and polynucleotides encoding them include, for example, GFIIEQYINPIVXNSXHPL (SEQ ID NO: 41; corresponding to position 309-327 of SEQ ID NO: 2) and ESPLSSDXIFXQSHAGLXNLCXVVLXAVNXR-LIIENLMKYGXLI (SEQ ID NO: 42; corresponding to position 95-138 of SEQ ID NO: 2), wherein X is any amino acid. The polypeptides may include at least 1, 2, 3, 4 or 5 amino acid motifs disclosed herein, and any combination thereof. Such polynucleotides may encode polypeptides having at least about 50%, 55%, 60%, 70%, 75%, 80%, 85%, 90%, or 95% identity to SEQ ID NO:2 and comprise one or more of the motifs disclosed herein.

Plant cells, seed cells, soybean cells and soybean plants and seeds containing the modified polynucleotides and polypeptides disclosed herein are provided. The cells, seeds and plants can show increased fatty acid content when compared to a cell, seed or plant comprising a comparable polynucleotide which lacks the modification. Modified polypeptides encoded by the polynucleotides are also provided.

The increase in fatty acid content in the cell or seed containing or expressing the modified polynucleotides or polypeptides disclosed herein can be an increase of at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45% or 50% relative to the fatty acid content of a cell or seed expressing the polypeptide without the modifications. The increase in fatty acid content in the cell or seed can be an increase of at least at least 0.5, 0.6, 0.7, 0.8, 0.9, 1, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.5, 6.0, 6.5, 7.0, 7.5, or 8.0 percentage points and less than about 10.0, 9.5, 9.0, 8.5, 8.0, 7.5, 7.0, 6.5, 6.0, 5.5, 5.0 or 4.5 percentage points by weight of the cell relative to control.

The increase in protein content in the cell or seed containing or expressing the modified polynucleotides or polypeptides disclosed herein can be an increase of at least 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.5%, 4.0%, 4.5% or 5.0% relative to the protein content of a cell or seed expressing the polypeptide without the modifications. The increase in protein content in the cell or seed can be an increase of at least at least 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9 or 2.0 percentage points and less than about 5.0, 4.5, 4.0, 3.5, 3.0, 2.5, 2.0, or 1.5 percentage points by weight of the cell relative to control.

In some embodiments, a modified polynucleotide encoding a polypeptide having at least 90% identity to SEQ ID NO:2 and at least 70% identity to SEQ ID NO:29 is provided which comprises one or more modifications selected from a non-serine at the position corresponding to position 24 of SEQ ID NO:2, a non-serine at the position corresponding to position 34 of SEQ ID NO:2, a non-serine at the position corresponding to position 58 of SEQ ID NO:2; a non-proline at the position corresponding to position 181 of SEQ ID NO:2, a non-alanine at the position corresponding to position 210 of SEQ ID NO:2, a non-threonine at the position corresponding to position 216 of SEQ ID NO:2, a non-aspartic acid at the position corresponding to position 258 of SEQ ID NO:2, a non-serine at the position corresponding to position 264 of SEQ ID NO:2, a non-lysine at the position corresponding to position 328 of SEQ ID NO:2, a non-aspartic acid at the position corresponding to position 364 of SEQ ID NO:2, a non-aspartic acid at the position corresponding to position 387 of SEQ ID NO:2, a non-isoleucine at the position corresponding to position 440 of SEQ ID NO:2, a non-arginine at the position corresponding to position 467 of SEQ ID NO:2, and a non-isoleucine at the position corresponding to position 479 of SEQ ID NO:2. When expressed in a plant cell, the polynucleotide can increase the fatty acid content of the plant cell compared to a plant cell comprising a comparable polynucleotide without the modification.

Methods of producing a plant cell having increased oil content, by transforming a plant cell with the modified polynucleotides disclosed herein are provided. The plant cell can have increased oil content, protein content or a combination thereof, compared with a cell not comprising the modified polynucleotide. The polypeptides produced by the polynucleotides can show increased activity and/or stability when expressed in the cell. The cell can be a soybean cell, such as a soybean seed cell. Plants regenerated from the cell may produce seeds having an increase fatty acid and/or protein content.

Modified DGAT1 polynucleotides encoding a polypeptide having at least 60%, 65%, 70%, 75%, 80%, 85%, 90%, 95%, 96%, 97%, 98%, or 99% identity from position 108 to 504 of SEQ ID NO: 2 are provided which contain a deletion of 1 to 105 amino acids from position 1 to position 107 of SEQ ID NO: 2 and have at least one amino acid substitution selected from a non-serine at the position corresponding to position 24 of SEQ ID NO:2, a non-serine at the position corresponding to position 34 of SEQ ID NO:2, a non-serine at the position corresponding to position 58 of SEQ ID NO:2; a non-proline at the position corresponding to position 181 of SEQ ID NO:2, a non-alanine at the position corresponding to position 210 of SEQ ID NO:2, a non-threonine at the position corresponding to position 216 of SEQ ID NO:2, a non-lysine acid at the position corresponding to position 244 of SEQ ID NO:2, a non-aspartic acid at the position corresponding to position 258 of SEQ ID NO:2, a non-serine at the position corresponding to position 264 of SEQ ID NO:2, a non-lysine at the position corresponding to position 328 of SEQ ID NO:2, a non-cysteine at the position corresponding to position 355 of SEQ ID NO:2, a non-aspartic acid at the position corresponding to position 364 of SEQ ID NO:2, a non-aspartic acid at the position corresponding to position 387 of SEQ ID NO:2, a non-isoleucine at the position corresponding to position 440 of SEQ ID NO:2, a non-arginine at the position corresponding to position 467 of SEQ ID NO:2, a non-isoleucine at the position corresponding to position 473 of SEQ ID NO:2, and a non-isoleucine at the position corresponding to position 479 of SEQ ID NO:2. When expressed in a soybean plant cell the modified polynucleotides can increase oil content of the soybean plant cell. The polypeptide encoded by the polynucleotide can include one or more or all three substitutions selected from a non-cysteine at position 355 of SEQ ID NO: 2, a non-arginine at position 473 of SEQ ID NO: 2, and a non-isoleucine at position 479 of SEQ ID NO: 2. The polypeptide substitutions can be a serine at position 355 of SEQ ID NO: 2, a serine at position 473 of SEQ ID NO: 2, and/or a serine at position 479 of SEQ ID NO: 2. The polypeptide encoded by the polynucleotide can include one or both of an amino acid substitution, such as a serine, at the position corresponding to position 258 of SEQ ID NO:2 and an amino acid substitution, such as an aspartate at the position corresponding to position 479 of SEQ ID NO:2.

The polypeptide encoded by the polynucleotide can include an amino acid substitution selected from one or more or all four of the following: an amino acid substitution, such as threonine, at the position corresponding to position 216 of SEQ ID NO:2, an amino acid substitution, such as aspartate, at the position corresponding to position 258 of SEQ ID NO:2, an amino acid substitution, such as serine, at the position corresponding to position 264 of SEQ ID NO:2 and an amino acid substitution, such as an aspartate, at the position corresponding to position 479 of SEQ ID NO:2.

In plant cells, seeds, soybean cells and soybean seeds expressing the modified polynucleotides, the oil content can be increased by at least 5%, 10%, 15% or 20% compared to a comparable cell or seed expressing the polynucleotide without the modification.

Methods of producing a soybean seed are provided which include the steps of sexually crossing a first soybean line comprising a polynucleotide disclosed herein, with a second soybean line not comprising the polynucleotide and harvesting the seed produced from the cross. The method can include a further step of backcrossing a second generation progeny plant produced from the seed that comprises the polynucleotide to the parent plant that lacks the polynucleotide, to produce a backcross progeny plant that produces seed with increased fatty acid content.

Methods of screening for the presence or absence of the modified polynucleotides disclosed herein in a plurality of genomic soybean DNA samples are provided, which include the steps of contacting a plurality of genomic soybean DNA samples, at least some of which comprise the polynucleotides, with a first DNA primer molecule and a second DNA primer molecule; providing nucleic acid amplification reaction conditions and performing the nucleic acid amplification reactions, to produce a DNA amplicon molecule indicating the presence of the polynucleotide or a wild-type DGAT1 nucleotide sequence and detecting the DNA amplicon molecules, wherein the presence, absence or size of the DNA amplicon molecule indicates the presence or absence of the polynucleotide in the at least one of the plurality of genomic soybean DNA samples.

BRIEF DESCRIPTION OF THE DRAWINGS AND SEQUENCE LISTING

The disclosure can be more fully understood from the following detailed description and the accompanying drawings and Sequence Listing that form a part of this application, which are incorporated herein by reference.

FIG. 1 is a graph showing DGAT protein level in tobacco leaf with expression of DGAT variants. DGAT1b mod is soybean DGAT1b with 14 amino acid substitutions (SEQ ID NO:26). A significant difference between DGAT variant and wild type DGAT at P<0.05 was found in the four DGAT variants. A significant difference between DGAT variant and wild type DGAT at P<0.05 is marked with asterisks.

Figure 2:
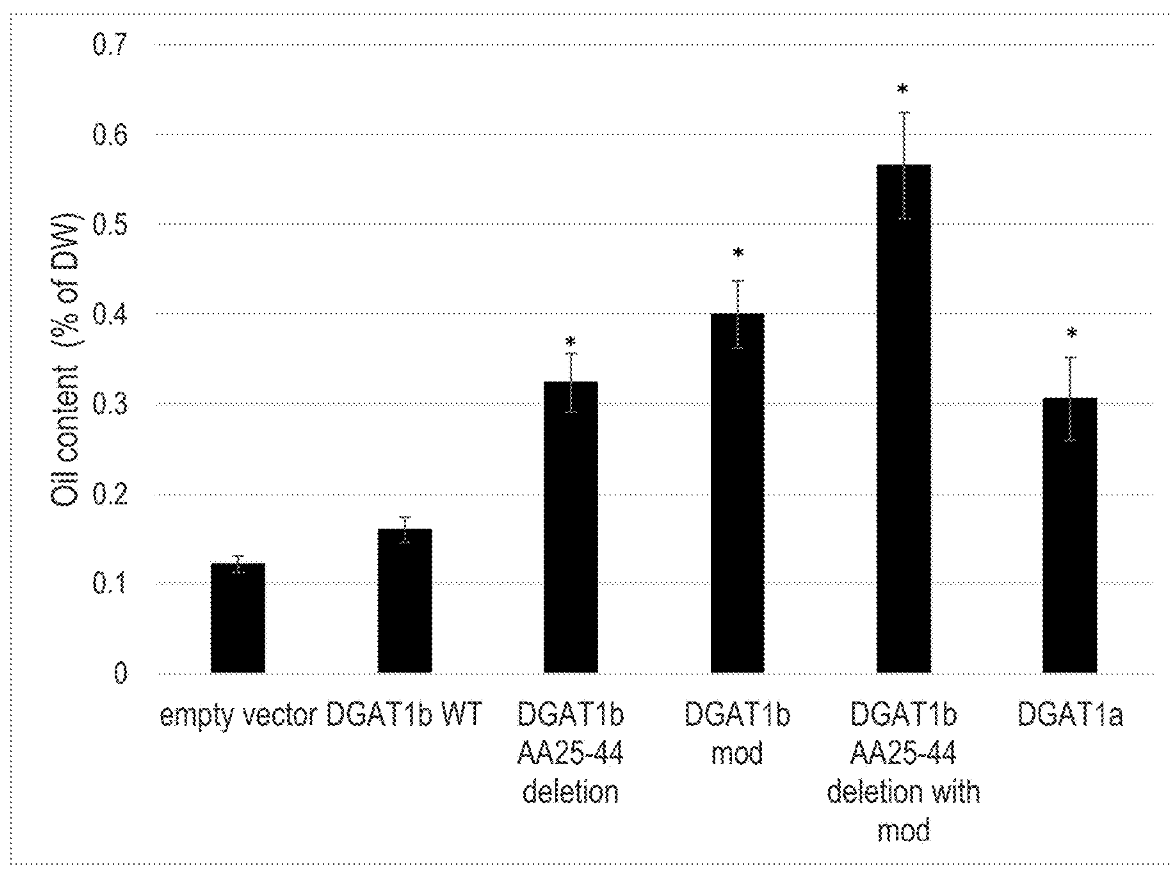

FIG. 2 is a graph showing the oil content in tobacco leaf expressing different DGAT variants. DGAT1b mod is soybean DGAT1b with 14 amino acid substitutions (SEQ ID NO:26). A significant difference between DGAT variant and wild type DGAT at P<0.05 was found in the four DGAT variants. A significant difference between DGAT variant and wild type DGAT at P<0.05 is marked with asterisks.

Figure 3:
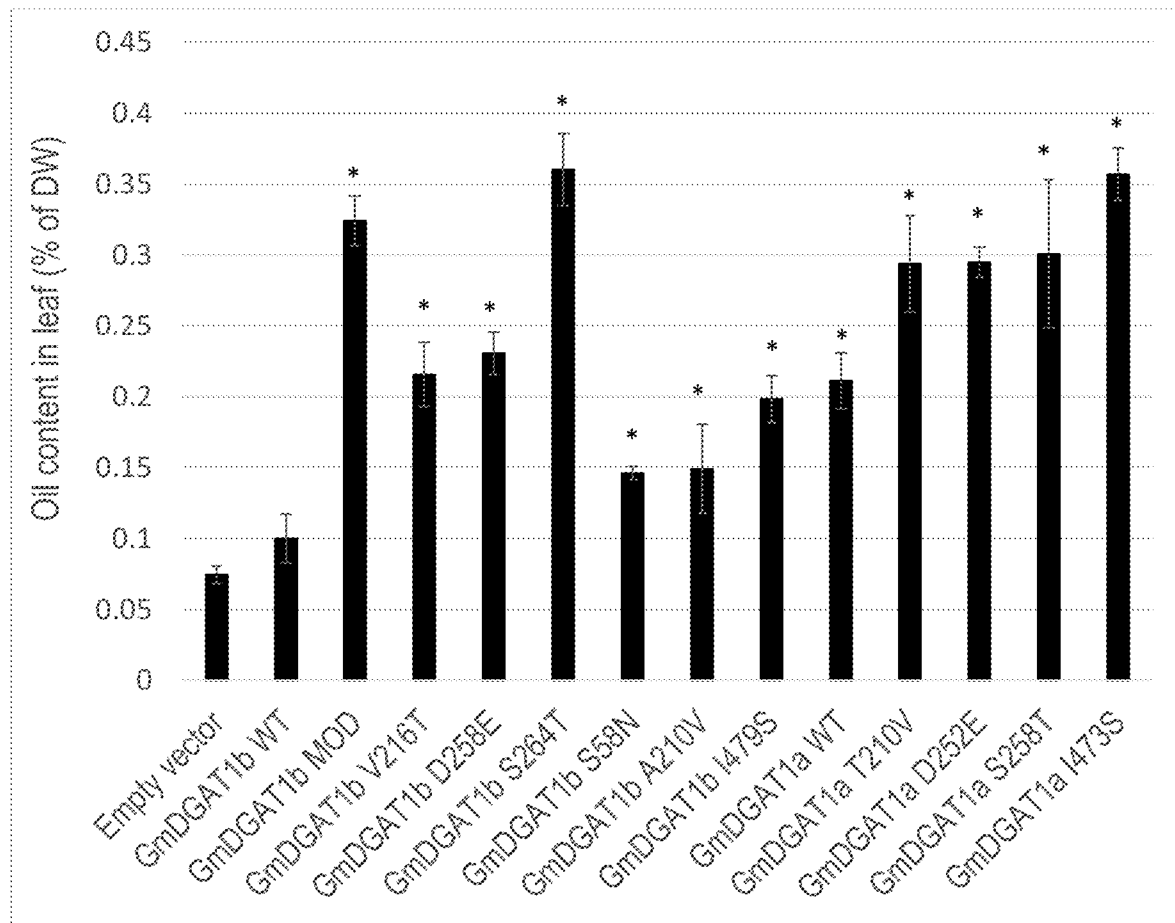

FIG. 3. is a graph showing the oil content in tobacco leaf tobacco leaf expressing different DGAT variants. A single amino acid substitution in GmDGAT1a and GmDGAT1b increases oil content in tobacco leaf transient expression. GmDGAT1b mod is soybean DGAT1b with 14 amino acid substitutions (SEQ ID NO:26). A significant difference between DGAT variant and wild type DGAT at P<0.05 was found in the twelve DGAT variants.

FIG. 4 A-D is a sequence alignment of plant DGAT amino acid sequences with the amino acid substitutions which correspond to the positions described herein marked with stars.

Figure 5:
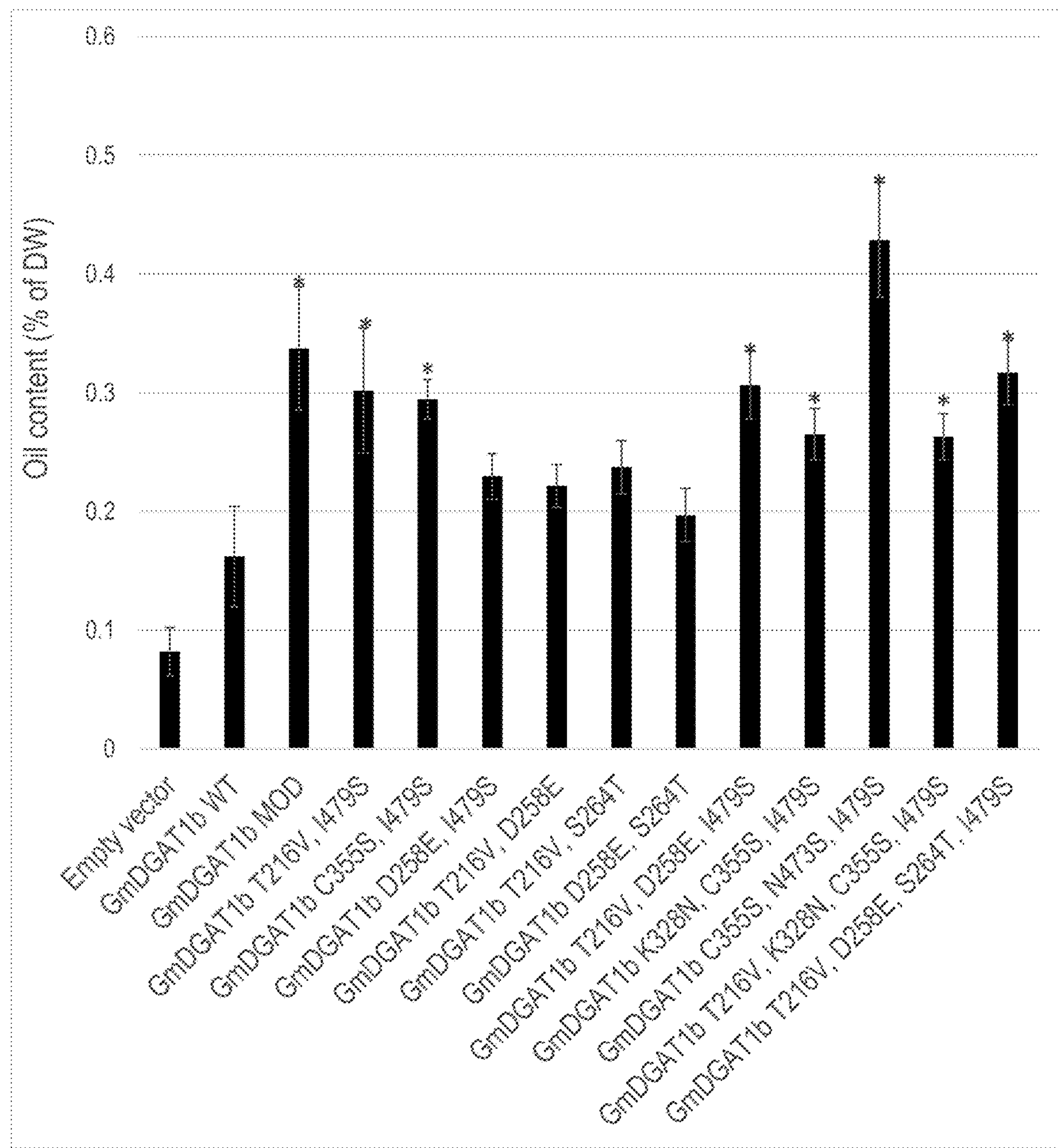

FIG. 5 is a graph showing the oil content in tobacco leaf expressing different DGAT variants. Changes of two to four amino acids in DGAT increases oil content in tobacco leaf transient expression. GmDGAT1b mod is soybean DGAT1b with 14 amino acid substitutions (SEQ ID NO:26). A significant difference between DGAT variant and wild type DGAT at P<0.05 was found in the 8 (marked with asterisks) of the 12 DGAT variants.

Figure 6:
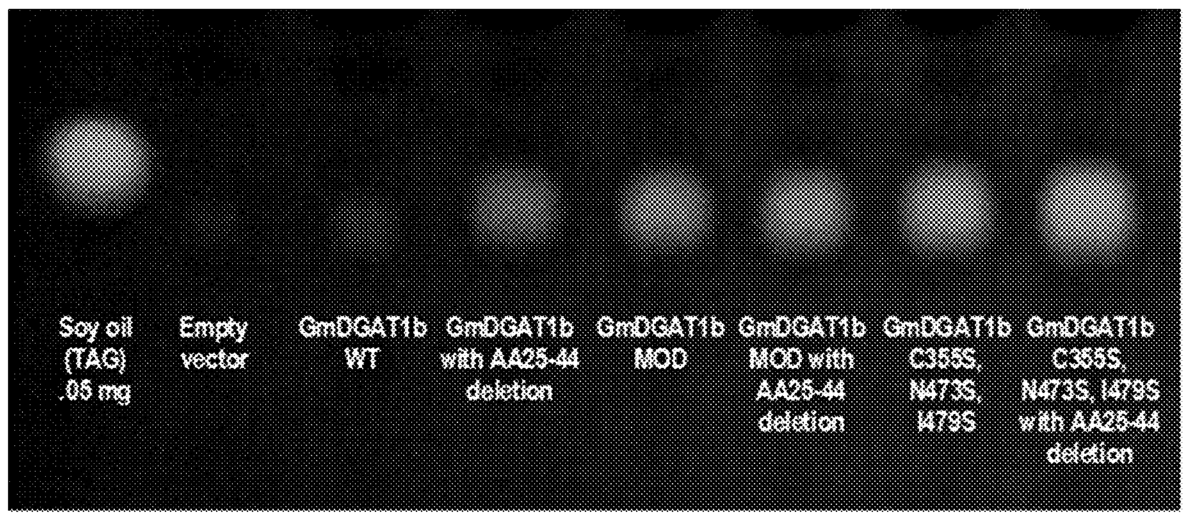

FIG. 6 is a photograph showing the oil content in tobacco leaf expressing different DGAT variants. The combination of 3 amino acid substitutions with N-terminal deletion at AA25-44 increases oil more than either 3 amino acid substitution or the N-terminal deletion at AA25-44 alone and is higher than GmDGAT1b mod with 14 amino acid substitutions (SEQ ID NO:26).

The sequence descriptions summarize the Sequence Listing attached hereto. The Sequence Listing contains one letter codes for nucleotide sequence characters and the single and three letter codes for amino acids as defined in the IUPAC IUB standards described in Nucleic Acids Research 13:3021 3030 (1985) and in Biochem. J. 219(2):345 373 (1984).

Figure 7:
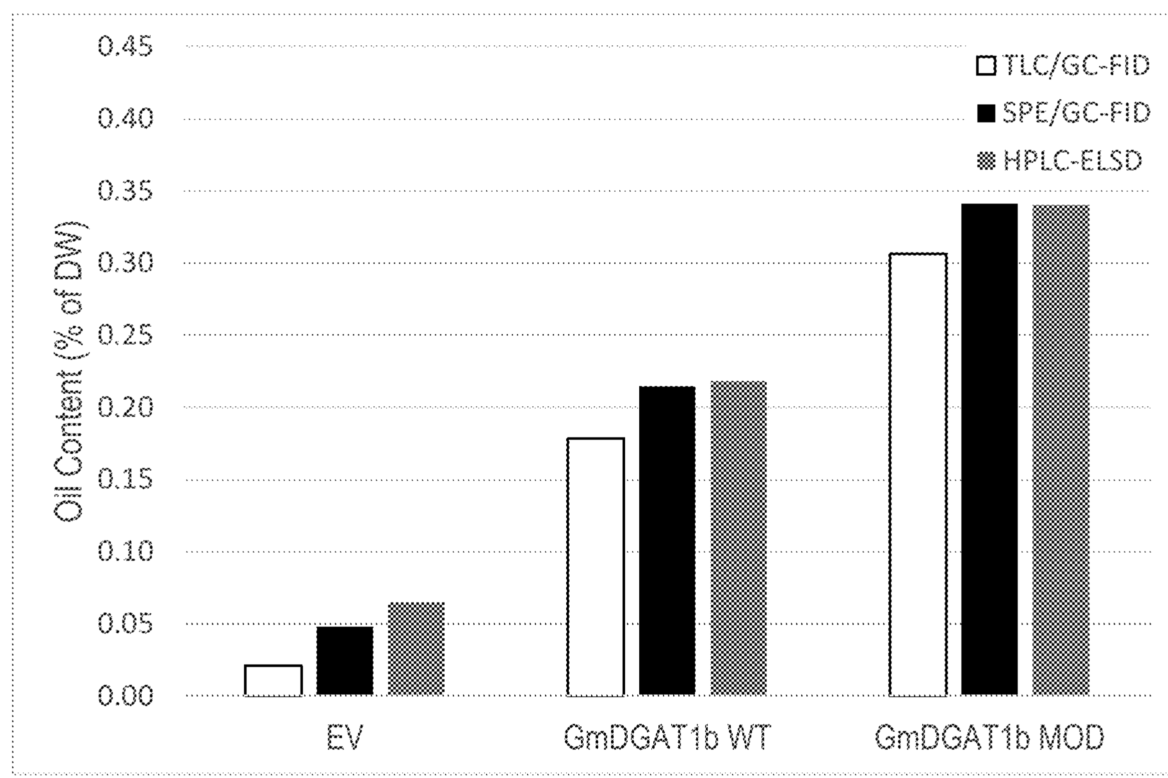

FIG. 7 is a graph showing the oil content from GmDGAT1b wild type (SEQ ID NO:2), GmDGAT1b mod (SEQ ID NO:2), and empty vector expressed in tobacco leaf and compare three different TAG isolation and quantification procedures, including TLC/GC-FID, SPE/GC-FID, and HPLC-ELSD. Samples were analyzed with each of the three analysis methods. GmDGAT1b mod is soybean DGAT1b with 14 amino acid substitutions (SEQ ID NO:26).

Figure 8:
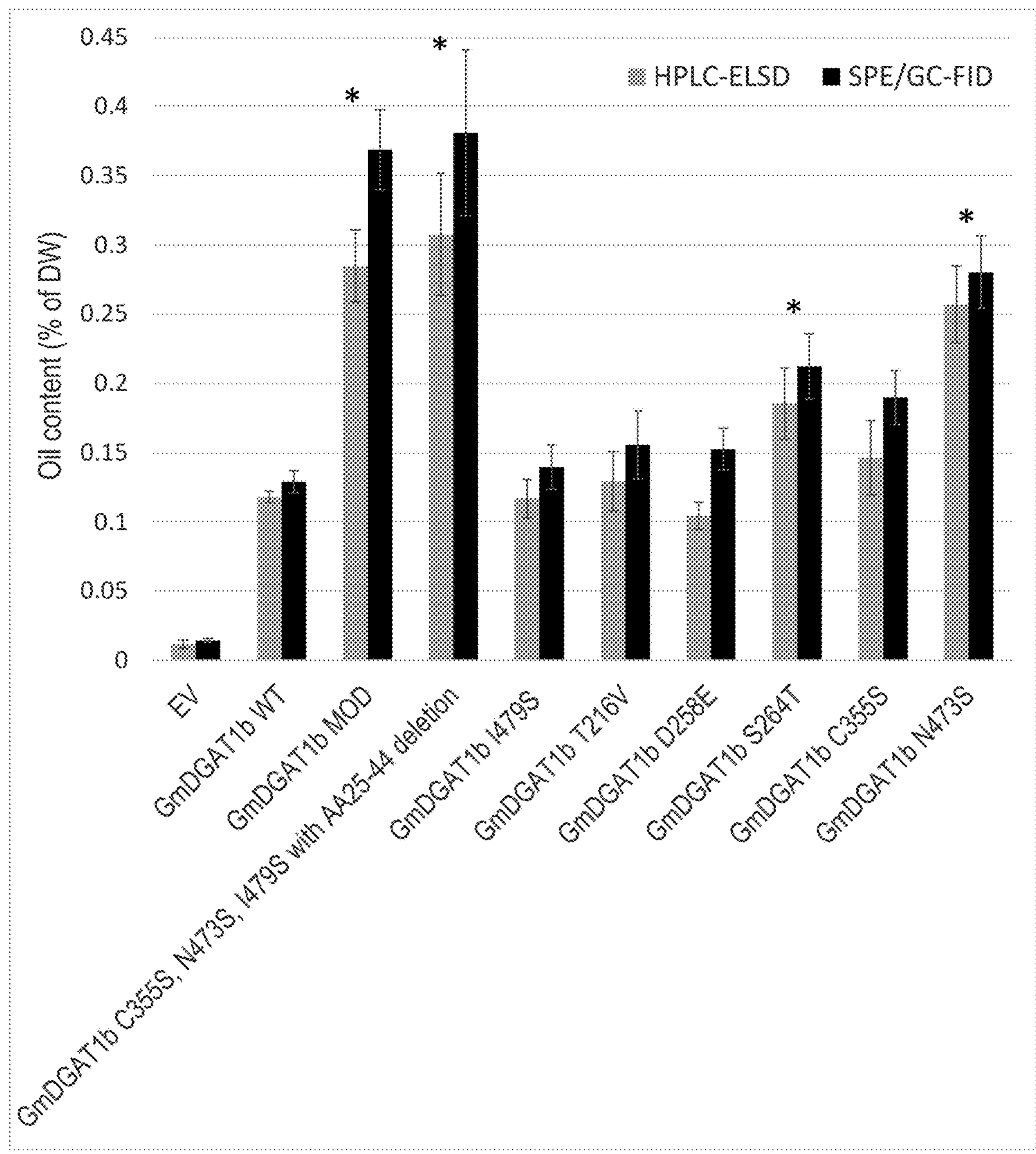

FIG. 8 is a graph showing the oil content in tobacco leaf expressing additional DGAT1 variants analyzed with the HPLC-ELSD and SPE/GC-FID procedures. Single amino acid substitutions in GmDGAT1b increases oil content in tobacco leaf transient expression system. GmDGAT1b mod is soybean DGAT1b with 14 amino acid substitutions (SEQ ID NO:26). A significant difference between DGAT variants and wild type DGAT at p<0.05 was found in the 4 (marked with an asterisks) of the 8 DGAT variants.

Figure 9:
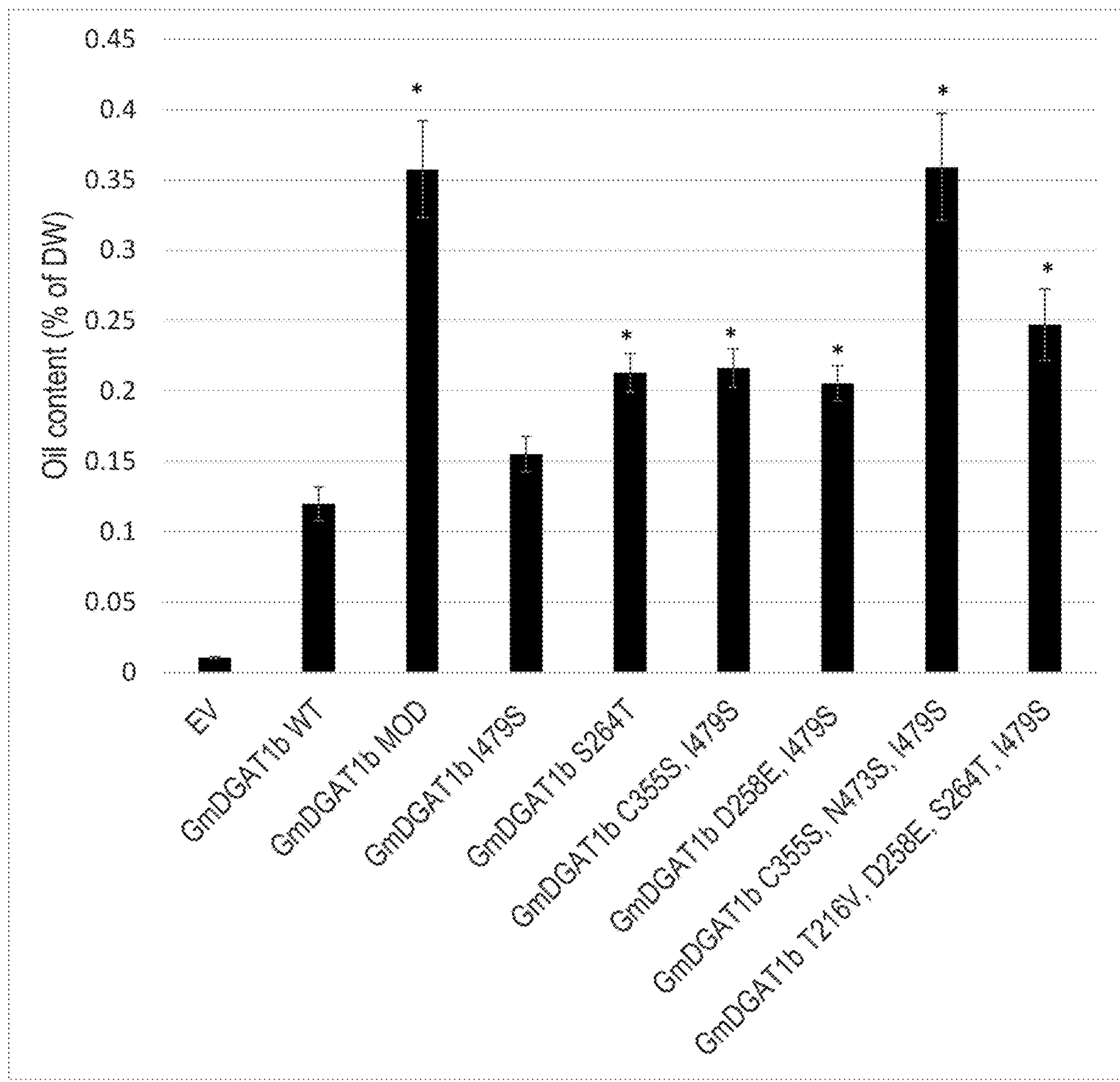

FIG. 9 is a graph showing the oil content in tobacco leaf expressing different DGAT variants analyzed with the SPE/GC-FID procedure. Changes of one to four amino acids in DGAT increases oil content in tobacco leaf transient expression. GmDGAT1b mod is soybean DGAT1b with 14 amino acid substitutions (SEQ ID NO:26). A significant difference between DGAT variants and wild type DGAT at p<0.05 was found in the 6 (marked with asterisks) of the 7 DGAT variants.

Figure 10:
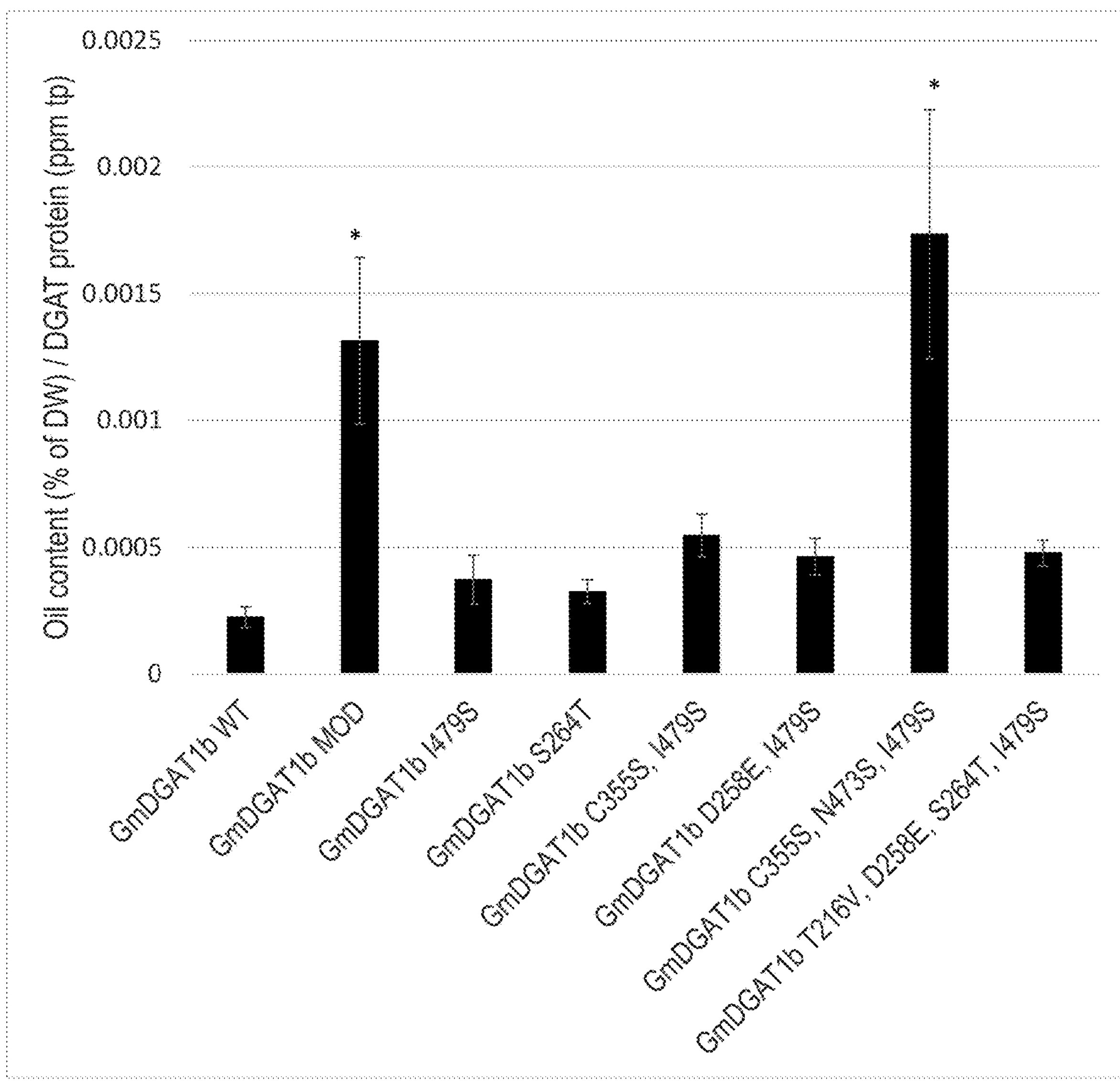

FIG. 10 is a graph showing the oil/protein ratio in tobacco leaf expressing different DGAT variants from FIG. 9. GmDGAT1b mod is soybean DGAT1b with 14 amino acid substitutions (SEQ ID NO:26). A significant difference between DGAT variants and wild type DGAT at p<0.05 was found in the 2 (marked with asterisks) of the 7 DGAT variants.

TABLE 1

List of sequences used in this application

| Sequence | Nucleotide SEQ ID NO: | Polypeptide SEQ ID NO: |
|---|---|---|
| *Glycine max* GmDGAT1b | 1 | 2 |
| *Glycine max* GmDGAT1a | 3 | 4 |
| *Glycine max* GmDGAT1C | 5 | 6 |
| *Brassica napus* BnDGAT1a | 7 | 8 |
| *Gossypium hirsutum* GhDGAT1 | 9 | 10 |
| *Helianthus annuus* HaDGAT1 | 11 | 12 |
| *Hordeum vulgare* DGAT1 | 13 | 14 |
| *Oryza sativa* DGAT1 | 15 | 16 |
| *Sorghum bicolor* DGAT1b | 17 | 18 |
| *Triticum aestivum* DGAT1 | 19 | 20 |
| *Zea mays* DGAT1-2 | 21 | 22 |
| *Elaeis guineensis* DGAT1-1 | 23 | 24 |
| *Glycine max* GmDGAT1a with 48 bp deletion | 25 | |
| *Glycine max* GmDGAT1B with 60 bp deletion | 26 | |
| *Glycine max* GmDGAT1b mod | | 27 |
| *Glycine max* GmDGAT1a mod | | 28 |
| *Glycine max* GmDGAT1b genomic | 29 | |
| *Glycine max* GmDGAT1a genomic | 30 | |
| GM-DGAT-CR1 | 31 | |
| GM-DGAT-CR3 | 32 | |
| GM-DGAT-CR4 | 33 | |
| DGAT1a WOL1469 | 34 | |
| DGAT1a WOL1470 primer | 35 | |
| DGAT1b WOL1471 primer | 36 | |
| DGAT1b WOL1472 primer | 37 | |
| DGAT polypeptide motif | | 38 |
| DGAT polypeptide motif | | 39 |
| DGAT polypeptide motif | | 40 |
| DGAT polypeptide motif | | 41 |
| DGAT polypeptide motif | | 42 |

DETAILED DESCRIPTION

Compositions and methods related to modified plants, such as soybean plants, producing seeds high in oil are provided. The seeds may also have increased amounts of protein. Suitable plants include oil-seed plants, such as palm, canola, sunflower and soybean as well as, without limitation, rice, cotton, sorghum, wheat, maize, alfalfa and barley. Plants, such as soybean plants, that have been modified using genomic editing techniques to produce seeds having a desirable fatty acid content are provided. The inventors found that providing particular amino acid substitutions, or combinations of amino acid substitutions, as well as particular deletions in diacylglycerol acyltransferase (DGAT) alleles using genomic editing technology as described herein provided a DGAT protein with higher activity and increased stability. Plant cells containing the modified DGAT sequences show increased fatty acid or oil content.

The modified sequences, plants, seeds and cells disclosed herein are produced by genomic editing techniques which facilitate the editing of the DGAT alleles, such as provided in SEQ ID NOs: 1-30. The sense strand or the complement thereof may be edited.

A “DGAT”, “DGAT1”, “DGAT1a” or “DGAT1b” or a “DGAT-modified plant”, “DGAT1-modified plant”, “DGAT1a-modified plant” or “DGAT1b-modified plant” generally refers to a modified or mutant plant or plant cell that has one or more nucleotide changes or deletions in a genomic region that encodes a polypeptide that is at least 70%, 75%, 80%, 85%, 90%, 95%, 96%, 97%, 98% or 99% identical to one of SEQ ID NOS: 1-24 or an allelic variant thereof. DGAT1a and DGAT1b may also be written as DGAT1A and DGAT1B, respectively. The nucleotide changes in the sequences encoding a DGAT polypeptide disclosed herein can include modifications that result in one or more amino acid substitutions at an amino acid corresponding to those listed in Table 2, either alone or in any combination. Amino acids corresponding to those listed in Table 2, for example, are shown with an asterisk in FIG. 4. The modified DGAT sequences when expressed in cells, plants and seeds may show an increase in oil and may be more stable, show an increase in specific activity or any combination thereof. An increase in protein and fatty acid content in the plant cell or in a seed comprising the plant cell may also result from expression of the modified polynucleotides disclosed herein. The polynucleotides may also have at least about 40%, 45%, 50%, 55%, 60%, 65%, 70%, 75%, 80%, 85%, 90%, 95%, 96%, 97%, 98% or 99% identity, such as according to parameters disclosed herein, to their corresponding genomic nucleotide sequence, such as SEQ ID NO: 29 or 30.

TABLE 2

Positions for amino acid substitutions in DGAT sequences

| GmDGAT1B (SEQ ID NO: 2) Soy | GmDGAT1a (SEQ ID NO: 4) Soy | GmDGAT1C (SEQ ID NO: 6) Soy | BnDGAT1a (SEQ ID NO: 8) Canola | GhDGAT1 (SEQ ID NO: 10) Cotton | HaDGAT1 (SEQ ID NO: 12) Sunflower | HvDGAT1 (SEQ ID NO: 14) Barley |
|---|---|---|---|---|---|---|
| S58 | S55 | D71 | E64 | D63 | A68 | — |
| P181 | P175 | S194 | S188 | S186 | S194 | R147 |
| A210 | A204 | A233 | A217 | A215 | V223 | A176 |
| T216 | T210 | T229 | T223 | A221 | S229 | V182 |
| D258 | D252 | E271 | E258 | — | E271 | E224 |
| S264 | S258 | T277 | S264 | S262 | D277 | T230 |
| K328 | K322 | K341 | K328 | K326 | N341 | K294 |
| L364 | L358 | L377 | L364 | L362 | L377 | L330 |
| D387 | D381 | E400 | D387 | E385 | E400 | E353 |
| I440 | I434 | M453 | L440 | L438 | I453 | I406 |
| R467 | R461 | R480 | — | Q465 | Q480 | K433 |
| I479 | I473 | I492 | A478 | I477 | F492 | F445 |
| S24 | T24 | S32 | S30 | D26 | S24 | A23 |
| S34 | S31 | D42 | D40 | A36 | S44 | — |
| L244 | S238 | S257 | S251 | S249 | S257 | S210 |
| C355 | C349 | C368 | C355 | S353 | C368 | C321 |
| N473 | N467 | N486 | N472 | N471 | N486 | N439 |

| OsDGAT1 (SEQ ID NO: 16) Rice | SbDGAT1b (SEQ ID NO: 18) Sorghum | TaDGAT1 (SEQ ID NO: 20) Wheat | ZmDGAT1-2 (SEQ ID NO: 22) Maize | EgDGAT1-1 (SEQ ID NO: 24) Palm |
|---|---|---|---|---|
| S78 | E57 | L61 | G51 | G60 |
| T215 | T192 | R187 | G170 | S197 |
| A244 | A221 | A216 | A199 | P226 |
| L250 | V227 | V222 | V205 | N232 |
| D292 | D269 | E264 | E247 | H266 |
| T298 | T275 | T270 | T253 | S272 |
| K362 | K339 | K334 | K317 | K336 |
| L398 | L375 | L370 | V353 | L372 |
| E421 | E398 | E393 | E376 | E395 |
| I474 | I451 | I446 | I429 | I448 |
| R501 | N478 | K473 | K456 | K475 |
| F513 | F490 | F485 | F468 | F487 |
| A44 | G23 | K27 | G21 | P26 |
| A54 | K33 | P37 | A31 | S36 |
| G278 | S255 | S250 | S233 | S260 |
| A389 | C366 | S361 | C344 | C363 |
| N507 | N484 | N479 | N462 | N481 |

The substitutions may include one or more of the following with respect to the corresponding position in SEQ ID NO:2: S24A, S34A, S58N, P181A, A210V, T216V, L244A, D258E, S264T, K328N, C355S, L364V, D387E, I440M, R467Q, N473S, and I479S.

In some embodiments the polynucleotides disclosed herein may be isolated polynucleotides. An “isolated polynucleotide” generally refers to a polymer of ribonucleotides (RNA) or deoxyribonucleotides (DNA) that is single- or double-stranded, optionally containing synthetic, non-natural or altered nucleotide bases. An isolated polynucleotide in the form of DNA may be comprised of one or more segments of cDNA, genomic DNA or synthetic DNA.

The terms "polynucleotide", "polynucleotide sequence", "nucleic acid sequence", "nucleic acid fragment", and "isolated nucleic acid fragment" encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

A regulatory element generally refers to a transcriptional regulatory element involved in regulating the transcription of a nucleic acid molecule such as a gene or a target gene. The regulatory element is a nucleic acid and may include a promoter, an enhancer, an intron, a 5'-untranslated region (5'-UTR, also known as a leader sequence), or a 3'-UTR or a combination thereof. A regulatory element may act in "cis" or "trans", and generally it acts in "cis", i.e. it activates expression of genes located on the same nucleic acid molecule, e.g. a chromosome, where the regulatory element is located. The nucleic acid molecule regulated by a regulatory element does not necessarily have to encode a functional peptide or polypeptide, e.g., the regulatory element can modulate the expression of a short interfering RNA or an anti-sense RNA.

An enhancer element is any nucleic acid molecule that increases transcription of a nucleic acid molecule when functionally linked to a promoter regardless of its relative position. An enhancer may be an innate element of the promoter or a heterologous element inserted to enhance the level or tissue-specificity of a promoter.

A repressor (also sometimes called herein silencer) is defined as any nucleic acid molecule which inhibits the transcription when functionally linked to a promoter regardless of relative position.

Promotors which may be useful in the methods and compositions provided include those containing cis elements, promoters functional in a plant cell, tissue specific and tissue-preferred promotors, developmentally regulated promoters and constitutive promoters. "Promoter" generally refers to a nucleic acid fragment capable of controlling transcription of another nucleic acid fragment. A promoter generally includes a core promoter (also known as minimal promoter) sequence that includes a minimal regulatory region to initiate transcription, that is a transcription start site. Generally, a core promoter includes a TATA box and a GC rich region associated with a CAAT box or a CCAAT box. These elements act to bind RNA polymerase to the promoter and assist the polymerase in locating the RNA initiation site. Some promoters may not have a TATA box or CAAT box or a CCAAT box, but instead may contain an initiator element for the transcription initiation site. A core promoter is a minimal sequence required to direct transcription initiation and generally may not include enhancers or other UTRs. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Core promoters are often modified to produce artificial, chimeric, or hybrid promoters, and can further be used in combination with other regulatory elements, such as cis-elements, 5'UTRs, enhancers, or introns, that are either heterologous to an active core promoter or combined with its own partial or complete regulatory elements. Endogenous promotors are those sequences that are operably connected to a polypeptide coding sequence in the native gene and which regulate transcription of the polypeptide coding sequence in the plant. An endogenous promotor of a modified polynucleotide is one which is operably connected to and regulates or controls transcription of the unmodified version of the polynucleotide in the native, unmodified or wild-type plant.

The term "cis-element" generally refers to transcriptional regulatory element that affects or modulates expression of an operably linked transcribable polynucleotide, where the transcribable polynucleotide is present in the same DNA sequence. A cis-element may function to bind transcription factors, which are trans-acting polypeptides that regulate transcription.

"Promoter functional in a plant" is a promoter capable of initiating transcription in plant cells whether or not its origin is from a plant cell.

"Tissue-specific promoter" and "tissue-preferred promoter" are used interchangeably to refer to a promoter that is expressed predominantly but not necessarily exclusively in one tissue or organ, but that may also be expressed in one specific cell.

"Developmentally regulated promoter" generally refers to a promoter whose activity is determined by developmental events.

"Constitutive promoter" generally refers to promoters active in all or most tissues or cell types of a plant at all or most developing stages. As with other promoters classified as "constitutive" (e.g. ubiquitin), some variation in absolute levels of expression can exist among different tissues or stages. The term "constitutive promoter" or "tissue-independent" are used interchangeably herein.

Variant promotors can be used in the methods and compositions disclosed herein. A "variant promoter" as used herein, is the sequence of the promoter or the sequence of a functional fragment of a promoter containing changes in which one or more nucleotides of the original sequence is deleted, added, and/or substituted, while substantially maintaining promoter function. One or more base pairs can be inserted, deleted, or substituted internally to a promoter. In the case of a promoter fragment, variant promoters can include changes affecting the transcription of a minimal promoter to which it is operably linked. Variant promoters can be produced, for example, by standard DNA mutagenesis techniques or by chemically synthesizing the variant promoter or a portion thereof.

Provided are sequences which are heterologous nucleotide sequences which can be used in the methods and compositions disclosed herein. A "heterologous nucleotide sequence" generally refers to a sequence that is not naturally occurring with the sequence of the disclosure. While this nucleotide sequence is heterologous to the sequence, it may be homologous, or native, or heterologous, or foreign, to the plant host. However, it is recognized that the instant sequences may be used with their native coding sequences to increase or decrease expression resulting in a change in phenotype in the transformed seed. The terms "heterologous nucleotide sequence", "heterologous sequence", "heterologous nucleic acid fragment", and "heterologous nucleic acid sequence" are used interchangeably herein.

Provided are functional fragments of the sequences disclosed herein. A "functional fragment" refers to a portion or subsequence of the sequence described in the present disclosure in which the active properties of the full-length sequence is retained. Fragments can be obtained via methods such as site-directed mutagenesis and synthetic construction. For example, for promoter sequences described or used herein, the functional fragments operate to promote the expression of an operably linked heterologous nucleotide sequence, forming a recombinant DNA construct (also, a chimeric gene). For example, the fragment can be used in the design of recombinant DNA constructs to produce the desired phenotype in a transformed plant. Recombinant DNA constructs can be designed for use in co-suppression or antisense by linking a promoter fragment in the appropriate orientation relative to a heterologous nucleotide sequence.

A nucleic acid fragment that is functionally equivalent to the sequences of the present disclosure is any nucleic acid fragment that is capable of being expressed in a similar manner to the Target sequences of the present disclosure.

In some aspects of the present disclosure, the fragments of polynucleotide sequences disclosed herein (such as SEQ ID NOS: 1, 3, 5, 7, 9, 11, 13, 15, 17, 19, 21, 23, 25, 26, 29 or 30) can comprise at least about 20, 30, 40, 50, 60, 70, 80, 90, 100, 125, 150, 175, 200, 225, 250, 275, 300, 350, 375, 400, 425, 450, 475, 500, 525, 550, 575, 600, 625, 650, 675, 700, 725, 750, 7775, 800, 825, 850, 875, 900, 925, 950, 1000, 1025, 1050, 1075, 1100, 1125, 1150, 1175, 1200, 1225, 1250, 1275, 1300, 1325, 1350, 1375, 1400, 1420, 1450, 1475 or 1500 contiguous nucleotides, or at least about 20, 30, 40, 50, 60, 70, 80, 90, 100, 125, 150, 175, 200, 225, 250, 275, 300, 350, 375, 400, 425, 450, 475, 500, 525, 550, 575, 600, 625, 650, 675, 700, 725, 750, 7775, 800, 825, 850, 875, 900, 925, 950, 1000, 1025, 1050, 1075, 1100, 1125, 1150, 1175, 1200, 1225, 1250, 1275, 1300, 1325, 1350, 1375, 1400, 1420, 1450, 1475 or 1500 contiguous nucleotides of nucleic acid sequences encoding polypeptides of SEQ ID NOS: 1, 3, 5, 7, 9, 11, 13, 15, 17, 19, 21 or 23. In another aspect of the present disclosure, the fragments can comprise at least about 250 contiguous nucleotides, or at least about 300 contiguous nucleotides, or at least about 350 contiguous nucleotides, or at least about 400 contiguous nucleotides, or at least about 450 contiguous nucleotides, or at least about 500 contiguous nucleotides, or at least about 550 contiguous nucleotides, or at least about 600 contiguous nucleotides, or at least about 650 contiguous nucleotides, or at least about 700 contiguous nucleotides, or at least about 750 contiguous nucleotides, or at least about 800 contiguous nucleotides, or at least about 850 contiguous nucleotides, or at least about 900 contiguous nucleotides, or at least about 950 contiguous nucleotides, or at least about 1000 contiguous nucleotides, or at least about 1050 contiguous nucleotides, or at least about 1110 contiguous nucleotides, or at least about 1150 contiguous nucleotides, or at least about 1200, or at least about 1250 contiguous nucleotides, or at least about 1300 contiguous nucleotides or at least about 1350 contiguous nucleotides and further may include a sequence encoding an amino acid modification corresponding to the substitutions described herein.

Provided are sequences that are a full complement or a full-length complement of those disclosed herein, such as the nucleotide coding sequences in Table 1 containing the modifications disclosed herein. The terms "full complement" and "full-length complement" are used interchangeably herein, and refer to a complement of a given nucleotide sequence, wherein the complement and the nucleotide sequence consist of the same number of nucleotides and are 100% complementary.

Provided are sequences that are "substantially similar" or "corresponding substantially" to those disclosed herein which can be used in the methods and compositions described herein. The terms "substantially similar" and "corresponding substantially" as used herein refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant disclosure such as deletion or insertion of one or more nucleotides that do not substantially alter the functional properties of the resulting nucleic acid fragment relative to the initial, unmodified fragment. It is therefore understood, as those skilled in the art will appreciate, that the disclosure encompasses more than the specific exemplary sequences.

Provided are compositions and methods that includes materials, steps, features, components, or elements that consist essentially of a particular component. The transitional phrase "consisting essentially of" generally refers to a composition, method that includes materials, steps, features, components, or elements, in addition to those literally disclosed, provided that these additional materials, steps, features, components, or elements do not materially affect the basic and novel characteristic(s) of the claimed subject matter, e.g., one or more of the claimed sequences.

Isolated promoter sequences can be comprised in the methods and compositions, such as a recombinant DNA construct, of the present disclosure and can be modified to provide a range of constitutive expression levels of the heterologous nucleotide sequence. Thus, less than the entire promoter regions may be utilized and the ability to drive expression of the coding sequence retained. However, it is recognized that expression levels of the mRNA may be decreased with deletions of portions of the promoter sequences. Likewise, the tissue-independent, constitutive nature of expression may be changed.

Modifications of the isolated promoter sequences of the present disclosure can provide for a range of constitutive expression of the heterologous nucleotide sequence. Thus, they may be modified to be weak constitutive promoters or strong constitutive promoters. Generally, by "weak promoter" is intended a promoter that drives expression of a coding sequence at a low level. By "low level" is intended levels about 1/10,000 transcripts to about 1/100,000 transcripts to about 1/500,000 transcripts. Conversely, a strong promoter drives expression of a coding sequence at high level, or at about 1/10 transcripts to about 1/100 transcripts to about 1/1,000 transcripts. Similarly, a "moderate constitutive" promoter is somewhat weaker than a strong constitutive promoter like the maize ubiquitin promoter.

In addition to modulating gene expression, the expression modulating elements disclosed herein are also useful as probes or primers in nucleic acid hybridization experiments. The nucleic acid probes and primers hybridize under stringent conditions to a target DNA sequence. A "probe" is generally referred to an isolated/synthesized nucleic acid to which, is attached a conventional detectable label or reporter molecule, such as for example, a radioactive isotope, ligand, chemiluminescent agent, bioluminescent molecule, fluorescent label or dye, or enzyme. Such detectable labels may be covalently linked or otherwise physically associated with the probe. "Primers" generally referred to isolated/synthesized nucleic acids that hybridize to a complementary target DNA strand which is then extended along the target DNA strand by a polymerase, e.g., a DNA polymerase. Primer pairs often used for amplification of a target nucleic acid sequence, e.g., by the polymerase chain reaction (PCR) or other conventional nucleic-acid amplification methods. Primers are also used for a variety of sequencing reactions, sequence captures, and other sequence-based amplification methodologies. Primers are generally about 15, 20, 25 nucleotides or more, and probes can also be longer about 30, 40, 50 and up to a few hundred base pairs. Such probes and primers are used in hybridization reactions to target DNA or RNA sequences under high stringency hybridization conditions or under lower stringency conditions, depending on the need.

Moreover, the skilled artisan recognizes that substantially similar nucleic acid sequences encompassed by this disclosure are also defined by their ability to hybridize, under moderately stringent conditions (for example, 0.5×SSC, 0.1% SDS, 60° C.) with the sequences exemplified herein, or to any portion of the nucleotide sequences reported herein and which are functionally equivalent to the promoter of the disclosure. Estimates of such homology are provided by either DNA-DNA or DNA-RNA hybridization under conditions of stringency as is well understood by those skilled in the art (Hames and Higgins, Eds.; In Nucleic Acid Hybridisation; IRL Press: Oxford, U. K., 1985). Stringency conditions can be adjusted to screen for moderately similar fragments, such as homologous sequences from distantly related organisms, to highly similar fragments, such as genes that duplicate functional enzymes from closely related organisms. Post-hybridization washes partially determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. Another set of stringent conditions uses higher temperatures in which the washes are identical to those above except for the temperature of the final two 30 min washes in 0.2×SSC, 0.5% SDS was increased to 60° C. Another set of highly stringent conditions uses two final washes in 0.1×SSC, 0.1% SDS at 65° C.

In some embodiments, substantially similar nucleic acid sequences encompassed by this disclosure are those sequences that are at least about or about 80% identical to the nucleic acid fragments reported herein or which are at least about or about 80% identical to any portion of the nucleotide sequences reported herein. Nucleic acid fragments which are at least 90% or at least 95% identical to the nucleic acid sequences reported herein, or which are at least 90% or at least 95% identical to any portion of the nucleotide sequences reported herein are also provided. It is well understood by one skilled in the art that many levels of sequence identity are useful in identifying related polynucleotide sequences. Useful examples of percent identities are those listed above, or also preferred is any integer percentage from 70% to 100%, such as at least, at least about or about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100%. In some embodiments, the sequences may have at least about or about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100% percent identity to positions 247 to 1512 of SEQ ID NO: 1, or to a sequence encoding positions 108-504 of SEQ ID NO: 2, or corresponding thereto.

In one embodiment, the nucleotide sequences or isolated or modified sequences of the present disclosure comprise at least one modification disclosed herein and comprise a nucleotide sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100% sequence identity, based on the Clustal V method of alignment with pairwise alignment default parameters (KTUPLE=2, GAP PENALTY=5, WINDOW=4 and DIAGONALS SAVED=4), when compared to the nucleotide sequence of SEQ ID NOS: 1, 3, 5, 7, 9, 11, 13, 15, 17, 19, 21, 23, 25, 26, 29 or 30 or encode polypeptides having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100% sequence identity of SEQ ID NOS: 2, 4, 6, 8, 10, 12, 14, 16, 18, 20, 22, 24, 27 or 28. It is known to one of skilled in the art that a 5' UTR region can be altered (deletion or substitutions of bases) or replaced by an alternative 5'UTR while maintaining promoter activity.

In one embodiment, the polypeptide sequences or isolated or modified sequences of the present disclosure comprise a polypeptide sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100% sequence identity of SEQ ID NOS: 2, 4, 6, 8, 10, 12, 14, 16, 18, 20, 22, 24, 27 or 28.

Provided are substantially similar sequences useful in compositions and methods provided herein. A "substantially similar sequence" generally refers to variants of the disclosed sequences such as those that result from site-directed mutagenesis, as well as synthetically derived sequences. A substantially similar promoter sequence of the present disclosure also generally refers to those fragments of a particular promoter nucleotide sequence disclosed herein that operate to promote the constitutive expression of an operably linked heterologous nucleic acid fragment. These promoter fragments comprise at least about 20 contiguous nucleotides, at least about 50 contiguous nucleotides, at least about 75 contiguous nucleotides, at least about 100 contiguous nucleotides of the particular promoter nucleotide sequence disclosed herein or a sequence that is at least 95 to about 99% identical to such contiguous sequences. The nucleotides of such fragments will usually include the TATA recognition sequence (or CAAT box or a CCAAT) of the particular promoter sequence. Such fragments may be obtained by use of restriction enzymes to cleave the naturally occurring promoter nucleotide sequences disclosed herein; by synthesizing a nucleotide sequence from the naturally occurring promoter DNA sequence; or may be obtained through the use of PCR technology. Variants of these promoter fragments, such as those resulting from site-directed mutagenesis, are encompassed by the compositions of the present disclosure.

Provided are sequences which contain one or more degenerate codons to those provided in the sequence listing. "Codon degeneracy" generally refers to divergence in the genetic code permitting variation of the nucleotide sequence without affecting the amino acid sequence of an encoded polypeptide. Accordingly, the instant disclosure relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

Sequence alignments and percent identity calculations may be determined using a variety of comparison methods designed to detect similar or identical sequences including, but not limited to, the MEGALIGN® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp (1989) *CABIOS.* 5:151-153) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Alternatively, the Clustal W method of alignment may be used. The Clustal W method of alignment (described by Higgins and Sharp, *CABIOS.* 5:151-153 (1989); Higgins, D. G. et al., *Comput. Appl. Biosci.* 8:189-191 (1992)) can be found in the MegAlign™ v 6.1 program of the LASERGENE® bioinformatics computing suite (DNASTAR® Inc., Madison, Wis.). Default parameters for multiple alignment correspond to GAP PENALTY=10, GAP LENGTH PENALTY=0.2, Delay Divergent Sequences=30%, DNA Transition Weight=0.5, Protein Weight Matrix=Gonnet Series, DNA Weight Matrix=IUB. For pairwise alignments the default parameters are Alignment=Slow-Accurate, Gap Penalty=10.0, Gap Length=0.10, Protein Weight Matrix=Gonnet 250 and DNA Weight Matrix=IUB. After alignment of the sequences using the Clustal W program, it is possible to obtain "percent identity" and "divergence" values by viewing the "sequence distances" table in the same program.

In one embodiment the % sequence identity is determined over the entire length of the molecule (nucleotide or amino acid). A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Altschul, S. F. et al., J. Mol. Biol. 215:403-410 (1993)) and Gapped Blast (Altschul, S. F. et al., Nucleic Acids Res. 25:3389-3402 (1997)). BLASTN generally refers to a BLAST program that compares a nucleotide query sequence against a nucleotide sequence database.

The present disclosure provides genes, mutated genes, modified genes, chimeric genes and recombinant expression constructs. "Gene" includes a nucleic acid fragment that expresses a functional molecule such as, but not limited to, a specific protein, including regulatory sequences preceding (5' non-coding sequences) and following (3' non-coding sequences) the coding sequence. "Native gene" generally refers to a gene as found in nature with its own regulatory sequences.

A "mutated gene" or "modified gene" is a gene that has been altered through human intervention. Such a "mutated gene" or "modified gene" has a sequence that differs from the sequence of the corresponding non-mutated gene by at least one nucleotide addition, deletion, or substitution. In certain embodiments of the disclosure, the mutated gene comprises an alteration that results from a guide polynucleotide/Cas endonuclease system as disclosed herein. A mutated or modified plant is a plant comprising a mutated or modified gene.

"Chimeric gene" or "recombinant expression construct", which are used interchangeably, includes any gene that is not a native gene, comprising regulatory and coding sequences that are not found together in nature. Accordingly, a chimeric gene may comprise regulatory sequences and coding sequences that are derived from different sources.

A "mutated polynucleotide" or "modified polynucleotide" is a polynucleotide that has been altered through human intervention. Such a "mutated polynucleotide" or "modified polynucleotide" has a sequence that differs from the sequence of the corresponding non-mutated or modified polypeptide by at least one nucleotide addition, deletion, or substitution. In certain embodiments of the disclosure, the mutated polynucleotide comprises an alteration that results from a guide polynucleotide/Cas endonuclease system as disclosed herein. A mutated or modified plant is a plant comprising a mutated or modified polynucleotide.

"Coding sequence" generally refers to a polynucleotide sequence which codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

An "intron" is an intervening sequence in a gene that is transcribed into RNA but is then excised in the process of generating the mature mRNA. The term is also used for the excised RNA sequences. An "exon" is a portion of the sequence of a gene that is transcribed and is found in the mature messenger RNA derived from the gene, but is not necessarily a part of the sequence that encodes the final gene product.

The 5' untranslated region (5'UTR) (also known as a translational leader sequence or leader RNA) is the region of an mRNA that is directly upstream from the initiation codon. This region is involved in the regulation of translation of a transcript by differing mechanisms in viruses, prokaryotes and eukaryotes.

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"RNA transcript" generally refers to a product resulting from RNA polymerase-catalyzed transcription of a DNA sequence. When an RNA transcript is a perfect complimentary copy of a DNA sequence, it is referred to as a primary transcript or it may be a RNA sequence derived from posttranscriptional processing of a primary transcript and is referred to as a mature RNA. "Messenger RNA" ("mRNA") generally refers to RNA that is without introns and that can be translated into protein by the cell. "cDNA" generally refers to a DNA that is complementary to and synthesized from an mRNA template using the enzyme reverse transcriptase. The cDNA can be single-stranded or converted into the double-stranded by using the Klenow fragment of DNA polymerase. "Sense" RNA generally refers to RNA transcript that includes mRNA and so can be translated into protein within a cell or in vitro. "Antisense RNA" generally refers to a RNA transcript that is complementary to all or part of a target primary transcript or mRNA and that blocks expression or transcripts accumulation of a target gene. The complementarity of an antisense RNA may be with any part of the specific gene transcript, i.e. at the 5' non-coding sequence, 3' non-coding sequence, introns, or the coding sequence. "Functional RNA" generally refers to antisense RNA, ribozyme RNA, or other RNA that may not be translated but yet has an effect on cellular processes.

The term "operably linked" or "functionally linked" generally refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The terms "initiate transcription", "initiate expression", "drive transcription", and "drive expression" are used interchangeably herein and all refer to the primary function of a promoter. As detailed throughout this disclosure, a promoter is a non-coding genomic DNA sequence, usually upstream (5) to the relevant coding sequence, and its primary function is to act as a binding site for RNA polymerase and initiate transcription by the RNA polymerase. Additionally, there is "expression" of RNA, including functional RNA, or the expression of polypeptide for operably linked encoding nucleotide sequences, as the transcribed RNA ultimately is translated into the corresponding polypeptide.

The term "expression", as used herein, generally refers to the production of a functional end-product e.g., an mRNA or a protein (precursor or mature).

The term "expression cassette" as used herein, generally refers to a discrete nucleic acid fragment into which a nucleic acid sequence or fragment can be cloned or synthesized through molecular biology techniques.

Expression or overexpression of a gene involves transcription of the gene and translation of the mRNA into a precursor or mature protein. "Antisense inhibition" generally refers to the production of antisense RNA transcripts capable of suppressing the expression of the target protein. "Overexpression" generally refers to the production of a gene product in transgenic organisms that exceeds levels of production in normal or non-transformed organisms. "Co-suppression" generally refers to the production of sense RNA transcripts capable of suppressing the expression or transcript accumulation of identical or substantially similar foreign or endogenous genes (U.S. Pat. No. 5,231,020). The mechanism of co-suppression may be at the DNA level (such as DNA methylation), at the transcriptional level, or at post-transcriptional level.

As stated herein, "suppression" includes a reduction of the level of enzyme activity or protein functionality (e.g., a phenotype associated with a protein) detectable in a transgenic plant when compared to the level of enzyme activity or protein functionality detectable in a non-transgenic or wild type plant with the native enzyme or protein. The level of enzyme activity in a plant with the native enzyme is referred to herein as "wild type" activity. The level of protein functionality in a plant with the native protein is referred to herein as "wild type" functionality. The term "suppression" includes lower, reduce, decline, decrease, inhibit, eliminate and prevent. This reduction may be due to a decrease in translation of the native mRNA into an active enzyme or functional protein. It may also be due to the transcription of the native DNA into decreased amounts of mRNA and/or to rapid degradation of the native mRNA. The term "native enzyme" generally refers to an enzyme that is produced naturally in a non-transgenic or wild type cell. The terms "non-transgenic" and "wild type" are used interchangeably herein.

"Altering expression" or "modulating expression" generally refers to the production of gene product(s) in plants in amounts or proportions that differ significantly from the amount of the gene product(s) produced by the corresponding wild-type plants (i.e., expression is increased or decreased).

"Transformation" as used herein generally refers to both stable transformation and transient transformation.

"Stable transformation" generally refers to the introduction of a nucleic acid fragment into a genome of a host organism resulting in genetically stable inheritance. Once stably transformed, the nucleic acid fragment is stably integrated in the genome of the host organism and any subsequent generation. Host organisms containing the transformed nucleic acid fragments are referred to as "transgenic" organisms.

"Transient transformation" generally refers to the introduction of a nucleic acid fragment into the nucleus, or DNA-containing organelle, of a host organism resulting in gene expression without genetically stable inheritance.

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

"Genome" as it applies to plant cells encompasses not only chromosomal DNA found within the nucleus, but organelle DNA found within subcellular components (e.g., mitochondrial, plastid) of the cell.

"Genetic modification" generally refers to modification of any nucleic acid sequence or genetic element by insertion, deletion, or substitution of one or more nucleotides in an endogenous nucleotide sequence by genome editing or by insertion of a recombinant nucleic acid, e.g., as part of a vector or construct in any region of the plant genomic DNA by routine transformation techniques. Examples of modification of genetic components include, but are not limited to, polypeptide coding sequences, promoter regions, 5' untranslated leaders, introns, genes, 3' untranslated regions, and other regulatory sequences or sequences that affect transcription or translation of one or more nucleic acid sequences.

In an embodiment the seeds, such as soybean seeds, have an increased oil or fatty acid content as described herein, and optionally modified amounts of fatty acids, such as at least a 5%, 10%, 15%, 20%, 25%, 30%, 40%, or 50% increase in oleic acid content expressed by weight as a proportion of the total fatty acid content as described herein. The seeds, such a soybean seeds may have an increased protein content of at least 1%, 2%, 3%, 4%, 5%, 6%, 7%, 8%, 9%, 10%, 15%, 20% or 25% by weight.

In an embodiment, this disclosure concerns host cells comprising either the recombinant DNA constructs of the disclosure as described herein or isolated polynucleotides of the disclosure as described herein. Examples of host cells which can be used to practice the disclosure include, but are not limited to, yeast, bacteria, and plants.

Plasmid vectors comprising the instant recombinant DNA construct can be constructed. The choice of plasmid vector is dependent upon the method that will be used to transform host cells. The skilled artisan is well aware of the genetic elements that must be present on the plasmid vector in order to successfully transform, select and propagate host cells containing the chimeric gene.

I. Gene Editing

In some embodiments, gene editing may be facilitated through the induction of a double-stranded break (DSB) or single-strand break, in a defined position in the genome near the desired alteration. DSBs can be induced using any DSB-inducing agent available, including, but not limited to, TALENs, meganucleases, zinc finger nucleases, Cas9-gRNA systems (based on bacterial CRISPR-Cas systems), guided cpf1 endonuclease systems, and the like. In some embodiments, the introduction of a DSB can be combined with the introduction of a polynucleotide modification template.

A polynucleotide modification template can be introduced into a cell by any method known in the art, such as, but not limited to, transient introduction methods, transfection, electroporation, microinjection, particle mediated delivery, topical application, whiskers mediated delivery, delivery via cell-penetrating peptides, or mesoporous silica nanoparticle (MSN)-mediated direct delivery.

The polynucleotide modification template can be introduced into a cell as a single stranded polynucleotide molecule, a double stranded polynucleotide molecule, or as part of a circular DNA (vector DNA). The polynucleotide modification template can also be tethered to the guide RNA and/or the Cas endonuclease. Tethered DNAs can allow for co-localizing target and template DNA, useful in genome editing and targeted genome regulation, and can also be useful in targeting post-mitotic cells where function of endogenous HR machinery is expected to be highly diminished (Mali et al. 2013 *Nature Methods* Vol. 10: 957-963.) The polynucleotide modification template may be present transiently in the cell or it can be introduced via a viral replicon.

A "modified nucleotide" or "edited nucleotide" refers to a nucleotide sequence of interest that comprises at least one alteration when compared to its non-modified nucleotide sequence. Such "alterations" include, for example: (i) replacement of at least one nucleotide, (ii) a deletion of at least one nucleotide, (iii) an insertion of at least one nucleotide, or (iv) any combination of (i)-(iii).

The term "polynucleotide modification template" includes a polynucleotide that comprises at least one nucleotide modification when compared to the nucleotide sequence to be edited. A nucleotide modification can be at least one nucleotide substitution, addition or deletion. Optionally, the polynucleotide modification template can further comprise homologous nucleotide sequences flanking the at least one nucleotide modification, wherein the flanking homologous nucleotide sequences provide sufficient homology to the desired nucleotide sequence to be edited.

The process for editing a genomic sequence combining DSB and modification templates generally comprises: providing to a host cell, a DSB-inducing agent, or a nucleic acid encoding a DSB-inducing agent, that recognizes a target sequence in the chromosomal sequence and is able to induce a DSB in the genomic sequence, and at least one polynucleotide modification template comprising at least one nucleotide alteration when compared to the nucleotide sequence to be edited. The polynucleotide modification template can further comprise nucleotide sequences flanking the at least one nucleotide alteration, in which the flanking sequences are substantially homologous to the chromosomal region flanking the DSB.

The endonuclease can be provided to a cell by any method known in the art, for example, but not limited to transient introduction methods, transfection, microinjection, and/or topical application or indirectly via recombination constructs. The endonuclease can be provided as a protein or as a guided polynucleotide complex directly to a cell or indirectly via recombination constructs. The endonuclease can be introduced into a cell transiently or can be incorporated into the genome of the host cell using any method known in the art. In the case of a CRISPR-Cas system, uptake of the endonuclease and/or the guided polynucleotide into the cell can be facilitated with a Cell Penetrating Peptide (CPP) as described in WO2016073433 published May 12, 2016.

As used herein, a "genomic region" is a segment of a chromosome in the genome of a cell that is present on either side of the target site or, alternatively, also comprises a portion of the target site. The genomic region can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800. 5-2900, 5-3000, 5-3100 or more bases such that the genomic region has sufficient homology to undergo homologous recombination with the corresponding region of homology.

TAL effector nucleases (TALEN) are a class of sequence-specific nucleases that can be used to make double-strand breaks at specific target sequences in the genome of a plant or other organism. (Miller et al. (2011) Nature Biotechnology 29:143-148).

Endonucleases are enzymes that cleave the phosphodiester bond within a polynucleotide chain. Endonucleases include restriction endonucleases, which cleave DNA at specific sites without damaging the bases, and meganucleases, also known as homing endonucleases (HEases), which like restriction endonucleases, bind and cut at a specific recognition site, however the recognition sites for meganucleases are typically longer, about 18 bp or more (patent application PCT/US12/30061, filed on Mar. 22, 2012). Meganucleases have been classified into four families based on conserved sequence motifs, the families are the LAGLIDADG, GIY-YIG, H-N-H, and His-Cys box families. These motifs participate in the coordination of metal ions and hydrolysis of phosphodiester bonds. HEases are notable for their long recognition sites, and for tolerating some sequence polymorphisms in their DNA substrates. The naming convention for meganuclease is similar to the convention for other restriction endonuclease. Meganucleases are also characterized by prefix F-, I-, or PI- for enzymes encoded by free-standing ORFs, introns, and inteins, respectively. One step in the recombination process involves polynucleotide cleavage at or near the recognition site. The cleaving activity can be used to produce a double-strand break. For reviews of site-specific recombinases and their recognition sites, see, Sauer (1994) Curr Op Biotechnol 5:521-7; and Sadowski (1993) FASEB 7:760-7. In some examples the recombinase is from the Integrase or Resolvase families.

Zinc finger nucleases (ZFNs) are engineered double-strand break inducing agents comprised of a zinc finger DNA binding domain and a double-strand-break-inducing agent domain. Recognition site specificity is conferred by the zinc finger domain, which typically comprising two, three, or four zinc fingers, for example having a C2H2 structure, however other zinc finger structures are known and have been engineered. Zinc finger domains are amenable for designing polypeptides which specifically bind a selected polynucleotide recognition sequence. ZFNs include an engineered DNA-binding zinc finger domain linked to a non-specific endonuclease domain, for example nuclease domain from a Type IIs endonuclease such as FokI. Additional functionalities can be fused to the zinc-finger binding domain, including transcriptional activator domains, transcription repressor domains, and methylases. In some examples, dimerization of nuclease domain is required for cleavage activity. Each zinc finger recognizes three consecutive base pairs in the target DNA. For example, a 3 finger domain recognized a sequence of 9 contiguous nucleotides, with a dimerization requirement of the nuclease, two sets of zinc finger triplets are used to bind an 18 nucleotide recognition sequence.

Genome editing using DSB-inducing agents, such as Cas9-gRNA complexes, has been described, for example in U.S. Patent Application US 2015-0082478 A1, published on Mar. 19, 2015, WO2015/026886 A1, published on Feb. 26, 2015, WO2016007347, published on Jan. 14, 2016, and WO201625131, published on Feb. 18, 2016, all of which are incorporated by reference herein.

The term "Cas gene" herein refers to a gene that is generally coupled, associated or close to, or in the vicinity of flanking CRISPR loci in bacterial systems. The terms "Cas gene", "CRISPR-associated (Cas) gene" are used interchangeably herein. The term "Cas endonuclease" herein refers to a protein encoded by a Cas gene. A Cas endonuclease herein, when in complex with a suitable polynucleotide component, is capable of recognizing, binding to, and optionally nicking or cleaving all or part of a specific DNA target sequence. A Cas endonuclease described herein comprises one or more nuclease domains. Cas endonucleases of the disclosure includes those having a HNH or HNH-like nuclease domain and/or a RuvC or RuvC-like nuclease domain. A Cas endonuclease of the disclosure includes a Cas9 protein, a Cpf1 protein, a C2c1 protein, a C2c2 protein, a C2c3 protein, Cas3, Cas 5, Cas7, Cas8, Cas10, or complexes of these.

As used herein, the terms "guide polynucleotide/Cas endonuclease complex", "guide polynucleotide/Cas endonuclease system", "guide polynucleotide/Cas complex", "guide polynucleotide/Cas system", "guided Cas system" are used interchangeably herein and refer to at least one guide polynucleotide and at least one Cas endonuclease that are capable of forming a complex, wherein the guide polynucleotide/Cas endonuclease complex can direct the Cas endonuclease to a DNA target site, enabling the Cas endonuclease to recognize, bind to, and optionally nick or cleave (introduce a single or double strand break) the DNA target site. A guide polynucleotide/Cas endonuclease complex herein can comprise Cas protein(s) and suitable polynucleotide component(s) of any of the four known CRISPR systems (Horvath and Barrangou, 2010, *Science* 327:167-170) such as a type I, II, or III CRISPR system. A Cas endonuclease unwinds the DNA duplex at the target sequence and optionally cleaves at least one DNA strand, as mediated by recognition of the target sequence by a polynucleotide (such as, but not limited to, a crRNA or guide RNA) that is in complex with the Cas protein. Such recognition and cutting of a target sequence by a Cas endonuclease typically occurs if the correct protospacer-adjacent motif (PAM) is located at or adjacent to the 3' end of the DNA target sequence. Alternatively, a Cas protein herein may lack DNA cleavage or nicking activity, but can still specifically bind to a DNA target sequence when complexed with a suitable RNA component. (See also U.S. Patent Application US 2015-0082478 A1, published on Mar. 19, 2015 and US 2015-0059010 A1, published on Feb. 26, 2015, both are hereby incorporated in its entirety by reference).

A guide polynucleotide/Cas endonuclease complex can cleave one or both strands of a DNA target sequence. A guide polynucleotide/Cas endonuclease complex that can cleave both strands of a DNA target sequence typically comprise a Cas protein that has all of its endonuclease domains in a functional state (e.g., wild type endonuclease domains or variants thereof retaining some or all activity in each endonuclease domain). Non-limiting examples of Cas9 nickases suitable for use herein are disclosed in U.S. Patent Appl. Publ. No. 2014/0189896, which is incorporated herein by reference.

Other Cas endonuclease systems have been described in PCT patent applications PCT/US16/32073, filed May 12, 2016 and PCT/US16/32028 filed May 12, 2016, both applications incorporated herein by reference.

"Cas9" (formerly referred to as Cas5, Csn1, or Csx12) herein refers to a Cas endonuclease of a type II CRISPR system that forms a complex with a crNucleotide and a tracrNucleotide, or with a single guide polynucleotide, for specifically recognizing and cleaving all or part of a DNA target sequence. Cas9 protein comprises a RuvC nuclease domain and an HNH (H-N-H) nuclease domain, each of which can cleave a single DNA strand at a target sequence (the concerted action of both domains leads to DNA double-strand cleavage, whereas activity of one domain leads to a nick). In general, the RuvC domain comprises subdomains 1, and Ill, where domain I is located near the N-terminus of Cas9 and subdomains II and III are located in the middle of the protein, flanking the HNH domain (Hsu et al, Cell 157:1262-1278). A type CRISPR system includes a DNA cleavage system utilizing a Cas9 endonuclease in complex with at least one polynucleotide component. For example, a Cas9 can be in complex with a CRISPR RNA (crRNA) and a trans-activating CRISPR RNA (tracrRNA). In another example, a Cas9 can be in complex with a single guide RNA.

Any guided endonuclease can be used in the methods disclosed herein. Such endonucleases include, but are not limited to Cas9 and Cpf1 endonucleases. Many endonucleases have been described to date that can recognize specific PAM sequences (see for example—Jinek et al. (2012) Science 337 p 816-821, PCT patent applications PCT/US16/32073, filed May 12, 2016 and PCT/US16/32028 filed May 12, 2016 and Zetsche B et al. 2015. Cell 163, 1013) and cleave the target DNA at a specific position. It is understood that based on the methods and embodiments described herein utilizing a guided Cas system one can now tailor these methods such that they can utilize any guided endonuclease system.

The guide polynucleotide can also be a single molecule (also referred to as single guide polynucleotide) comprising a crNucleotide sequence linked to a tracrNucleotide sequence. The single guide polynucleotide comprises a first nucleotide sequence domain (referred to as Variable Targeting domain or VT domain) that can hybridize to a nucleotide sequence in a target DNA and a Cas endonuclease recognition domain (CER domain), that interacts with a Cas endonuclease polypeptide. By "domain" it is meant a contiguous stretch of nucleotides that can be RNA, DNA, and/or RNA-DNA-combination sequence. The VT domain and/or the CER domain of a single guide polynucleotide can comprise a RNA sequence, a DNA sequence, or a RNA-DNA-combination sequence. The single guide polynucleotide being comprised of sequences from the crNucleotide and the tracrNucleotide may be referred to as "single guide RNA" (when composed of a contiguous stretch of RNA nucleotides) or "single guide DNA" (when composed of a contiguous stretch of DNA nucleotides) or "single guide RNA-DNA" (when composed of a combination of RNA and DNA nucleotides). The single guide polynucleotide can form a complex with a Cas endonuclease, wherein the guide polynucleotide/Cas endonuclease complex (also referred to as a guide polynucleotide/Cas endonuclease system) can direct the Cas endonuclease to a genomic target site, enabling the Cas endonuclease to recognize, bind to, and optionally nick or cleave (introduce a single or double strand break) the target site. (See also U.S. Patent Application US 2015-0082478 A1, published on Mar. 19, 2015 and US 2015-0059010 A1, published on Feb. 26, 2015, both are hereby incorporated in its entirety by reference.)

The term "variable targeting domain" or "VT domain" is used interchangeably herein and includes a nucleotide sequence that can hybridize (is complementary) to one strand (nucleotide sequence) of a double strand DNA target site. In some embodiments, the variable targeting domain comprises a contiguous stretch of 12 to 30 nucleotides. The variable targeting domain can be composed of a DNA sequence, a RNA sequence, a modified DNA sequence, a modified RNA sequence, or any combination thereof.

The terms "single guide RNA" and "sgRNA" are used interchangeably herein and relate to a synthetic fusion of two RNA molecules, a crRNA (CRISPR RNA) comprising a variable targeting domain (linked to a tracr mate sequence that hybridizes to a tracrRNA), fused to a tracrRNA (trans-activating CRISPR RNA). The single guide RNA can comprise a crRNA or crRNA fragment and a tracrRNA or tracrRNA fragment of the type II CRISPR/Cas system that can form a complex with a type II Cas endonuclease, wherein the guide RNA/Cas endonuclease complex can direct the Cas endonuclease to a DNA target site, enabling the Cas endonuclease to recognize, bind to, and optionally nick or cleave (introduce a single or double strand break) the DNA target site.

The terms "guide RNA/Cas endonuclease complex", "guide RNA/Cas endonuclease system", "guide RNA/Cas complex", "guide RNA/Cas system", "gRNA/Cas complex", "gRNA/Cas system", "RNA-guided endonuclease", "RGEN" are used interchangeably herein and refer to at least one RNA component and at least one Cas endonuclease that are capable of forming a complex, wherein the guide RNA/Cas endonuclease complex can direct the Cas endonuclease to a DNA target site, enabling the Cas endonuclease to recognize, bind to, and optionally nick or cleave (introduce a single or double strand break) the DNA target site. A guide RNA/Cas endonuclease complex herein can comprise Cas protein(s) and suitable RNA component(s) of any of the four known CRISPR systems (Horvath and Barrangou, 2010, Science 327:167-170) such as a type I, II, or III CRISPR system. A guide RNA/Cas endonuclease complex can comprise a Type II Cas9 endonuclease and at least one RNA component (e.g., a crRNA and tracrRNA, or a gRNA). (See also U.S. Patent Application US 2015-0082478 A1, published on Mar. 19, 2015 and US 2015-0059010 A1, published on Feb. 26, 2015, both are hereby incorporated in its entirety by reference).

The guide polynucleotide can be introduced into a cell transiently, as single stranded polynucleotide or a double stranded polynucleotide, using any method known in the art such as, but not limited to, particle bombardment, *Agrobacterium* transformation or topical applications. The guide polynucleotide can also be introduced indirectly into a cell by introducing a recombinant DNA molecule (via methods such as, but not limited to, particle bombardment or *Agrobacterium* transformation) comprising a heterologous nucleic acid fragment encoding a guide polynucleotide, operably linked to a specific promoter that is capable of transcribing the guide RNA in the cell. The specific promoter can be, but is not limited to, a RNA polymerase III promoter, which allow for transcription of RNA with precisely defined, unmodified, 5'- and 3'-ends (DiCarlo et al., Nucleic Acids Res. 41: 4336-4343; Ma et al., Mol. Ther. Nucleic Acids 3:e161) as described in WO2016025131, published on Feb. 18, 2016, incorporated herein in its entirety by reference.

The terms "target site", "target sequence", "target site sequence, "target DNA", "target locus", "genomic target site", "genomic target sequence", "genomic target locus" and "protospacer", are used interchangeably herein and refer to a polynucleotide sequence such as, but not limited to, a nucleotide sequence on a chromosome, episome, or any other DNA molecule in the genome (including chromosomal, chloroplastic, mitochondrial DNA, plasmid DNA) of a cell, at which a guide polynucleotide/Cas endonuclease complex can recognize, bind to, and optionally nick or cleave. The target site can be an endogenous site in the genome of a cell, or alternatively, the target site can be heterologous to the cell and thereby not be naturally occurring in the genome of the cell, or the target site can be found in a heterologous genomic location compared to where it occurs in nature. As used herein, terms "endogenous target sequence" and "native target sequence" are used interchangeable herein to refer to a target sequence that is endogenous or native to the genome of a cell and is at the endogenous or native position of that target sequence in the genome of the cell. Cells include, but are not limited to, human, non-human, animal, bacterial, fungal, insect, yeast, non-conventional yeast, and plant cells as well as plants and seeds produced by the methods described herein. An "artificial target site" or "artificial target sequence" are used interchangeably herein and refer to a target sequence that has been introduced into the genome of a cell. Such an artificial target sequence can be identical in sequence to an endogenous or native target sequence in the genome of a cell but be located in a different position (i.e., a non-endogenous or non-native position) in the genome of a cell.

Provided are plants and seeds which contain an altered or modified target site or sequence. An "altered target site", "altered target sequence", "modified target site", "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

Methods for "modifying a target site" and "altering a target site" are used interchangeably herein and refer to methods for producing an altered target site.

The length of the target DNA sequence (target site) can vary, and includes, for example, target sites that are at least 12, 13, 14, 15, 16, 17, 18, 19, 20, 21, 22, 23, 24, 25, 26, 27, 28, 29, 30 or more nucleotides in length. It is further possible that the target site can be palindromic, that is, the sequence on one strand reads the same in the opposite direction on the complementary strand. The nick/cleavage site can be within the target sequence or the nick/cleavage site could be outside of the target sequence. In another variation, the cleavage could occur at nucleotide positions immediately opposite each other to produce a blunt end cut or, in other Cases, the incisions could be staggered to produce single-stranded overhangs, also called "sticky ends", which can be either 5' overhangs, or 3' overhangs. Active variants of genomic target sites can also be used. Such active variants can comprise at least 65%, 70%, 75%, 80%, 85%, 90%, 91%, 92%, 93%, 94%, 95%, 96%, 97%, 98%, 99% or more sequence identity to the given target site, wherein the active variants retain biological activity and hence are capable of being recognized and cleaved by an Cas endonuclease. Assays to measure the single or double-strand break of a target site by an endonuclease are known in the art and generally measure the overall activity and specificity of the agent on DNA substrates containing recognition sites.

A "protospacer adjacent motif" (PAM) herein refers to a short nucleotide sequence adjacent to a target sequence (protospacer) that is recognized (targeted) by a guide polynucleotide/Cas endonuclease system described herein. The Cas endonuclease may not successfully recognize a target DNA sequence if the target DNA sequence is not followed by a PAM sequence. The sequence and length of a PAM herein can differ depending on the Cas protein or Cas protein complex used. The PAM sequence can be of any length but is typically 1, 2, 3, 4, 5, 6, 7, 8, 9, 10, 11, 12, 13, 14, 15, 16, 17, 18, 19 or 20 nucleotides long.

The terms "targeting", "gene targeting" and "DNA targeting" are used interchangeably herein. DNA targeting herein may be the specific introduction of a knock-out, edit, or knock-in at a particular DNA sequence, such as in a chromosome or plasmid of a cell. In general, DNA targeting can be performed herein by cleaving one or both strands at a specific DNA sequence in a cell with an endonuclease associated with a suitable polynucleotide component. Such DNA cleavage, if a double-strand break (DSB), can prompt NHEJ or HDR processes which can lead to modifications at the target site.

Methods to modify or alter endogenous genomic DNA are known in the art. In some aspects, methods and compositions are provided for modifying naturally-occurring polynucleotides or integrated transgenic sequences, including regulatory elements, coding sequences, and non-coding sequences. These methods and compositions are also useful in targeting nucleic acids to pre-engineered target recognition sequences in the genome. Modification of polynucleotides may be accomplished, for example, by introducing single- or double-strand breaks into the DNA molecule.

Double-strand breaks induced by double-strand-break-inducing agents, such as endonucleases that cleave the phosphodiester bond within a polynucleotide chain, can result in the induction of DNA repair mechanisms, including the non-homologous end-joining pathway, and homologous recombination. Endonucleases include a range of different enzymes, including restriction endonucleases (see e.g. Roberts et al., (2003) Nucleic Acids Res 1:418-20), Roberts et al., (2003) Nucleic Acids Res 31:1805-12, and Belfort et al., (2002) in Mobile DNA II, pp. 761-783, Eds. Craigie et al., (ASM Press, Washington, D.C.)), meganucleases (see e.g., WO 2009/114321; Gao et al. (2010) Plant Journal 1:176-187), TAL effector nucleases or TALENs (see e.g., US20110145940, Christian, M., T. Cermak, et al. 2010. Targeting DNA double-strand breaks with TAL effector nucleases. Genetics 186(2): 757-61 and Boch et al., (2009), Science 326(5959): 1509-12), zinc finger nucleases (see e.g. Kim, Y. G., J. Cha, et al. (1996). "Hybrid restriction enzymes: zinc finger fusions to FokI cleavage"), and CRISPR-Cas endonucleases (see e.g. WO2007/025097 application published Mar. 1, 2007).

Once a double-strand break is induced in the genome, cellular DNA repair mechanisms are activated to repair the break. There are two DNA repair pathways. One is termed nonhomologous end-joining (NHEJ) pathway (Bleuyard et al., (2006) *DNA Repair* 5:1-12) and the other is homology-directed repair (HDR). The structural integrity of chromosomes is typically preserved by NHEJ, but deletions, insertions, or other rearrangements (such as chromosomal translocations) are possible (Siebert and Puchta, 2002, *Plant Cell* 14:1121-31; Pacher et al., 2007, Genetics 175:21-9. The HDR pathway is another cellular mechanism to repair double-stranded DNA breaks, and includes homologous recombination (HR) and single-strand annealing (SSA) (Lieber. 2010 *Annu. Rev. Biochem.* 79:181-211).

In addition to the double-strand break inducing agents, site-specific base conversions can also be achieved to engineer one or more nucleotide changes to create one or more EMEs described herein into the genome. These include for example, a site-specific base edit mediated by an C•G to T•A or an A•T to G•C base editing deaminase enzymes (Gaudelli et al., Programmable base editing of A•T to G•C in genomic DNA without DNA cleavage." Nature (2017); Nishida et al. "Targeted nucleotide editing using hybrid prokaryotic and vertebrate adaptive immune systems." Science 353 (6305) (2016); Komor et al. "Programmable editing of a target base in genomic DNA without double-stranded DNA cleavage." Nature 533 (7603) (2016):420-4.

A targeting method herein can be performed in such a way that two or more DNA target sites are targeted in the method, for example. Such a method can optionally be characterized as a multiplex method. Two, three, four, five, six, seven, eight, nine, ten, or more target sites can be targeted at the same time in certain embodiments. A multiplex method is typically performed by a targeting method herein in which multiple different RNA components are provided, each designed to guide a guide polynucleotide/Cas endonuclease complex to a unique DNA target site.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

Provided are plants which are dicots. The terms "dicot" and "dicotyledonous plant" are used interchangeably herein.

A dicot of the current disclosure includes the following families: Brassicaceae, Leguminosae, and Solanaceae.

Progeny plants are provided. "Progeny" comprises any subsequent generation of a plant, and can include F1 progeny, F2 progeny F3 progeny and so on.

The heterologous polynucleotide can be stably integrated within the genome such that the polynucleotide is passed on to successive generations. The heterologous polynucleotide may be integrated into the genome alone or as part of a recombinant DNA construct. The alterations of the genome (chromosomal or extra-chromosomal) by conventional plant breeding methods, by genome editing procedures that do not result in an insertion of a foreign polynucleotide, or by naturally occurring events such as random cross-fertilization, non-recombinant viral infection, non-recombinant bacterial transformation, non-recombinant transposition, or spontaneous mutation are also methods of modifying a host genome.

"Transient expression" generally refers to the temporary expression of often reporter genes such as β-glucuronidase (GUS), fluorescent protein genes ZS-GREEN1, ZS-YELLOW1 N1, AM-CYAN1, DS-RED in selected certain cell types of the host organism in which the transgenic gene is introduced temporally by a transformation method. The transformed materials of the host organism are subsequently discarded after the transient gene expression assay.

Standard recombinant DNA and molecular cloning techniques used herein are well known in the art and are described more fully in Sambrook, J. et al., In Molecular Cloning: A Laboratory Manual; 2$^{nd}$ ed.; Cold Spring Harbor Laboratory Press: Cold Spring Harbor, N.Y., 1989 (hereinafter "Sambrook et al., 1989") or Ausubel, F. M., Brent, R., Kingston, R. E., Moore, D. D., Seidman, J. G., Smith, J. A. and Struhl, K., Eds.; In Current Protocols in Molecular Biology; John Wiley and Sons: New York, 1990 (hereinafter "Ausubel et al., 1990").

"PCR" or "Polymerase Chain Reaction" is a technique for the synthesis of large quantities of specific DNA segments, consisting of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps comprises a cycle.

Provided are plasmids, vectors and cassettes which contain one or more of the sequences provided, including any combination of sequence components disclosed in the Examples. The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

Provided are recombinant DNA constructs or recombinant expression constructs which contain the sequences disclosed herein, including any combination of sequence components disclosed in the Examples. The term "recombinant DNA construct" or "recombinant expression construct" is used interchangeably and generally refers to a discrete polynucleotide into which a nucleic acid sequence or fragment can be moved. Preferably, it is a plasmid vector or a fragment thereof comprising the promoters of the present disclosure. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., EMBO J. 4:2411-2418 (1985); De Almeida et al., Mol. Gen. Genetics 218:78-86 (1989)), and thus that multiple events must be screened in order to obtain lines displaying the desired expression level and pattern. Such screening may be accomplished by PCR and Southern analysis of DNA, RT-PCR and Northern analysis of mRNA expression, Western analysis of protein expression, or phenotypic analysis.

Further uses for guide RNA/Cas endonuclease systems have been described (See U.S. Patent Application US 2015-0082478 A1, published on Mar. 19, 2015, WO2015/026886 A1, published on Feb. 26, 2015, US 2015-0059010 A1, published on Feb. 26, 2015, US application publication 2017-0306349, filed on Jul. 7, 2014, and US application publication 2017-0226533, filed on Aug. 13, 2014, all of which are incorporated by reference herein) and include but are not limited to modifying or replacing nucleotide sequences of interest (such as a regulatory elements), insertion of polynucleotides of interest, gene knock-out, gene-knock in, modification of splicing sites and/or introducing alternate splicing sites, modifications of nucleotide sequences encoding a protein of interest, amino acid and/or protein fusions, and gene silencing by expressing an inverted repeat into a gene of interest.

Methods for transforming dicots, primarily by use of *Agrobacterium tumefaciens*, and obtaining transgenic plants have been published, among others, for cotton (U.S. Pat. Nos. 5,004,863, 5,159,135); soybean (U.S. Pat. Nos. 5,569,834, 5,416,011); *Brassica* (U.S. Pat. No. 5,463,174); peanut (Cheng et al., Plant Cell Rep. 15:653-657 (1996), McKently et al., Plant Cell Rep. 14:699-703 (1995)); *papaya* (Ling et al., Bio/technology 9:752-758 (1991)); and pea (Grant et al., Plant Cell Rep. 15:254-258 (1995)). For a review of other commonly used methods of plant transformation see Newell, C. A., Mol. Biotechnol. 16:53-65 (2000). One of these methods of transformation uses *Agrobacterium rhizogenes* (Tepfler, M. and Casse-Delbart, F., Microbiol. Sci. 4:24-28 (1987)). Transformation of soybeans using direct delivery of DNA has been published using PEG fusion (PCT Publication No. WO 92/17598), electroporation (Chowrira et al., Mol. Biotechnol. 3:17-23 (1995); Christou et al., Proc. Natl. Acad. Sci. U.S.A. 84:3962-3966 (1987)), microinjection, or particle bombardment (McCabe et al., Biotechnology 6:923-926 (1988); Christou et al., Plant Physiol. 87:671-674 (1988)).

There are a variety of methods for the regeneration of plants from plant tissues. The particular method of regeneration will depend on the starting plant tissue and the particular plant species to be regenerated. The regeneration, development and cultivation of plants from single plant protoplast transformants or from various transformed explants is well known in the art (Weissbach and Weissbach, Eds.; In Methods for Plant Molecular Biology; Academic Press, Inc.: San Diego, Calif., 1988). This regeneration and growth process typically includes the steps of selection of transformed cells, culturing those individualized cells through the usual stages of embryonic development or through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present disclosure containing a desired polypeptide is cultivated using methods well known to one skilled in the art.

This disclosure also concerns a method of decreasing the expression of at least one nucleic acid such as a heterologous nucleic acid fragment in a plant cell which comprises:

(a) transforming a plant cell with the recombinant expression construct described herein;

(b) growing fertile mature plants from the transformed plant cell of step (a);

(c) selecting plants containing a transformed plant cell wherein the expression of the nucleic acid such as a heterologous nucleic acid fragment is increased or decreased.

Transformation and selection can be accomplished using methods well-known to those skilled in the art including, but not limited to, the methods described herein.

The soybean seeds can be processed to produce oil and protein. Methods of processing the soybean seeds to produce oil and protein are provided which include one or more steps of dehulling the seeds, crushing the seeds, heating the seeds, such as with steam, extracting the oil, roasting, and extrusion. Processing and oil extraction can be done using solvents or mechanical extraction.

Products formed following processing include, without limitation, soy nuts, soy milk, tofu, texturized soy protein, soybean oil, soy protein flakes, isolated soy protein. Crude or partially degummed oil can be further processed by one or more of degumming, alkali treatment, silica absorption, vacuum bleaching, hydrogenation, interesterification, filtration, deodorization, physical refining, refractionation, and optional blending to produce refined bleached deodorized (RBD) oil.

The oil and protein can be used in animal feed and in food products for human consumption. Provided are food products and animal feed comprising oils, protein and compositions and described herein which contain or are derived from the modified polynucleotides and modified polypeptides. The food products and animal feed may comprise nucleotides comprising one or more of the modified alleles disclosed herein and the modified polynucleotides, polypeptides and plant cell disclosed herein.

Methods of detecting the modified polynucleotides are provided. Methods of extracting modified DNA from a sample or detecting the presence of DNA corresponding to the modified genomic sequences comprising deletions or substitutions disclosed herein in DGAT1 sequences are provided. Such methods comprise contacting a sample comprising soybean genomic DNA with a DNA primer set, that when used in a nucleic acid amplification reaction, such as the polymerase chain reaction (PCR), with genomic DNA extracted from soybeans produces an amplicon that is diagnostic for either the presence or absence of the modified polynucleotide or modified DGAT1 alleles. The methods include the steps of performing a nucleic acid amplification reaction, thereby producing the amplicon and detecting the amplicon. In some embodiments one of the pair of DNA molecules comprises the wild type sequence where the modification such as a deletion occurs with the second of the pair being upstream or downstream as appropriate and suitably in proximity to the wild type sequence where the modification such as deletion occurs, such that an amplicon is produced when the wild type allele is present, but no amplicon is produced when the modified allele is present.

Probes and primers are provided which are of sufficient nucleotide length to bind specifically to the target DNA sequence under the reaction or hybridization conditions. Suitable probes and primers are at least 10, 11, 12, 13, 14, 15, 16, 17, 18, 19, 20, 21, 22, 23, 24, 25, 26, 27, 28, 29 or 30 nucleotides in length, and less than 35, 34, 33, 32, 31, 30, 29, 28, 27, 26, 25, 24, 23, 22, 21, 20, 19, 18, 17, 16, 15, 14, 13, or 12 nucleotides in length. Such probes and primers can hybridize specifically to a target sequence under high stringency hybridization conditions. Preferably, probes and primers have complete or 100% DNA sequence similarity of contiguous nucleotides with the target sequence, although probes which differ from the target DNA sequence but retain the ability to hybridize to target DNA sequence may be also be used. Reverse complements of the primers and probes disclosed herein are also provided and can be used in the methods and compositions described herein.

In some embodiments, one of the pair of DNA molecules comprises the modification or traverses the modification junction, such as, for example, the deletion junctions occurring at position 77 to 78 of SEQ ID NO: 25, or the deletion junctions occurring at position 73 to 74 of SEQ ID NO: 26 with the second DNA molecule of the pair being upstream or downstream of the genomic sequence as appropriate, such that an amplicon is produced when the modified allele is present, but no amplicon is produced when the wild type allele is present. Suitable primers for use in reactions to detect the presence of the modified alleles can be designed based on the junction sequences depicted in FIGS. 1-3 for the modified alleles. The deletion junction sequence can include at least 1, 2, 3, 4, 5, 6, 7, 8, 9, 10, 11, 12, 13, 14, 15, 20, 25 or 30 nucleotides upstream and downstream of the junction, such as provided in SEQ ID NOs: 25 and 26. The modified polynucleotides disclosed herein can include the deletion junction and deletion junction sequences described herein.

Various changes in phenotype are of interest including, but not limited to, one or more of increased stability of the DGAT polypeptide or protein or RNA in the cell, increased expression levels of the DGAT protein or RNA in the cell, increased activity, such as specific activity of the DGAT protein in the cell, increased oil or fatty acid production or oil of fatty acid content of the cell or increased protein content or protein production in the cell.

Methods for extracting and detecting triacylglycerol (TAG), fats or oils from tissues such as leaves, roots and seeds are provided herein. The methods can be used to extract TAG and quantify, measure or detect TAG from the modified leaves or seeds described herein. In some embodiments, the methods include the steps of conducting Solid Phase Extraction (SPE) followed by quantitative gas chromatography. In some embodiments, the methods include the steps of conducting high performance liquid chromatography such as equipped with an evaporative light scattering detector (HPLC-ELSD). TAG is extracted from the tissue, such as leaf or seed tissue, for example using a solvent such as hexane. The methods facilitate an improvement in accuracy of measuring TAG in tissues of at least 1%, 2%, 3%, 4%, 5%, 6%, 7% 8%, 9% or 10% and less than 25%, 20%, 15% or 10%.

For the SPE method, a plate containing a plurality of wells can be used, such as at least 12, 24, 36, 48, 60, 72, 84, or 96 and less than 1026, 512, 256, 128, or 100 wells. Hexane or other solvent can be used to precondition the columns and to load the fractions. Columns can be washed with hexane: dichloromethane:chloroform, such as at an 88:10:4 v/v ratio. Elution of TAG from the columns can be done using a hexane:ethyl acetate blend, at a ratio of at least 95:5, 96:4, and 97:3 hexane:ethyl acetate (v/v) and less than 98:2 and 97:3 hexane:ethyl acetate (v/v). For example, a ratio of 96:4 hexane:ethyl acetate (v/v) can be used. The TAG fraction can be concentrated and resuspended in a solvent such as heptane, derivatization of fatty acids may be carried out for example using trimethylsulfonium hydroxide in methanol, followed by Gas Chromatography—Flame Ionization Detector (GC-FID) for quantification.

For the HPLC-ELSD procedure, the hexane-extracted lipids can be filtered such as through a PTFE filter plate, dried down and resuspended in a solvent such as heptane. A column such as a cyanopropyl column can used to separate lipid species on an HPLC-ELSD. A first phase may include up to 100% hexane (mobile phase A) and a second phase (mobile phase B) may include up to 100% methyl tertiary-butyl ether or a methyl tertiary-butyl ether:isopropanol blend with at least 0%, 0.01%, 0.1%, 0.5%, 1%, 1.5% or 2% and less than 10%, 9%, 8%, 7%, 6%, 5%, 4%, 3%, 2%, 1% or 0.5% isopropanol (v/v) and at least 0%, 0.01% 0.1%, 0.2%, 0.3%, 0.4% or 0.5% and less than 0.6%, 0.5%, 0.4%, 0.3%, 0.2% or 0.1% (v/v) acetic acid. The gradient can be run for example at 0% to 100% of mobile phase B, with re-equilibration of the column to 0% mobile phase B.

The foregoing invention has been described in detail by way of illustration and example for purposes of clarity and understanding. As is readily apparent to one skilled in the art, the foregoing disclosures are only some of the methods and compositions that illustrate the embodiments of the foregoing invention. It will be apparent to those of ordinary skill in the art that variations, changes, modifications, and alterations may be applied to the compositions and/or methods described herein without departing from the true spirit, concept, and scope of the invention.

All publications, patents, and patent applications mentioned in the specification are incorporated by reference herein for the purpose cited to the same extent as if each was specifically and individually indicated to be incorporated by reference herein.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth. Unless expressly stated to the contrary, "or" is used as an inclusive term. For example, a condition A or B is satisfied by any one of the following: A is true (or present) and B is false (or not present), A is false (or not present) and B is true (or present), and both A and B are true (or present).

Example 1: Evaluation of DGAT Variants in Yeast by Measuring Oil Accumulation Yeast (*Saccharomyces cerevisiae*) double mutant (dga1/lro1) was generated for evaluating soybean DGAT variants. The yeast mutant is DGAT/PDAT double null which accumulates a trace amount of oil and can be complemented by soybean DGAT variants. DGAT variants were cloned into a yeast expression vector between PGK1 promoter and PGK1 terminator. The vector was transformed into yeast using a modified version of Clontech Yeastmaker Yeast Transformation Kit. Total 18 independent colonies were picked for each DGAT variant to start liquid culture. Oil content in yeast was determined by staining yeast cell with a fluorescence lipolytic dye, Nile Red. Nile Red staining was performed in 96-well microtiter plates by adding 5 μL of a 0.02 mg per mL stock of Nile Red dissolved in 95% ethanol to 200 mL of a 1:10 dilution of the yeast culture in phosphate-buffered saline (137 mM NaCl, 2.7 mM KCl, 10 mM Na2HPO4, and 1.8 mM KH2PO4, pH 7.4). Staining was done for 5 min, followed by the determination of fluorescence intensity using an excitation wavelength of 489 nm and an emission wavelength of 581 nm. Fluorescence intensity was divided by A600 to correct for differences in cell density, and buffer blanks with no yeast were used to correct for background (Roesler et al 2016 Plant Physiol. 171:878).

Oil content (total fatty acid methyl esters as a percentage of dry weight) and fatty acid composition were determined by quantitative gas chromatography for yeast strains with high Nile Red staining.

Example 2: Evaluation of DGAT Variants in Tobacco Leaf Transient Expression by Measuring Oil Accumulation DGAT variants were evaluated in planta by *Agrobacterium* mediated transient expression in tobacco (*N. benthamiana*) leaves. Gene variants were first cloned into a binary vector between the GM-UBQ promoter and UBQ14 terminator. The constructs also contained DsRed under control of the SCP1 promoter as marker gene. Vectors were transformed into *Agrobacterium* strain AGL1 by electroporation. Liquid cultures were grown at 28 C overnight in a shaking incubator at 250 rpm. Cells were then pelleted and resuspended in infiltration buffer (5 mM MgSO4, 5 mM MES (pH 5.6), and 150 μM acetosyringone). Cultures were then incubated at room temperature for 2-4 hours and diluted to a final OD 600 of 0.2 prior to infiltration. Tobacco plants were grown for approximately 5 weeks before infiltration in a growth chamber under a 16-hour photoperiod, light intensity of 180 $\mu mol \cdot m^{-2} \cdot s^{-1}$, 24 C/20 C light/dark temperature, and 65% relative humidity. The youngest fully expanded leaf was chosen for infiltration (one leaf per plant). *Agrobacterium* suspensions were injected into the underside of leaves using a syringe without a needle while applying counter pressure. The *Agrobacterium* suspension can be seen filling airspaces inside the leaf, which is a visible wetting of the area. Infiltrated leaves were harvested 3 days post-infiltration, frozen on dry ice, and lyophilized. Lipids were extracted from 20 mg dry weight in 2:1 chloroform: methanol after the addition of 0.05 mg tri-C17 TAG as an internal standard. Extracts were loaded on a silica TLC plate and resolved with 70:30:1 hexane:diethylether:acetic acid. The plate was stained with primuline and visualized under UV light. TAG spots were scraped from the plate and derivatized with 5% sulfuric acid in methanol followed by GC-FID. Protein was extracted and analyzed by the Protein Mass Spectrometry.

Example 3: Deletion of Amino Acids in N-Terminal of DGAT Improves DGAT Protein Stability and Produces More Oil in Tobacco Leaf Oil was measured in a tobacco leaf assay according to Example 2. Different DGAT variants were expressed transiently in tobacco leaf under the same soybean UBQ promoter. DGAT protein level was determined by mass spectrometry. The results are presented in FIG. 1. Deletion of AA25-44 at the N-terminus of the DGAT1b WT protein resulted in a 66 percent increase in DGAT protein level, indicating increased DGAT1b stability. The AA25-44 deletion resulted in a similar increase in protein in the GmDGAT1b mod backbone with 14 amino acid substitutions, where a 61 percent increase in protein was observed. The unmodified DGAT1a protein is more stable and expressed at a higher level in tobacco leaf compared to DGAT1b.

Oil content in tobacco leaf expressing different DGAT variants was determined by GC-FID. The results are presented in FIG. 2. Expression of DGAT1b WT increases oil slightly in tobacco leaf. Deletion of AA25-44 in N-terminal of DGAT1b increases oil content in tobacco leaf by 100%. Similarly, Substitution of 14 AA in DGAT1b mod increases oil content by 149%. The stack of AA25-44 deletion with 14 AA substitution provided an increase in oil more than either the AA25-44 deletion or 14 AA substitution. DGAT1b mod and stack of AA25-44 deletion with 14 AA substitution showed a much higher oil content than wild type DGAT1a in tobacco leaves.

Example 4: Substitution of a Single Amino Acid in DGAT Increases Oil Accumulation in Yeast DGAT variants with a single amino acid substitution at various position was expressed under PGK1 promoter in a yeast double mutant as described in Example 1. Oil content in yeast cells were determined by Nile Red staining. Out of 33 variants in DGAT1b backbone tested, 7 DGAT variants show a significant increase in oil content compared to wild type DGAT1b. Similarly, out of 29 variants in DGAT1a backbone tested, 12 DGAT variants showed a significant increase in oil content compared to wild type DGAT1a in yeast (Table 4). The 15 amino acid substitutions showing positive effect on oil accumulation in either DGAT1a or DGAT1b are listed in Table 3.

TABLE 3

List of positive single amino acid substitutions in soybean DGAT1a or DGAT1b

| GmDGAT1B (SEQ ID NO: 2) | GmDGAT1a (SEQ ID NO: 4) |
|---|---|
| BAE93461.1 | AAS78662.1 |
| S58N * | S55N |
| P181A | P175A * |
| A210V * | A204V |
| T216V * | T210V * |
| D258E * | D252E * |
| S264T * | S258T * |
| K328N | K322N * |
| L364V | L358V * |
| D387E | D381E * |
| I440M * | I434M |
| R467Q | R461Q * |
| I479S * | I473S * |
| | T24A * |
| | S31A * |
| | S238A * |

* indicates DGAT with a single amino acid substitution shows a significant increase in oil content compared to wild type DGAT at $P < 0.05$

TABLE 4

Soybean DGAT with a single amino acid substitution increases oil accumulation in yeast

| DGAT Allele | AA Change | % of WT oil content | Significance |
|---|---|---|---|
| DGAT1b | S58N | 123.68 | * |
| DGAT1b | A210V | 119.52 | * |
| DGAT1b | T216V | 136.83 | * |
| DGAT1b | D258E | 134.39 | * |
| DGAT1b | S264T | 121.01 | * |
| DGAT1b | I440M | 114.97 | * |
| DGAT1b | I479S | 146.61 | * |
| DGAT1a | T24A | 107.63 | * |
| DGAT1a | S31A | 114.75 | * |
| DGAT1a | P175A | 107.21 | * |
| DGAT1a | T210V | 107.85 | * |
| DGAT1a | S238A | 105.45 | * |
| DGAT1a | D252E | 115.97 | * |
| DGAT1a | S258T | 112.78 | * |
| DGAT1a | K322N | 113.19 | * |
| DGAT1a | L360V | 106.90 | * |
| DGAT1a | D381E | 105.06 | * |
| DGAT1a | R461Q | 109.47 | * |
| DGAT1a | I473S | 111.07 | * |

* indicates DGAT with a single amino acid substitution shows a significant increase in oil content compared to wild type DGAT at $P < 0.05$ Example 5: Substitution of a Single Amino Acid in DGAT Increases Oil Accumulation in Tobacco Leaf Four positive amino acid substitutions in DGAT1a and 6 positive amino acid substitutions in DGAT1b backbones were further tested in tobacco leaf transient expression as described in Example 2. The results are presented in FIG. 3. Amino acid changes from Threonine to valine at position 210, aspartate to glutamate at position 252, serine to valine at position 258, and isoleucine to serine in DGAT1a protein increases oil accumulation in tobacco leaves compared to DGAT1a wild type (FIG. 3). The corresponding amino acid substitutions in DGAT1b backbone show a similar oil increase compared against wild type DGAT1b in tobacco leaves.

Example 6: Identification of Positive Amino Acid Substitution in Plant DGAT

Plant DGAT amino acid sequences can be identified from public databases, for example using BLAST® (Basic Local Alignment Search Tool) using the soybean DGAT1a and DGTA1b sequences. The DGAT amino acid sequences can be pairwise aligned using alignment software. Corresponding amino acids which can be changed to increase DGAT activity in other plant DGAT proteins are marked with an asterisk in FIG. 4. The modified nucleotides encoding these polypeptides can be expressed in plant cells to produce cells containing modified DGAT polypeptides which show one or more of increased stability, increased specific activity and increased fatty acid content of the cell.

Example 7:Combination of 2-4 amino acid changes in DGAT in yeast

DGAT variants with 2-4 amino acid changes were expressed in yeast as described in Example 1. The different combinations tested and the results are presented in Table 5. Compared to WT DGAT, 8 out of 19 stack variants show an increase in oil accumulation. The stack variants contain at least one amino acid changes from the list in Table 3 of Example 4.

TABLE 5

DGAT variants with 2-4 amino acid changes increase oil content in yeast

| Soybean DGAT Allele | Amino Acid Changes | | | | % of WT oil content | Significance |
|---|---|---|---|---|---|---|
| GmDGAT1b | T216V | I479S | | | 98.75 | |
| GmDGAT1b | C355S | I479S | | | 93.14 | |
| GmDGAT1b | T216V | D258E | | | 98.72 | |
| GmDGAT1b | T216V | S264T | | | 91.90 | |
| GmDGAT1b | D258E | S264T | | | 89.61 | |
| GmDGAT1b | D258E | I479S | | | 128.06 | * |
| GmDGAT1b | K328N | C355S | I479S | | 127.54 | * |
| GmDGAT1b | C355S | N473S | I479S | | 84.80 | |
| GmDGAT1b | T216V | D258E | I479S | | 125.85 | * |
| GmDGAT1b | S58N | I170M | S264T | | 101.39 | |
| GmDGAT1b | R206K | Y231F | S264T | I440M | 70.12 | |
| GmDGAT1b | T216V | K328N | C355S | I479S | 99.37 | |
| GmDGAT1b | V273L | I303V | L364V | R467K | 111.96 | * |
| GmDGAT1b | T216V | D258E | S264T | I479S | 90.85 | |
| GmDGAT1a | T210V | I473S | | | 119.31 | * |
| GmDGAT1a | C349S | I473S | | | 104.03 | * |
| GmDGAT1a | T210V | D252E | | | 107.33 | * |
| GmDGAT1a | V267L | I297V | L358V | R461K | 100.41 | |
| GmDGAT1a | T210V | D252E | S258T | I473S | 125.59 | * |

* indicates DGAT with 2-4 amino acid substitutions show a significant increase in oil content compared to wild type DGAT at $P < 0.05$ Example 8: Combination of 2-4 Amino Acid Changes in DGAT in Tobacco Leaf Assay The DGAT1b variants with 2-4 amino acid changes used in Example 7 were also tested in tobacco leaf transient expression. The results are presented in FIG. 5. Seven out of eleven DGAT1b variants with 2-4 amino acid substitutions show more oil accumulation than wild type DGAT1b. One DGAT1b variant with 3 amino acid substitutions, C355S, N473S, and I479S-increased oil more than the GmDGAT1b mod with 14 amino acid changes.

Example 9: Combination of N-Terminal Deletion with Amino Acid Substitution

The DGAT variant with N-terminal deletion at AA25-44 improves DGAT stability and increase oil accumulation in tobacco transient expression. DGAT variants which combined an N-terminal deletion with amino acid substitutions were tested to determine whether further increases DGAT activity and oil accumulation would occur. As shown in FIG. 6, GmDGAT1b mod with AA25-44 deletion accumulates more oil than either GmDGAT1b mod or GMDGAT1b with AA25-44 deletion. Similarly, GmDGAT1b with stack of C355S, N473S and I479S substitutions and the AA25-44 deletion increases oil more than either GmDGAT1b with AA25-44 deletion or GmDGAT1b with C355S, N473S and I479S substitutions. The combination of N-terminal deletion with C-terminal amino acid substitutions can further improve DGAT for higher oil accumulation.

Example 10: Soybean Optimized Expression Cassettes for Guide RNA/Cas Endonuclease Based Genome Modification in Soybean Plants For genome engineering applications, the type CRISPR/Cas system minimally requires the Cas9 protein and a duplexed crRNA/tracrRNA molecule or a synthetically fused crRNA and tracrRNA (guide RNA) molecule for DNA target site recognition and cleavage (Gasiunas et al. (2012) *Proc. Nat. Acad. Sci. USA* 109: E2579-86, Jinek et al. (2012) *Science* 337:816-21, Mali et al. (2013) Science 339:823-26, and Cong et al. (2013) Science 339:819-23). Described herein is a guideRNA/Cas endonuclease system that is based on the type II CRISPR/Cas system and consists of a Cas endonuclease and a guide RNA (or duplexed crRNA and tracrRNA) that together can form a complex that recognizes a genomic target site in a plant and introduces a double-strand-break into the target site.

To use the guide RNA/Cas endonuclease system in soybean, the Cas9 gene from *Streptococcus pyogenes* M1 GAS (SF370) was soybean codon optimized per standard techniques known in the art. To facilitate nuclear localization of the Cas9 protein in soybean cells, a simian virus 40 (SV40) large T-antigen nuclear localization signal, representing the amino acid molecules of PKKKRKV (with a linker SRAD (SRADPKKKRKV), was added to the carboxyl terminus of the codon optimized Cas9 to facilitate transporting the codon optimized Cas9 protein to the nucleus. The soybean optimized Cas9 gene was operably linked to a soybean constitutive promoter such as the strong soybean constitutive promoter GM-EF1A2 (US patent application 20090133159). or regulated promoter by standard molecular biological techniques.

The second component necessary to form a functional guide RNA/Cas endonuclease system for genome engineering applications is a duplex of the crRNA and tracrRNA molecules or a synthetic fusing of the crRNA and tracrRNA molecules, a guide RNA. To confer efficient guide RNA expression (or expression of the duplexed crRNA and tracrRNA) in soybean, the soybean U6 polymerase III promoter and U6 polymerase III terminator were used.

Plant U6 RNA polymerase III promoters have been cloned and characterized from such as *Arabidopsis* and *Medicago truncatula* (Waibel and Filipowicz, NAR 18:3451-3458 (1990); Li et al., J. Integrat. Plant Biol. 49:222-229 (2007); Kim and Nam, Plant Mol. Biol. Rep. 31:581-593 (2013); Wang et al., RNA 14:903-913 (2008)). Soybean U6 small nuclear RNA (snRNA) genes were identified herein by searching public soybean variety Williams82 genomic sequence using *Arabidopsis* U6 gene coding sequence. Approximately 0.5 kb genomic DNA sequence upstream of the first G nucleotide of a U6 gene was selected to be used as a RNA polymerase III promoter for example, GM-U6-13.1 promoter, to express guide RNA to direct Cas9 nuclease to designated genomic site. The guide RNA coding sequence was 76 bp long and comprised a 20 bp variable targeting domain from a chosen soybean genomic target site on the 5' end and a tract of 4 or more T residues as a transcription terminator on the 3' end. The first nucleotide of the 20 bp variable targeting domain was a G residue to be used by RNA polymerase III for transcription. Other soybean U6 homologous genes promoters were similarly cloned and used for small RNA expression.

Since the Cas9 endonuclease and the guide RNA need to form a protein/RNA complex to mediate site-specific DNA double strand cleavage, the Cas9 endonuclease and guide RNA must be expressed in same cells. To improve their co-expression and presence, the Cas9 endonuclease and guide RNA expression cassettes were linked into a single DNA construct.

Example 11: Selection of Soybean DGAT1a and DGAT1b Target Sites to be Cleaved by the Guide RNA/Cas Endonuclease System Specific gRNAs are designed to target the two soybean DGAT genes (Glyma.13g106100 for DGAT1a and Glyma.17g053300 for DGAT1b). The GM-DGAT-CR1 is targeting the N-terminal region of DGAT1a gene. The GM-DGAT-CR3 is targeting the N-terminal region of the DGAT1b gene. The GM-DGAT-CR4 is targeting downstream of the N-terminal region of both DGAT1a and DGAT1b gene (Table 6).

TABLE 6

Guide RNA/Cas9 endonuclease target sites on soybean DGAT1a and DGAT1b genes a

| Name of gRNA-Cas9 endonuclease target site | Sequences (without PAM) |
|---|---|
| GM-DGAT-CR1 | GGAATTGAAGAGGCCAGCGG (SEQ ID NO: 31) |
| GM-DGAT-CR3 | GCGGCGGTGGAGGTGGCGGA (SEQ ID NO: 32) |
| GM-DGAT-CR4 | GGACAGTTCCGGTGATGACT (SEQ ID NO: 33) |

The soybean U6 small nuclear RNA promoter, GM-U6-13.1, was used to express the guide RNAs to direct Cas9 nuclease to designated genomic target sites. A soybean codon optimized Cas9 endonuclease expression cassette and a guide RNA expression cassette were linked in the plasmid (RTW1630, RTW1632 or RTW1633).

Example 12: Delivery of the Guide RNA/Cas9 Endonuclease System DNA to Soybean by Stable Transformation Soybean somatic embryogenic suspension cultures were induced from a DuPont Pioneer proprietary elite cultivar 93Y21 as follows. Cotyledons (~3 mm in length) were dissected from surface sterilized, immature seeds and were cultured for 6-10 weeks in the light at 26° C. on a Murashige and Skoog (MS) media containing 0.7% agar and supplemented with 10 mg/ml 2,4-D (2,4-Dichlorophenoxyacetic acid). Globular stage somatic embryos, which produced secondary embryos, were then excised and placed into flasks containing liquid MS medium supplemented with 2,4-D (10 mg/ml) and cultured in light on a rotary shaker. After repeated selection for clusters of somatic embryos that multiplied as early, globular staged embryos, the soybean embryogenic suspension cultures were maintained in 35 ml liquid media on a rotary shaker, 150 rpm, at 26° C. with fluorescent lights on a 16:8-hour day/night schedule. Cultures were subcultured every two weeks by inoculating approximately 35 mg of tissue into 35 ml of the same fresh liquid MS medium.

Soybean embryogenic suspension cultures were then transformed by the method of particle gun bombardment using a DuPont Biolistic™ PDS1000/HE instrument (Bio-Rad Laboratories, Hercules, Calif.). To 50 μl of a 60 mg/ml 1.0 mm gold particle suspension were added in order: 30 μl of equal amount (30 ng/μl) plasmid DNA, 20 μl of 0.1 M spermidine, and 25 μl of 5 M $CaCl_2$. The particle preparation was then agitated for 3 minutes, spun in a centrifuge for 10 seconds and the supernatant removed. The DNA-coated particles were then washed once in 400 μl 100% ethanol and resuspended in 45 μl of 100% ethanol. The DNA/particle suspension was sonicated three times for one second each. Then 5 μl of the DNA-coated gold particles was loaded on each macro carrier disk.

Approximately 300-400 mg of a two-week-old suspension culture was placed in an empty 60×15 mm Petri dish and the residual liquid removed from the tissue with a pipette. For each transformation experiment, approximately 5 to 10 plates of tissue were bombarded. Membrane rupture pressure was set at 1100 psi and the chamber was evacuated to a vacuum of 28 inches mercury. The tissue was placed approximately 3.5 inches away from the retaining screen and bombarded once. Following bombardment, the tissue was divided in half and placed back into liquid media and cultured as described above.

Five to seven days post bombardment, the liquid media was exchanged with fresh media containing 30 mg/ml hygromycin as selection agent. This selective media was refreshed weekly. Seven to eight weeks post bombardment, green, transformed tissue was observed growing from untransformed, necrotic embryogenic clusters. Isolated green tissue was removed and inoculated into individual flasks to generate new, clonally propagated, transformed embryogenic suspension cultures. Each clonally propagated culture was treated as an independent transformation event and subcultured in the same liquid MS media supplemented with 2,4-D (10 mg/ml) and 30 ng/ml hygromycin selection agent to increase mass. The embryogenic suspension cultures were then transferred to agar solid MS media plates without 2,4-D supplement to allow somatic embryos to develop. A sample of each event was collected at this stage for quantitative PCR analysis.

Cotyledon stage somatic embryos were dried-down (by transferring them into an empty small Petri dish that was seated on top of a 10 cm Petri dish containing some agar gel to allow slow dry down) to mimic the last stages of soybean seed development. Dried-down embryos were placed on germination solid media and transgenic soybean plantlets were regenerated. The transgenic plants were then transferred to soil and maintained in growth chambers for seed production. Transgenic events were sampled at somatic embryo stage or TO leaf stage for molecular analysis.

Example 13: Detection of Site-Specific Dropout Mutations Mediated by the Guide RNA/Cas9 System in Stably Transformed Soybean Genomic DNA was extracted from somatic embryo samples and leaf samples and analyzed by PCR analyses using primers specific respectively to DGAT1a and DGAT1b genes (Tables 7 and 8).

TABLE 7

PCR primers for the deletion in the N-terminal region of the DGAT1a and DGAT1b genes

| Target Gene | Primer1 | SEQ ID NO: | Primer2 | SEQ ID NO: |
|---|---|---|---|---|
| DGAT1a | WOL1469 | 34 | WOL1470 | 35 |
| DGAT1b | WOL1471 | 36 | WOL1009 | 37 |

TABLE 8

Detection of the deletion in the N-terminal region of the DGAT1a and DGAT1b genes

| Target Site | Primer set | PCR band size of WT | PCR band size of band containing N-terminal deletion |
|---|---|---|---|
| DGAT1a | WOL1469/ WOL1470 | 485 bp (position 34-518 of SEQ ID NO: 30) | 437 bp (position 34-518 SEQ ID NO: 30) |
| DGAT1b | WOL1471/ WOL1472 | 557 bp (position 11-567 SEQ ID: 29) | 497 bp (position 11-567 SEQ ID: 29) |

The PCR bands were cloned into pCR2.1 vector using a TOPO-TA cloning kit (Invitrogen) and multiple clones were sequenced to check for target site sequence changes. The 48 bp dropout of the DGAT1a N-terminal region (corresponding to positions 77 to 124 of SEQ ID NO: 3) and 60 bp deletion of the DGAT1b (corresponding to positions 74 to 133 of SEQ ID NO: 1) N-terminal region were detected in the 2.1 variant, in which the DGAT1b N-terminal region deletion were presented as bi-allelic and the DGAT1a N-terminal region deletion was shown as mono-allelic, with the second DGAT1a allelic as a 1 bp deletion knockout (Table 9). For the 2.2 variant, mono-allelic dropout of the DGAT1a gene was detected, with the second DGAT1a allele as a WT. All other variants were detected either as frameshift knockouts or as WT alleles.

TABLE 9

N-terminal deletion or knockout variants of the DGAT1a and DGAT1b genes

| Variant | DGAT1a | DGAT1b |
|---|---|---|
| 2.1 | 48 bp dropout/1 bp del | 60 bp dropout/ 60 bp dropout |
| 2.2 | 48 bp dropout/WT | 2 bp del |
| 4.2 | WT | 1 bp del |
| 4.3 | WT | WT |

Example 14: Expression of Novel DGAT Genes in Soybean Seed

The expression of DGAT variants in soybean was described in detail previously (Roesler et al Plant Physiol. 2016 878-893). Briefly, DGAT variants were cloned into an expression vector flanked by seed specific soybean Ole 2b promoter and soybean MYB2 terminator. The expression vectors containing constructs as listed in Table 10 were introduced into soybean by Ochrobacteria transformation. Transgenic T1 seed oil content was determined by SS-NIR as described previously (Roesler et al Plant Physiol. 2016 878-893). While 75% of T1 seeds are transgenic, 25% of T1 seeds are wild type segregates. The average of all T1 seeds oil content is thus an underestimate of DGAT efficacy. Compared to untransformed 93Y21 wild type, overexpression of Gm-DGAT1b WT under the oleosin promoter does not increase seed oil content significantly. Gm-DGAT1b Mod with 14 amino acid substitutions shows a significant improvement in increasing oil compared to wild type DGAT1b (Table 10). To reduce number of amino acid substitutions to facilitate efficient gene editing, a few DGAT variants with 1-4 amino acid substitutions were tested in transgenic plants for increasing seed oil content. Gm-DGAT1b-I479S, Gm-DGAT1b-C355S-I479S, Gm-DGAT1b-C355S-N473S-I479S, and Gm-DGAT1b-T216V-D258E-S264T-479S show a significant increase in seed oil content compared to wild type DGAT1b. Overexpression of Gm-DGAT1b-S264T and Gm-DGAT1b-D258E-479S, however, does not increase seed oil content. In addition, substitution of 14 amino acids or a single amino acid substitution 1473S in DGAT1a backbone increases seed oil content significantly compared to wild type DGAT1b and untransformed 93Y21 (Table 10)

TABLE 10

DGAT variants increases seed oil content in stable transgenic events

| Constructs | | | Average T1 seed oil % | Significance |
|---|---|---|---|---|
| Wild type 93Y21 | | | 19.75 ± 1.03 | |
| Gm-Ole2b promoter | Gm-DGAT1b-WT | Gm-MYB2 Term | 19.72 ± 0.97 | |
| Gm-Ole2b promoter | Gm-DGAT1b Mod | Gm-MYB2 Term | 21.52 ± 0.96 | ** |
| Gm-Ole2b promoter | Gm-DGAT1b-S264T | Gm-MYB2 Term | 19.88 ± 1.05 | |
| Gm-Ole2b promoter | Gm-DGAT1b-I479S | Gm-MYB2 Term | 21.01 ± 1.61 | ** |
| Gm-Ole2b promoter | Gm-DGAT1b-D258E-I479S | Gm-MYB2 Term | 20.06 ± 0.88 | |
| Gm-Ole2b promoter | Gm-DGAT1b-C355S-I479S | Gm-MYB2 Term | 20.86 ± 1.27 | ** |
| Gm-Ole2b promoter | Gm-DGAT1b-C355S-N473S-I479S | Gm-MYB2 Term | 21.02 ± 0.97 | ** |
| Gm-Ole2b promoter | Gm-DGAT1b-T216V-D258E-S264T-I479S | Gm-MYB2 Term | 21.20 ± 1.24 | ** |
| Gm-Ole2b promoter | Gm-DGAT1a Mod | Gm-MYB2 Term | 20.92 ± 1.37 | ** |
| Gm-Ole2b promoter | Gm-DGAT1a-I473S | Gm-MYB2 Term | 20.48 ± 1.13 | ** |

Example 15: Deletion Studies of N-Terminal Region of DGAT for Increasing DGAT Protein Stability The N-terminal region of DGAT before the first conserved membrane domain (e.g. from positions 1-108 of SEQ ID NO: 2) is variable and impacts DGAT protein stability. Different size deletions from one amino acid to 107 amino acids are made in this region. The efficacy of DGAT deletion variants are tested in tobacco leaf transient expression or in stable transgenic expression as described in Example 2 or in Roesler et al Plant Physiol. 2016 878-893. The deletion variants with improved stability are identified based on oil accumulation in tobacco leaf assay or transgenic plants. DGAT polypeptides with deletions ranging from 1 amino acid to 107 amino acids will show improved stability evidenced by increased protein levels or oil content in transformed cells compared with a comparable DGAT not comprising an N-terminal deletion. When expressed in a seed, DGAT polypeptides with deletions ranging from 1 amino acid to 107 amino acids will result in increased oil content in the seed compared with a comparable seed expressing the wild-type or native DGAT sequences.

Example 16: Methods for Separating and Quantifying TAG from Leaf Lipids

In addition to TLC according to Example 2 followed by GC-FID other methods were used to separate lipid classes and quantify TAG. These methods include use of Solid Phase Extraction (SPE) followed by quantitative gas chromatography and high performance liquid chromatography equipped with an evaporative light scattering detector (HPLC-ELSD). Sample collection and lipid extraction methods were modified to enable sample collection and analysis in a 96-well plate format. Approximately 10 mg leaf tissue was sampled into pre-weighed 1.2 ml polypropylene tubes. The tissue was lyophilized and the exact dry weight was obtained. Four monophasic extractions of 100% hexane were used to extract the neutral lipids from lyophilized leaf discs, and were pooled in a clean 96-well plate. For the SPE method, an internal standard, 0.02 mg tri-C17 TAG, was added prior to extraction of neutral lipids. TAG was isolated by SPE using 96-well aminopropyl SPE plates (Thermo). Columns were preconditioned with 1 mL of hexane prior to loading samples as a 0.5 mL hexane fraction. Columns were washed with 1 mL of hexane:dichloromethane:chloroform (88:10:4 v/v), then TAG was eluted with 1 mL of Hexane: ethyl acetate (96:4 v/v). The TAG fraction was concentrated and resuspended in 180 μl heptane. Fatty acids were derivatized by the addition of 20 μl of approximately 0.25 M trimethylsulfonium hydroxide in methanol (Sigma-Aldrich) was added, followed by GC-FID for quantification. For the HPLC-ELSD procedure, the hexane-extracted lipids were filtered through a PTFE 0.2 μm filter plate. Samples were then dried down and resuspended in 80 μL of heptane. A cyanopropyl column (Luna 5 μM CN 100A 250×4.6 mm; Phenomenx) was used to separate lipid species on an HPLC-ELSD with hexane as mobile phase A and methyl tertiary-butyl ether (MTBE):isopropanol (95:5 v/v) plus 0.2% acetic acid as mobile phase B, with a gradient of 0% to 100% B, with re-equilibration of the column to 0% B. A standard curve of tri-C17 TAG was run with each sample set to quantify TAG as Oil Content (% of DW).

TAG quantification procedures including TLC/GC-FID procedure of Example 2 were compared by transiently expressing empty vector (EV), GmDGAT1b WT (SEQ ID NO:2), and GmDGAT1b mod (SEQ ID NO:27) in tobacco leaf. The oil content values are shown in (FIG. 7). The SPE and HPLC procedures were found to effectively quantify TAG in the leaves and modified leaves disclosed herein and enabled high-throughput analysis of TAG accumulation.

Example 17. Additional Single to Quadruple Amino Acid Changes in DGAT Increase Oil Content in Tobacco Leaf Assay Additional GmDGAT1b variants were tested in the tobacco leaf assay and directly compared using the SPE/GC-FID and HPLC-ELSD procedures. Similar trends were observed between the two procedures for any of the samples tested (FIG. 8). Single amino acid substitution variants GmDGAT1b S264T and GmDGAT1b N473S significantly increased oil content in tobacco leaves compared to GmDGAT1b WT (FIG. 8). Using the SPE/GC-FID procedure, single amino acid substitution GmDGAT1b variant S264T, double variants C355S I479S and D258E I479S, triple variant C355S N473S I479S, and quadruple variant T216V D258E S264T I479S all had significant increases in oil content compared to the WT (FIG. 9). The triple GmDGAT1b variant C355S N473S I479S had comparable oil content as GmDGAT1b mod, with 14 amino acid substitutions, and N473S almost reached GmDGAT1b mod oil content levels (FIG. 9). This triple amino acid substitution DmDGAT1b variant C355S N473S I479S also had a significantly increased oil/protein ratio (FIG. 10), suggesting that this variant may have improved DGAT activity. These results show that 1-4 amino acid substitutions are sufficient to improve GmDGAT1b WT in planta

What is claimed is:

1. A modified polynucleotide encoding a diacylglycerol acyltransferase-1 (DGAT1) polypeptide having at least 95% identity to SEQ ID NO:2, the polynucleotide encoding a modification comprising a non-asparagine at the position corresponding to position 473 of SEQ ID NO:2, a non-cysteine at the position corresponding to position 355 of SEQ ID NO:2, and a non-isoleucine at the position corresponding to position 479 of SEQ ID NO: 2, wherein when expressed in a plant cell, the polynucleotide increases the fatty acid content of the plant cell compared to a plant cell comprising a comparable polynucleotide without the modification.

2. The modified polynucleotide of claim 1, wherein the polypeptide encoded by the modified polynucleotide has at least 98% identity to SEQ ID NO:2.

3. The modified polynucleotide of claim 1, wherein the polynucleotide encodes a serine at the position corresponding to position 473 of SEQ ID NO: 2.

4. The modified polynucleotide of claim 1, wherein the polynucleotide encodes a serine at the position corresponding to position 355 of SEQ ID NO:2.

5. The modified polynucleotide of claim 1, wherein the polynucleotide encodes a serine at the position corresponding to position 479 of SEQ ID NO: 2.

6. The modified polynucleotide of claim 3, wherein the polynucleotide encodes a serine at the position corresponding to position 479 of SEQ ID NO:2.

7. The modified polynucleotide of claim 1, wherein the polynucleotide encodes a serine at the position corresponding to position 473 of SEQ ID NO: 2, a serine at the position corresponding to position 355 of SEQ ID NO: 2 and a serine at the position corresponding to position 479 of SEQ ID NO: 2.

8. The modified polynucleotide of claim 1, wherein the polypeptide further comprises a deletion of at least 1 and less than 107 amino acids corresponding to the region at positions 1 to 107 of SEQ ID NO: 2, wherein the DGAT1 polypeptide has increased stability when expressed in a plant cell.

9. The modified polynucleotide of claim 1, wherein the DGAT1 further comprises (i) at least one amino acid motif selected from the group consisting of APTLCYQ (SEQ ID NO: 38), FGDREFYXDWWNA (SEQ ID NO: 39) and LLYYHD (SEQ ID NO: 40), where X is any amino acid; (ii) at least one amino acid motif selected from the group consisting of APTLCYQ (SEQ ID NO: 38), FGDREFYXDWWNA (SEQ ID NO: 39) and LLYYHD (SEQ ID NO: 40), where X is K or Q; or (iii) at least one amino acid motif selected from the group consisting of ESPLSSDX'IFX'QSHAGLX'NLCX'VVLX'AVNX'R-LIIENLMKYGX'LI (SEQ ID NO 41) and GFIIEQYINPIV-X'NSX'HPL (SEQ ID NO:42), wherein X' is any amino acid.

10. A plant cell comprising the modified polynucleotide of claim 1, wherein the plant cell has an increased fatty acid content compared to a plant cell comprising a comparable DGAT1 polynucleotide without the modification.

11. A soybean seed comprising the cell of claim 10, wherein the soybean seed has an increased oil content compared to a seed comprising the comparable polynucleotide without the modification.

12. The soybean seed of claim 11, wherein the oil content is increased by at least 5%, 10%, 15% or 20%.

13. A method for increasing the oil content of a soybean cell comprising a polynucleotide encoding a DGAT1 polypeptide, the method comprising a. inducing a break in the genome of the soybean cell and repairing the break, wherein the repair of the break results in at least three nucleotide substitutions in the polynucleotide, the substitutions encoding a non-asparagine at the position corresponding to position 473 of SEQ ID NO:2, a non-cysteine at the position corresponding to position 355 of SEQ ID NO:2, and a non-isoleucine at the position corresponding to position 479 of SEQ ID NO: 2 to produce a modified polynucleotide encoding a modified polypeptide;

b. expressing the modified polypeptide in the soybean cell using an endogenous promoter of the polynucleotide, wherein the fatty acid content of the soybean cell is increased compared to a soybean cell expressing a comparable polypeptide without the substitutions.

14. A plant cell comprising the modified polynucleotide of claim 2.

15. A soybean seed comprising the cell of claim 14, wherein the soybean seed has an increased oil content compared to a seed comprising the comparable polynucleotide without the modification.

16. The soybean seed of claim 15, wherein the oil content is increased by at least 5%.

17. A plant cell comprising the modified polynucleotide of claim 7.

18. A soybean seed comprising the cell of claim 17, wherein the soybean seed has an increased oil content compared to a seed comprising the comparable polynucleotide without the modification.

19. The soybean seed of claim 18, wherein the oil content is increased by at least 5%.

20. A polypeptide encoded by the polynucleotide of claim 1.

* * * * *

SEQUENCE LISTING

```
<160> NUMBER OF SEQ ID NOS: 42

<210> SEQ ID NO 1
<211> LENGTH: 1515
<212> TYPE: DNA
<213> ORGANISM: Glycine max

<400> SEQUENCE: 1

atggcgattt ccgatgagcc tgaaagtgta gccactgctc tcaaccactc ttccctgcgc     60

cgccgtccct ccgccacctc caccgccggc ctcttcaatt cgcctgagac aaccaccgac    120

agttccggtg atgacttggc caaggattct ggttccgacg actccatcaa cagcgacgac    180

gccgccgtca attcccaaca gcaaaacgaa aaacaagaca ctgatttctc cgtcctcaaa    240

ttcgcctacc gtccttccgt ccccgctcac cgcaaagtga aggaaagtcc gctcagctcc    300

gacactattt tccgtcagag tcacgcgggc ctcttcaacc tttgtatagt agtccttgtt    360

gctgtgaata gccgactcat cattgagaat ttaatgaagt atggttggtt gatcaaatct    420

ggcttttggt ttagttcaaa gtcattgaga gactggcccc ttttcatgtg ttgtctttct    480

cttgtggtat ttcctttcgc tgcctttata gtggagaagt tggcacaacg gaagtgtata    540

cccgaaccag ttgttgttgt acttcatata atcattacct caacttcgct tttctatcca    600
```

```
gttttagtta ttctcaggtg tgattctgct tttgtatcag gtgtcacgtt aatgctgttt    660

tcttgtgttg tatggttaaa attggtgtct tatgcacata caaactatga tatgagagca    720

cttaccaaat tagttgaaaa gggagaagca ctgctcgata ctctgaacat ggactatcct    780

tacaacgtaa gcttcaagag cttggcatat ttcctggttg cccctacatt atgttaccag    840

ccaagctatc ctcgcacacc ttatattcga aagggttggt tgtttcgcca acttgtcaag    900

ctgataatat ttacaggagt tatgggattt ataatagaac aatatattaa tcccatagta    960

caaaattcac agcatcctct caagggaaac cttctttacg ccaccgagag agttctgaag   1020

ctttctgttc caaatttata tgtgtggctc tgcatgttct attgcttttt ccacctttgg   1080

ttaaatatcc tggcagagct tcttcgattt ggtgatcgtg aattctacaa ggattggtgg   1140

aatgccaaaa ctgtcgaaga ttattggagg atgtggaata tgcctgttca caaatggatg   1200

atccgccacc tatattttcc atgtttaagg cacggtctac caaaggctgc tgctctttta   1260

attgccttcc tggtttctgc tttattccat gagctgtgca ttgctgttcc ttgccacata   1320

ttcaagttgt gggctttcgg tggaattatg tttcaggttc ctttggtctt gatcactaat   1380

tatctgcaaa ataaattcag aaactcaatg gttggaaata tgatttttttg gttcatattc   1440

agtatccttg gtcaacctat gtgtgtactg ctatactacc atgacttgat gaataggaaa   1500

ggcaaacttg actga                                                    1515
```

<210> SEQ ID NO 2
<211> LENGTH: 504
<212> TYPE: PRT
<213> ORGANISM: Glycine max

<400> SEQUENCE: 2

```
Met Ala Ile Ser Asp Glu Pro Glu Ser Val Ala Thr Ala Leu Asn His
1               5                   10                  15

Ser Ser Leu Arg Arg Arg Pro Ser Ala Thr Ser Thr Ala Gly Leu Phe
            20                  25                  30

Asn Ser Pro Glu Thr Thr Thr Asp Ser Ser Gly Asp Asp Leu Ala Lys
        35                  40                  45

Asp Ser Gly Ser Asp Asp Ser Ile Asn Ser Asp Asp Ala Ala Val Asn
    50                  55                  60

Ser Gln Gln Gln Asn Glu Lys Gln Asp Thr Asp Phe Ser Val Leu Lys
65                  70                  75                  80

Phe Ala Tyr Arg Pro Ser Val Pro Ala His Arg Lys Val Lys Glu Ser
                85                  90                  95

Pro Leu Ser Ser Asp Thr Ile Phe Arg Gln Ser His Ala Gly Leu Phe
            100                 105                 110

Asn Leu Cys Ile Val Val Leu Val Ala Val Asn Ser Arg Leu Ile Ile
        115                 120                 125

Glu Asn Leu Met Lys Tyr Gly Trp Leu Ile Lys Ser Gly Phe Trp Phe
    130                 135                 140

Ser Ser Lys Ser Leu Arg Asp Trp Pro Leu Phe Met Cys Cys Leu Ser
145                 150                 155                 160

Leu Val Val Phe Pro Phe Ala Ala Phe Ile Val Glu Lys Leu Ala Gln
                165                 170                 175

Arg Lys Cys Ile Pro Glu Pro Val Val Val Val Leu His Ile Ile Ile
            180                 185                 190

Thr Ser Thr Ser Leu Phe Tyr Pro Val Leu Val Ile Leu Arg Cys Asp
        195                 200                 205
```

```
Ser Ala Phe Val Ser Gly Val Thr Leu Met Leu Phe Ser Cys Val Val
    210                 215                 220

Trp Leu Lys Leu Val Ser Tyr Ala His Thr Asn Tyr Asp Met Arg Ala
225                 230                 235                 240

Leu Thr Lys Leu Val Glu Lys Gly Glu Ala Leu Leu Asp Thr Leu Asn
                245                 250                 255

Met Asp Tyr Pro Tyr Asn Val Ser Phe Lys Ser Leu Ala Tyr Phe Leu
            260                 265                 270

Val Ala Pro Thr Leu Cys Tyr Gln Pro Ser Tyr Pro Arg Thr Pro Tyr
        275                 280                 285

Ile Arg Lys Gly Trp Leu Phe Arg Gln Leu Val Lys Leu Ile Ile Phe
    290                 295                 300

Thr Gly Val Met Gly Phe Ile Ile Glu Gln Tyr Ile Asn Pro Ile Val
305                 310                 315                 320

Gln Asn Ser Gln His Pro Leu Lys Gly Asn Leu Leu Tyr Ala Thr Glu
                325                 330                 335

Arg Val Leu Lys Leu Ser Val Pro Asn Leu Tyr Val Trp Leu Cys Met
            340                 345                 350

Phe Tyr Cys Phe Phe His Leu Trp Leu Asn Ile Leu Ala Glu Leu Leu
        355                 360                 365

Arg Phe Gly Asp Arg Glu Phe Tyr Lys Asp Trp Trp Asn Ala Lys Thr
    370                 375                 380

Val Glu Asp Tyr Trp Arg Met Trp Asn Met Pro Val His Lys Trp Met
385                 390                 395                 400

Ile Arg His Leu Tyr Phe Pro Cys Leu Arg His Gly Leu Pro Lys Ala
                405                 410                 415

Ala Ala Leu Leu Ile Ala Phe Leu Val Ser Ala Leu Phe His Glu Leu
            420                 425                 430

Cys Ile Ala Val Pro Cys His Ile Phe Lys Leu Trp Ala Phe Gly Gly
        435                 440                 445

Ile Met Phe Gln Val Pro Leu Val Leu Ile Thr Asn Tyr Leu Gln Asn
    450                 455                 460

Lys Phe Arg Asn Ser Met Val Gly Asn Met Ile Phe Trp Phe Ile Phe
465                 470                 475                 480

Ser Ile Leu Gly Gln Pro Met Cys Val Leu Leu Tyr Tyr His Asp Leu
                485                 490                 495

Met Asn Arg Lys Gly Lys Leu Asp
            500
```

<210> SEQ ID NO 3
<211> LENGTH: 1497
<212> TYPE: DNA
<213> ORGANISM: Glycine max

<400> SEQUENCE: 3

```
atggcgattt ccgatgagcc tgaaactgta gccactgctc tcaaccactc ttccctgcgc     60

cgccgtccca ccgccgctgg cctcttcaat tcgcccgaga cgaccaccga cagttccggt    120

gatgacttgg ccaaggattc cggttccgac gactccatca gcagcgacgc cgccaattcg    180

caaccgcaac aaaaacaaga cactgatttc tccgtcctca aattcgccta ccgtccttcc    240

gtccccgctc atcgcaaagt gaaggaaagt ccgctcagct ccgacaccat tttccgtcag    300

agtcacgcgg gcctcttcaa cctctgtata gtagtccttg ttgctgtgaa tagccgactc    360

atcattgaga atttaatgaa gtatggttgg ttgatcaaat ctggcttttg gtttagctca    420
```

```
aagtcattga gagactggcc cctcttcatg tgttgtcttt ctcttgtggt atttcctttt    480

gctgcattta tagtggagaa gttggcacag cagaagtgta tacccgaacc agttgttgtt    540

gtacttcata taatcattac ctcagcttca cttttctatc cagttttagt aattctcagg    600

tgtgattctg cttttctatc aggtgttacg ttaatgctat ttgcttgtgt tgtatggtta    660

aaattggtgt cttatgcaca tacaaactat gatatgagag cacttaccaa atcagttgaa    720

aagggagaag ctctgcccga tactctgaac atggactatc cttacaatgt aagcttcaag    780

agcttagcat atttcctggt tgcccctaca ttatgttacc agccaagcta tcctcgcaca    840

ccttatattc gaaagggttg gctgtttcgc caacttgtca agctgataat atttacagga    900

gttatgggat ttataataga acaatacatt aatcccattg tacaaaattc acagcatcct    960

ctcaagggaa accttcttta cgccatcgag agagttctga agctttctgt tccaaattta   1020

tatgtgtggc tctgcatgtt ctattgcttt ttccaccttt ggttaaatat attggcagag   1080

cttcttcgat ttggtgatcg tgaattctac caggattggt ggaatgccaa aactgttgaa   1140

gattattgga ggatgtggaa tatgcctgtt cacaaatgga tgatccgcca cctatatttt   1200

ccatgtttaa ggcacggtat accaaaggcc gttgctcttt taattgcctt cctggtttct   1260

gctttattcc atgagctgtg catcgctgtt ccttgccaca tattcaagtt gtgggctttc   1320

ggtggaatta tgtttcaggt tcctttggtc ttcatcacta attatctgca aaataaattc   1380

agaaactcga tggttggaaa tatgattttt tggttcatat tcagtattct tggtcaacct   1440

atgtgcgtac tgctatatta ccatgactta atgaatagga aaggcaaact tgactga      1497
```

<210> SEQ ID NO 4
<211> LENGTH: 498
<212> TYPE: PRT
<213> ORGANISM: Glycine max

<400> SEQUENCE: 4

```
Met Ala Ile Ser Asp Glu Pro Glu Thr Val Ala Thr Ala Leu Asn His
1               5                   10                  15

Ser Ser Leu Arg Arg Arg Pro Thr Ala Ala Gly Leu Phe Asn Ser Pro
            20                  25                  30

Glu Thr Thr Thr Asp Ser Ser Gly Asp Asp Leu Ala Lys Asp Ser Gly
        35                  40                  45

Ser Asp Asp Ser Ile Ser Ser Asp Ala Ala Asn Ser Gln Pro Gln Gln
    50                  55                  60

Lys Gln Asp Thr Asp Phe Ser Val Leu Lys Phe Ala Tyr Arg Pro Ser
65                  70                  75                  80

Val Pro Ala His Arg Lys Val Lys Glu Ser Pro Leu Ser Ser Asp Thr
                85                  90                  95

Ile Phe Arg Gln Ser His Ala Gly Leu Phe Asn Leu Cys Ile Val Val
            100                 105                 110

Leu Val Ala Val Asn Ser Arg Leu Ile Ile Glu Asn Leu Met Lys Tyr
        115                 120                 125

Gly Trp Leu Ile Lys Ser Gly Phe Trp Phe Ser Ser Lys Ser Leu Arg
    130                 135                 140

Asp Trp Pro Leu Phe Met Cys Cys Leu Ser Leu Val Val Phe Pro Phe
145                 150                 155                 160

Ala Ala Phe Ile Val Glu Lys Leu Ala Gln Gln Lys Cys Ile Pro Glu
                165                 170                 175

Pro Val Val Val Val Leu His Ile Ile Ile Thr Ser Ala Ser Leu Phe
```

```
            180                 185                 190

Tyr Pro Val Leu Val Ile Leu Arg Cys Asp Ser Ala Phe Leu Ser Gly
        195                 200                 205

Val Thr Leu Met Leu Phe Ala Cys Val Val Trp Leu Lys Leu Val Ser
    210                 215                 220

Tyr Ala His Thr Asn Tyr Asp Met Arg Ala Leu Thr Lys Ser Val Glu
225                 230                 235                 240

Lys Gly Glu Ala Leu Pro Asp Thr Leu Asn Met Asp Tyr Pro Tyr Asn
                245                 250                 255

Val Ser Phe Lys Ser Leu Ala Tyr Phe Leu Val Ala Pro Thr Leu Cys
            260                 265                 270

Tyr Gln Pro Ser Tyr Pro Arg Thr Pro Tyr Ile Arg Lys Gly Trp Leu
        275                 280                 285

Phe Arg Gln Leu Val Lys Leu Ile Ile Phe Thr Gly Val Met Gly Phe
    290                 295                 300

Ile Ile Glu Gln Tyr Ile Asn Pro Ile Val Gln Asn Ser Gln His Pro
305                 310                 315                 320

Leu Lys Gly Asn Leu Leu Tyr Ala Ile Glu Arg Val Leu Lys Leu Ser
                325                 330                 335

Val Pro Asn Leu Tyr Val Trp Leu Cys Met Phe Tyr Cys Phe Phe His
            340                 345                 350

Leu Trp Leu Asn Ile Leu Ala Glu Leu Leu Arg Phe Gly Asp Arg Glu
        355                 360                 365

Phe Tyr Gln Asp Trp Trp Asn Ala Lys Thr Val Glu Asp Tyr Trp Arg
    370                 375                 380

Met Trp Asn Met Pro Val His Lys Trp Met Ile Arg His Leu Tyr Phe
385                 390                 395                 400

Pro Cys Leu Arg His Gly Ile Pro Lys Ala Val Ala Leu Leu Ile Ala
                405                 410                 415

Phe Leu Val Ser Ala Leu Phe His Glu Leu Cys Ile Ala Val Pro Cys
            420                 425                 430

His Ile Phe Lys Leu Trp Ala Phe Gly Gly Ile Met Phe Gln Val Pro
        435                 440                 445

Leu Val Phe Ile Thr Asn Tyr Leu Gln Asn Lys Phe Arg Asn Ser Met
    450                 455                 460

Val Gly Asn Met Ile Phe Trp Phe Ile Phe Ser Ile Leu Gly Gln Pro
465                 470                 475                 480

Met Cys Val Leu Leu Tyr Tyr His Asp Leu Met Asn Arg Lys Gly Lys
                485                 490                 495

Leu Asp
```

<210> SEQ ID NO 5
<211> LENGTH: 1554
<212> TYPE: DNA
<213> ORGANISM: Glycine max

<400> SEQUENCE: 5

```
atggcgatct ccgatgtgcc tgcagccgct ggcacgaccg ccactaccac cagcgactca     60

gatctccgac agccttctct gcggcgcagg tcctccgccg gagtcctctt cgacgctgcc    120

agagattccg gctccgacaa ttccctgacc ggcaaaatca ccgacgacga caacatcaaa    180

gatcacaagc cgaataatca cgcagcctcc gacgacaatg tgggcgccgc cgccaatgac    240

gctgggcagg agcaccgaca accggtcgcc gatttcaaat acgcttaccg tccctccgtt    300
```

```
cccgcgcacc gcagaatcaa ggagagcccc cttagctccg acaacatctt cagacagagt    360

catgcaggac tgttcaatct ctgcatagta gtgcttgttg ccgtgaacag cagacttatc    420

attgagaatt taatgaagta tggttggttg atcaagtatg gcttttggtt tagttcaaaa    480

tcattgagag attggcctct cttcatgtgc tgtcttagtc ttgccatatt tccacttgct    540

gcctttgttg tggaaaggtt ggcacaacaa aagtgtattt ctgaaccagt tgttgttcta    600

cttcatctaa taatatcaac tgttgaactg tgctatccgg ttttagtaat actcaggtgt    660

gattctgctt ttgtatctgg tgtcacgttg atgctattaa cttgcattgt gtggttaaaa    720

ttggtgtcat atgcacatac aaactatgat atgagagcac ttactgtttc gaatgaaaag    780

ggagaaacat tacccaatac tttgattatg gagtatccgt acactgtgac cttcaggagt    840

ttggcatact tcatggttgc tcctacatta tgctatcaga caagctatcc tcgcacacct    900

tcagttcgaa agggttgggt gtttcgtcaa cttgtcaagc tgataatatt tacaggagtt    960

atgggattta taatagaaca atatatgaat cctattgtac aaaactcaac tcatcctttg   1020

aagggaaacc ttctatatgc cattgagaga attctgaagc tttctgtccc aaatgtatat   1080

gtgtggctct gcatgttcta ctgctttttc cacctttggt taaatatact tgcagagctt   1140

gttcgatttg gtgatcgtga gttctataaa gattggtgga atgccaaaac tgttgaagag   1200

tattggagga tgtggaatat gcctgtgcac aaatggatgg ttcgccacat atattttcca   1260

tgcttaaggc gtggtatacc caagggtgct gcttcattaa ttgcattcct ggtttctgct   1320

gtgtttcatg agttatgcat tgccgttcct tgccacatgt tcaagttgtg ggcttttata   1380

ggaattatgt ttcaggttcc tttggtcttg atcactaatt acctccaaaa taaatacaga   1440

aactcaatgg ttggaaatat gatttttttgg ttcatatttt gtattcttgg tcaaccaatg   1500

agcgtactat tgtactacca tgacttgatg aatagaaaag gagaagttga ctaa          1554
```

```
<210> SEQ ID NO 6
<211> LENGTH: 517
<212> TYPE: PRT
<213> ORGANISM: Glycine max

<400> SEQUENCE: 6

Met Ala Ile Ser Asp Val Pro Ala Ala Ala Gly Thr Thr Ala Thr Thr
1               5                   10                  15

Thr Ser Asp Ser Asp Leu Arg Gln Pro Ser Leu Arg Arg Arg Ser Ser
            20                  25                  30

Ala Gly Val Leu Phe Asp Ala Ala Arg Asp Ser Gly Ser Asp Asn Ser
        35                  40                  45

Leu Thr Gly Lys Ile Thr Asp Asp Asp Asn Ile Lys Asp His Lys Pro
    50                  55                  60

Asn Asn His Ala Ala Ser Asp Asp Asn Val Gly Ala Ala Ala Asn Asp
65                  70                  75                  80

Ala Gly Gln Glu His Arg Gln Pro Val Ala Asp Phe Lys Tyr Ala Tyr
                85                  90                  95

Arg Pro Ser Val Pro Ala His Arg Arg Ile Lys Glu Ser Pro Leu Ser
            100                 105                 110

Ser Asp Asn Ile Phe Arg Gln Ser His Ala Gly Leu Phe Asn Leu Cys
        115                 120                 125

Ile Val Val Leu Val Ala Val Asn Ser Arg Leu Ile Ile Glu Asn Leu
    130                 135                 140

Met Lys Tyr Gly Trp Leu Ile Lys Tyr Gly Phe Trp Phe Ser Ser Lys
145                 150                 155                 160
```

```
Ser Leu Arg Asp Trp Pro Leu Phe Met Cys Cys Leu Ser Leu Ala Ile
                165                 170                 175

Phe Pro Leu Ala Ala Phe Val Val Glu Arg Leu Ala Gln Gln Lys Cys
            180                 185                 190

Ile Ser Glu Pro Val Val Val Leu Leu His Leu Ile Ile Ser Thr Val
        195                 200                 205

Glu Leu Cys Tyr Pro Val Leu Val Ile Leu Arg Cys Asp Ser Ala Phe
    210                 215                 220

Val Ser Gly Val Thr Leu Met Leu Leu Thr Cys Ile Val Trp Leu Lys
225                 230                 235                 240

Leu Val Ser Tyr Ala His Thr Asn Tyr Asp Met Arg Ala Leu Thr Val
                245                 250                 255

Ser Asn Glu Lys Gly Glu Thr Leu Pro Asn Thr Leu Ile Met Glu Tyr
            260                 265                 270

Pro Tyr Thr Val Thr Phe Arg Ser Leu Ala Tyr Phe Met Val Ala Pro
        275                 280                 285

Thr Leu Cys Tyr Gln Thr Ser Tyr Pro Arg Thr Pro Ser Val Arg Lys
    290                 295                 300

Gly Trp Val Phe Arg Gln Leu Val Lys Leu Ile Ile Phe Thr Gly Val
305                 310                 315                 320

Met Gly Phe Ile Ile Glu Gln Tyr Met Asn Pro Ile Val Gln Asn Ser
                325                 330                 335

Thr His Pro Leu Lys Gly Asn Leu Leu Tyr Ala Ile Glu Arg Ile Leu
            340                 345                 350

Lys Leu Ser Val Pro Asn Val Tyr Val Trp Leu Cys Met Phe Tyr Cys
        355                 360                 365

Phe Phe His Leu Trp Leu Asn Ile Leu Ala Glu Leu Val Arg Phe Gly
    370                 375                 380

Asp Arg Glu Phe Tyr Lys Asp Trp Trp Asn Ala Lys Thr Val Glu Glu
385                 390                 395                 400

Tyr Trp Arg Met Trp Asn Met Pro Val His Lys Trp Met Val Arg His
                405                 410                 415

Ile Tyr Phe Pro Cys Leu Arg Arg Gly Ile Pro Lys Gly Ala Ala Ser
            420                 425                 430

Leu Ile Ala Phe Leu Val Ser Ala Val Phe His Glu Leu Cys Ile Ala
        435                 440                 445

Val Pro Cys His Met Phe Lys Leu Trp Ala Phe Ile Gly Ile Met Phe
    450                 455                 460

Gln Val Pro Leu Val Leu Ile Thr Asn Tyr Leu Gln Asn Lys Tyr Arg
465                 470                 475                 480

Asn Ser Met Val Gly Asn Met Ile Phe Trp Phe Ile Phe Cys Ile Leu
                485                 490                 495

Gly Gln Pro Met Ser Val Leu Leu Tyr Tyr His Asp Leu Met Asn Arg
            500                 505                 510

Lys Gly Glu Val Asp
        515


<210> SEQ ID NO 7
<211> LENGTH: 1509
<212> TYPE: DNA
<213> ORGANISM: Brassica napus

<400> SEQUENCE: 7

atggcggttt tggattctgg aggcgtcgct gtgccgacgg agaacggcgt cgcggatctc      60
```

```
gacaggctcc atcgtcgtaa atcgagatcg gattcttcca acggactcct ccccgatact    120

tccccgtcgg acgatgttgg agctgcggcg gccgaaaggg atcgggttga ttccgctgcc    180

gaggaggagg ctcagggaac agcgaattta gctggcggag atgccgaaac tagggaatcc    240

gccggaggcg atgtaaggtt tacgtatcga ccgtcggttc cagctcatcg gaggacgagg    300

gagagtcctc tcagctctga cgctatcttc aaacaaagcc atgcaggatt gttcaacctc    360

tgtgtagttg ttcttgttgc tgttaacagt agactcatca tcgaaaacct catgaagtat    420

ggttggttga tcagaactga tttttggttt agttctacat ccttacgaga ctggccgctt    480

ttcatgtgtt gtctttcact ttcggtcttt cctttggctg ccttcacggt cgagaaaatg    540

gtacttcaga gattcatatc tgagcctgtt gccatcattc ttcatgttat tataaccttg    600

acagaggtct tgtatccagt ctacgtcaca ctgaggtgtg attctgcctt cttgtcaggt    660

gtcacgttga tgctgctcac ttgcattgtg tggctgaagt tggtttctta cgctcatact    720

agctacgaca taagaaccct agctaattca gctgataagg tcgatcctga aatctcctac    780

catgttagct tgaagagctt ggcgtatttc atggttgctc ctacactgtg ttatcagcca    840

agctatccac gttccccatg tatacggaag ggttgggtgg ctcgtcaatt tgcgaaactg    900

gtcatattca ctggactcat gggatttata atagagcagt atataaatcc tattgtaagg    960

aactcaaagc atccgttgaa aggggatctt ctatacgcta ttgaaagagt gttgaagctt   1020

tcagttccaa atctatatgt gtggctctgc atgttctact gcttcttcca cctttggtta   1080

aacatattgg cagagctgct ctgcttcggg gaccgtgaat tctacaaaga ttggtggaat   1140

gcaaaaagcg ttggagatta ttggagaatg tggaatatgc ctgttcataa atggatggtt   1200

cgacatgtat actttccgtg cctgcgcatc aagataccaa aagtacccgc cattatcatt   1260

gctttcttag tctctgcagt ctttcatgag ttatgcatcg cagttccttg ccgtctcttc   1320

aatctatggg ctttcatggg aattatgttt caggtccctt tggtctttat cacaaacttt   1380

ttacaagaaa ggtttggctc catggtggga aacatgatct tctggttcag cttctgcatt   1440

ttcggacaac ccatgtgtgt tcttctttat taccatgacc tgatgaaccg caaaggatcc   1500

atgtcctga                                                           1509
```

```
<210> SEQ ID NO 8
<211> LENGTH: 503
<212> TYPE: PRT
<213> ORGANISM: Brassica napus

<400> SEQUENCE: 8

Met Ala Ile Leu Asp Ser Gly Gly Val Ala Val Pro Pro Thr Glu Asn
1               5                   10                  15

Gly Val Ala Asp Leu Asp Arg Leu His Arg Arg Lys Ser Ser Ser Asp
            20                  25                  30

Ser Ser Asn Gly Leu Leu Ser Asp Thr Ser Pro Ser Asp Asp Val Gly
        35                  40                  45

Ala Ala Ala Ala Glu Arg Asp Arg Val Asp Ser Ala Ala Glu Glu Glu
    50                  55                  60

Ala Gln Gly Thr Ala Asn Leu Ala Gly Gly Asp Ala Glu Thr Arg Glu
65                  70                  75                  80

Ser Ala Gly Gly Asp Val Arg Phe Thr Tyr Arg Pro Ser Val Pro Ala
                85                  90                  95

His Arg Arg Thr Arg Glu Ser Pro Leu Ser Ser Asp Ala Ile Phe Lys
            100                 105                 110
```

```
Gln Ser His Ala Gly Leu Phe Asn Leu Cys Val Val Val Leu Val Ala
        115                 120                 125

Val Asn Ser Arg Leu Ile Ile Glu Asn Leu Met Lys Tyr Gly Trp Leu
    130                 135                 140

Ile Arg Thr Asp Phe Trp Phe Ser Ser Thr Ser Leu Arg Asp Trp Pro
145                 150                 155                 160

Leu Phe Met Cys Cys Leu Ser Leu Ser Val Phe Pro Leu Ala Ala Phe
                165                 170                 175

Thr Val Glu Lys Met Val Leu Gln Lys Phe Ile Ser Glu Pro Val Ala
            180                 185                 190

Ile Ile Leu His Val Ile Ile Thr Met Thr Glu Val Leu Tyr Pro Val
        195                 200                 205

Tyr Val Thr Leu Arg Cys Asp Ser Ala Phe Leu Ser Gly Val Thr Leu
    210                 215                 220

Met Leu Leu Thr Cys Ile Val Trp Leu Lys Leu Val Ser Tyr Ala His
225                 230                 235                 240

Thr Ser Tyr Asp Ile Arg Thr Leu Ala Asn Ser Ala Asp Lys Val Asp
                245                 250                 255

Pro Glu Ile Ser Tyr Tyr Val Ser Leu Lys Ser Leu Ala Tyr Phe Met
            260                 265                 270

Val Ala Pro Thr Leu Cys Tyr Gln Pro Ser Tyr Pro Arg Ser Pro Cys
        275                 280                 285

Ile Arg Lys Gly Trp Val Ala Arg Gln Leu Ala Lys Leu Val Ile Phe
    290                 295                 300

Thr Gly Leu Met Gly Phe Ile Ile Glu Gln Tyr Ile Asn Pro Ile Val
305                 310                 315                 320

Arg Asn Ser Lys His Pro Leu Lys Gly Asp Leu Leu Tyr Ala Ile Glu
                325                 330                 335

Arg Val Leu Lys Leu Ser Val Pro Asn Leu Tyr Val Trp Leu Cys Met
            340                 345                 350

Phe Tyr Cys Phe Phe His Leu Trp Leu Asn Ile Leu Ala Glu Leu Leu
        355                 360                 365

Cys Phe Gly Asp Arg Glu Phe Tyr Lys Asp Trp Trp Asn Ala Lys Ser
    370                 375                 380

Val Gly Asp Tyr Trp Arg Met Trp Asn Met Pro Val His Lys Trp Met
385                 390                 395                 400

Val Arg His Val Tyr Phe Pro Cys Leu Arg Ile Lys Ile Pro Lys Val
                405                 410                 415

Pro Ala Ile Ile Ile Ala Phe Leu Val Ser Ala Val Phe His Glu Leu
            420                 425                 430

Cys Ile Ala Val Pro Cys Arg Leu Phe Asn Leu Trp Ala Phe Met Gly
        435                 440                 445

Ile Met Phe Gln Val Pro Leu Val Phe Ile Thr Asn Phe Leu Gln Glu
    450                 455                 460

Arg Phe Gly Ser Met Val Gly Asn Met Ile Phe Gly Ser Ala Ser Cys
465                 470                 475                 480

Ile Phe Gly Gln Pro Met Cys Gly Leu Leu Tyr Tyr His Asp Leu Met
                485                 490                 495

Asn Arg Lys Gly Ser Met Ser
            500
```

<210> SEQ ID NO 9
<211> LENGTH: 1509

<212> TYPE: DNA
<213> ORGANISM: Gossypium hirsutum

<400> SEQUENCE: 9

```
atggcgatgt ttgagtcacc ggagatttca gggagtagta cggcgacggt gatcggtacc      60

tcacgtagcg agtcagatct taatcatttt gcgccccgtc gtcgagccgt gaataacgcc     120

gtcgatgcag ggactagagt tgtggagcgt aacaattccg gtaatggcga gacagtggac     180

gctagggatc gaatggaatc ggctaatttc tcgagggaaa acgtgaatga gaatccgact     240

aattcagata cgaggttcac gtatcggcct tctgttcctg ctcattggag gatcaaagaa     300

agccctctca gctctgacaa tatcttccaa cagagtcatg caggcctgtt taacctatgt     360

gttgtagtgc ttgttgctgt aaacagccgg cttattattg agaacctgat gaagtatggg     420

tggttgatca gaactggctt ttggtttagt tcgagatcat tgagggattg gcctcttttt     480

atgtgctgtc tttctctccc aatattccca atcgcggcct ttgtagttga aaagttgttg     540

caacagaatc aaatatctga acgaactctt attttacttc atatactgat tagcacgctt     600

gcagttctat atccagttgt tgttattctc aggtgtgatt ctgcattctt atcaggcatt     660

gcattgatgc tatttgcttg cattgtctgg ttaaaattgg tatcctatgc tcatactaac     720

agtgatatga gatcagttgc gaagtcgact gaaaagggaa gtgaaggctg catgtacaat     780

gttagcttca ggagtctggc atacttcatg gcagctccca cattatgtta ccagacaagc     840

tatcctcgta ctgcatcaat tagaaaaaat tgggtggttc gtcaatttat caagttaata     900

atatttactg gactcatggg tttcataata gaacagtata tcaatccaat tgttcagaac     960

tctcagcacc ctttgaaggc gaacttttta tatgccatag aaagaatttt gaagctttca    1020

gttccaaata catatgtctg gctttgcatg ttctacagct tctttcatct ctggttaaat    1080

atactggctg agcttcttcg ttttggggac cgcgagtttt ataaagattg gtggaatgca    1140

aaaactgttg aggagtattg gagaatgtgg aatatgcctg ttcataaatg gatggttcgc    1200

catatctatt tgccatgctt aaggaacggt ataccaaagg gagttgccat tcttatcgcc    1260

ttcttggttt ctgctatatt tcatgagctc tgcattgctg ttccttgcca cttatttaag    1320

ttatgggctt tctttggcat catgtttcag gctcccttgg tcttgatcac tagttatctt    1380

caaaataagt tccagagttc aatggtggga aatatgatat tctggttcat attctgcatt    1440

cttggtcaac caacgtgcgt acttttatat tatcatgatt tgatgaatcg caaaggatcg    1500

gcagattaa                                                           1509
```

<210> SEQ ID NO 10
<211> LENGTH: 502
<212> TYPE: PRT
<213> ORGANISM: Gossypium hirsutum

<400> SEQUENCE: 10

```
Met Ala Met Phe Glu Ser Pro Glu Ile Ser Gly Ser Ser Thr Ala Thr
1               5                   10                  15

Val Ile Gly Thr Ser Arg Ser Glu Ser Asp Leu Asn His Phe Ala Pro
            20                  25                  30

Arg Arg Arg Ala Val Asn Asn Ala Val Asp Ala Gly Thr Arg Val Val
        35                  40                  45

Glu Arg Asn Asn Ser Gly Asn Gly Glu Thr Val Asp Ala Arg Asp Arg
    50                  55                  60

Met Glu Ser Ala Asn Phe Ser Arg Glu Asn Val Asn Glu Asn Pro Thr
65                  70                  75                  80
```

-continued

```
Asn Ser Asp Thr Arg Phe Thr Tyr Arg Pro Ser Val Pro Ala His Trp
                85                  90                  95

Arg Ile Lys Glu Ser Pro Leu Ser Ser Asp Asn Ile Phe Gln Gln Ser
            100                 105                 110

His Ala Gly Leu Phe Asn Leu Cys Val Val Val Leu Val Ala Val Asn
        115                 120                 125

Ser Arg Leu Ile Ile Glu Asn Leu Met Lys Tyr Gly Trp Leu Ile Arg
    130                 135                 140

Thr Gly Phe Trp Phe Ser Ser Arg Ser Leu Arg Asp Trp Pro Leu Phe
145                 150                 155                 160

Met Cys Cys Leu Ser Leu Pro Ile Phe Pro Ile Ala Ala Phe Val Val
                165                 170                 175

Glu Lys Leu Leu Gln Gln Asn Gln Ile Ser Glu Arg Thr Leu Ile Leu
            180                 185                 190

Leu His Ile Leu Ile Ser Thr Leu Ala Val Leu Tyr Pro Val Val Val
        195                 200                 205

Ile Leu Arg Cys Asp Ser Ala Phe Leu Ser Gly Ile Ala Leu Met Leu
    210                 215                 220

Phe Ala Cys Ile Val Trp Leu Lys Leu Val Ser Tyr Ala His Thr Asn
225                 230                 235                 240

Ser Asp Met Arg Ser Val Ala Lys Ser Thr Glu Lys Gly Ser Glu Gly
                245                 250                 255

Cys Met Tyr Asn Val Ser Phe Arg Ser Leu Ala Tyr Phe Met Ala Ala
            260                 265                 270

Pro Thr Leu Cys Tyr Gln Thr Ser Tyr Pro Arg Thr Ala Ser Ile Arg
        275                 280                 285

Lys Asn Trp Val Val Arg Gln Phe Ile Lys Leu Ile Ile Phe Thr Gly
    290                 295                 300

Leu Met Gly Phe Ile Ile Glu Gln Tyr Ile Asn Pro Ile Val Gln Asn
305                 310                 315                 320

Ser Gln His Pro Leu Lys Ala Asn Phe Leu Tyr Ala Ile Glu Arg Ile
                325                 330                 335

Leu Lys Leu Ser Val Pro Asn Thr Tyr Val Trp Leu Cys Met Phe Tyr
            340                 345                 350

Ser Phe Phe His Leu Trp Leu Asn Ile Leu Ala Glu Leu Leu Arg Phe
        355                 360                 365

Gly Asp Arg Glu Phe Tyr Lys Asp Trp Trp Asn Ala Lys Thr Val Glu
    370                 375                 380

Glu Tyr Trp Arg Met Trp Asn Met Pro Val His Lys Trp Met Val Arg
385                 390                 395                 400

His Ile Tyr Leu Pro Cys Leu Arg Asn Gly Ile Pro Lys Gly Val Ala
                405                 410                 415

Ile Leu Ile Ala Phe Leu Val Ser Ala Ile Phe His Glu Leu Cys Ile
            420                 425                 430

Ala Val Pro Cys His Leu Phe Lys Leu Trp Ala Phe Phe Gly Ile Met
        435                 440                 445

Phe Gln Ala Pro Leu Val Leu Ile Thr Ser Tyr Leu Gln Asn Lys Phe
    450                 455                 460

Gln Ser Ser Met Val Gly Asn Met Ile Phe Trp Phe Ile Phe Cys Ile
465                 470                 475                 480

Leu Gly Gln Pro Thr Cys Val Leu Leu Tyr Tyr His Asp Leu Met Asn
                485                 490                 495
```

Arg Lys Gly Ser Ala Asp
500

<210> SEQ ID NO 11
<211> LENGTH: 1554
<212> TYPE: DNA
<213> ORGANISM: Helianthus annuus

<400> SEQUENCE: 11
atggcgttac tagatacgtc agatatcgga gactccaccg ccatacgcgg cgagataaga 60
cggcggagga gcgtgaagcc tgatgccgga ttcggaatcg gagacggttt gtatgattct 120
tcatcgtctt ctcgaacgaa ctcgtctgaa gaagaaggtg agagtttgac taacggtttc 180
gatgaaaatg aacggatccg agctggtgat gaaactcaaa caacacagga aaataaacag 240
aagacagatc agagaagaga taaaacgagt ctgttgcaat atgcgtatcg tgcttcttct 300
ccagcgcatc gtagaattaa agagtctccg cttagctccg atgctatctt caagcagagt 360
catgcaggcc tttttaacct ttgcatagtg gtgcttgttg ctgtaaatgg taggctcatt 420
attgagaatc tgatgaagta cggattattg atcaattcca atttttggtt cagttcaaga 480
tcattaagag attggcccct tctgatgtgc tgcgtctctc ttctgttctt ccctcttgct 540
gcttacattg ttgagaaatt ggcatggaaa aaacgtatat cagaccctgt tgtaatcact 600
ctccatgtta tagtaactac aactgcgatt ttatatccgg ttttcatgat tctgagggtt 660
gattcagttg ttctatcagg tgtttcattg atgctgtgtg cttgcatcaa ttggttaaaa 720
ttgacatctt ttgtgcatac tagttatgac atgcggtccc ttgtgaattc aaccgataag 780
ggagagacag agtccgagtc tttagatata gagttatttt atgatgctga cttcaaaagc 840
ttggtttatt tcttgcttgc tcctactttg tgttaccagt tacgctatcc ccgcactgca 900
tttattcgaa agggttgggt gttacggcaa ctgatcaagc taataatatt tacagggtta 960
atgggattca tcattgaaca atatatcaat ccgattgtac aaaactctca gcatccattg 1020
aacggcgaca ttttatacgc aattgaacgt gttttaaagc tttcagttcc aaatttatac 1080
gtttggctct gtatgttcta ctgttttttt cacctttggt tgaatatact tgctgagctt 1140
cttcgttttg ggatcgtgga gttttataaa gattggtgga atgcacaaac tattgaagag 1200
tattggagac tatggaatat gcctgttcat aaatggattg tacggcatct ctacttccca 1260
tgcttgcgta atgggatacc taagggtgct gccatcttgg ttgcgttttt catgtctgct 1320
gtgttccatg agctttgtat tgctgttccc tgccacattt tcaaattttg ggcttttatt 1380
gggatcatgt ttcaggtgcc cttggtctta ctcacgaatt acttgcagaa caagttccaa 1440
aactcaatgg ttggaaatat aatcttctgg tgcttcttta gcatccttgg tcaacccatg 1500
tgtgtattac tctactatca tgatgtcatg aatcaaaagg tgaatagcaa ataa 1554

<210> SEQ ID NO 12
<211> LENGTH: 517
<212> TYPE: PRT
<213> ORGANISM: Helianthus annuus

<400> SEQUENCE: 12

Met Ala Leu Leu Asp Thr Ser Asp Ile Gly Asp Ser Thr Ala Ile Arg
1 5 10 15

Gly Glu Ile Arg Arg Arg Arg Ser Val Lys Pro Asp Ala Gly Phe Gly
20 25 30

Ile Gly Asp Gly Leu Tyr Asp Ser Ser Ser Ser Ser Arg Thr Asn Ser
35 40 45

-continued

```
Ser Glu Glu Glu Gly Glu Ser Leu Thr Asn Gly Phe Asp Glu Asn Glu
    50                  55                  60

Arg Ile Arg Ala Gly Asp Glu Thr Gln Thr Thr Gln Glu Asn Lys Gln
65                  70                  75                  80

Lys Thr Asp Gln Arg Arg Asp Lys Thr Ser Leu Leu Gln Tyr Ala Tyr
                85                  90                  95

Arg Ala Ser Ser Pro Ala His Arg Arg Ile Lys Glu Ser Pro Leu Ser
            100                 105                 110

Ser Asp Ala Ile Phe Lys Gln Ser His Ala Gly Leu Phe Asn Leu Cys
        115                 120                 125

Ile Val Val Leu Val Ala Val Asn Gly Arg Leu Ile Ile Glu Asn Leu
    130                 135                 140

Met Lys Tyr Gly Leu Leu Ile Asn Ser Asn Phe Trp Phe Ser Ser Arg
145                 150                 155                 160

Ser Leu Arg Asp Trp Pro Leu Leu Met Cys Cys Val Ser Leu Leu Phe
                165                 170                 175

Phe Pro Leu Ala Ala Tyr Ile Val Glu Lys Leu Ala Trp Lys Lys Arg
            180                 185                 190

Ile Ser Asp Pro Val Val Ile Thr Leu His Val Ile Val Thr Thr Thr
        195                 200                 205

Ala Ile Leu Tyr Pro Val Phe Met Ile Leu Arg Val Asp Ser Val Val
    210                 215                 220

Leu Ser Gly Val Ser Leu Met Leu Cys Ala Cys Ile Asn Trp Leu Lys
225                 230                 235                 240

Leu Thr Ser Phe Val His Thr Ser Tyr Asp Met Arg Ser Leu Val Asn
                245                 250                 255

Ser Thr Asp Lys Gly Glu Thr Glu Ser Glu Ser Leu Asp Ile Glu Leu
            260                 265                 270

Phe Tyr Asp Ala Asp Phe Lys Ser Leu Val Tyr Phe Leu Leu Ala Pro
        275                 280                 285

Thr Leu Cys Tyr Gln Leu Arg Tyr Pro Arg Thr Ala Phe Ile Arg Lys
    290                 295                 300

Gly Trp Val Leu Arg Gln Leu Ile Lys Leu Ile Ile Phe Thr Gly Leu
305                 310                 315                 320

Met Gly Phe Ile Ile Glu Gln Tyr Ile Asn Pro Ile Val Gln Asn Ser
                325                 330                 335

Gln His Pro Leu Asn Gly Asp Ile Leu Tyr Ala Ile Glu Arg Val Leu
            340                 345                 350

Lys Leu Ser Val Pro Asn Leu Tyr Val Trp Leu Cys Met Phe Tyr Cys
        355                 360                 365

Phe Phe His Leu Trp Leu Asn Ile Leu Ala Glu Leu Leu Arg Phe Gly
    370                 375                 380

Asp Arg Glu Phe Tyr Lys Asp Trp Trp Asn Ala Gln Thr Ile Glu Glu
385                 390                 395                 400

Tyr Trp Arg Leu Trp Asn Met Pro Val His Lys Trp Ile Val Arg His
                405                 410                 415

Leu Tyr Phe Pro Cys Leu Arg Asn Gly Ile Pro Lys Gly Ala Ala Ile
            420                 425                 430

Leu Val Ala Phe Phe Met Ser Ala Val Phe His Glu Leu Cys Ile Ala
        435                 440                 445

Val Pro Cys His Ile Phe Lys Phe Trp Ala Phe Ile Gly Ile Met Phe
    450                 455                 460
```

```
Gln Val Pro Leu Val Leu Leu Thr Asn Tyr Leu Gln Asn Lys Phe Gln
465                 470                 475                 480

Asn Ser Met Val Gly Asn Ile Ile Phe Trp Cys Phe Phe Ser Ile Leu
                485                 490                 495

Gly Gln Pro Met Cys Val Leu Leu Tyr Tyr His Asp Val Met Asn Gln
            500                 505                 510

Lys Val Asn Ser Lys
        515


<210> SEQ ID NO 13
<211> LENGTH: 1416
<212> TYPE: DNA
<213> ORGANISM: Hordeum vulgare

<400> SEQUENCE: 13

atggccccgc ccccgtccgt ggccgctgcc cacgactgcg acgacccctc cctccgcctc     60

cgccgcgccg acggcggctc ctccggcgtc cacggagagg cgcgtccgca ggagcagccg    120

cagcggcagc acgagatgcc ctgctaccgg gcgtccgcgc ccgcacaccg ccgggtgaag    180

gagagcccgc tcagctccga cgccatcttc cgacagagcc atgcaggtct tctgaatcta    240

tgcattgttg tgctgattgc agtgaacagc aggctcatta tcgagaactt aatgaagtat    300

ggcttattaa taagagctgg attttggttt agtgcaagat cgctgggaga ttggccactt    360

ctgatgtgct gcctaacttt accaatttc ccacttgctg cactcatgac cgagaagtgg    420

gctcaaagaa agctcattcg tgatcatgtg tctattcttc tccatatcat tattacagcc    480

actgtcctta tctatccggt tgttgtgatt cttaagtgtg aatcagcagt attatctgga    540

tttgtgttaa tgttcattgc aagcattact tggttgaagc ttgtctcttt tgctcataca    600

aatcatgata taagggtatt gtcccaaagt attgaaaagg gtgctacaca tggcagttcc    660

atcgatgaag aaaccattaa aggtccaact accaacagtg ttgtgtattt catgttggcc    720

ccaacacttt gttaccagcc aagttatccc cggacagcat ttgttaggaa aggctgggtg    780

gcccagcagc ttataaaatg catagttttt acaggcttga tgggcttcat aattgagcaa    840

tacattaatc caattgtgca gaattccaag catccattga aaggaaattt cttggatgct    900

attgagagag tcctgaaact ctcagtgccg acattgtatg tatggctttg tatgttctat    960

tgctttttcc atctgtggtt gaatattctt gccgaactcc tccgttttgg tgatcgtgaa   1020

ttctataagg actggtggaa tgccagaaca gttgaagagt actggagaat gtggaatatg   1080

cctgttcata agtggatcgt tcgacatata tattttccat gcataaggaa tggcttgtca   1140

aagggttgtg ccattctcat ctcatttctt gtttcagctg tatttcatga gctatgtatt   1200

gctgttccgt gccacatttt caaactatgg gcattttctg gaatcatgtt tcagattccc   1260

ctgctattct tgacgaagta tcttcaagat aagttcaaga atacaatggc gggcaacatg   1320

atattttggt tcttcttcag catagttggg cagccaatgt gtgttctctt gtactaccac   1380

gatgtcatga acagacaagc tcagacaaat ggctag                             1416


<210> SEQ ID NO 14
<211> LENGTH: 471
<212> TYPE: PRT
<213> ORGANISM: Hordeum vulgare

<400> SEQUENCE: 14

Met Ala Pro Pro Pro Ser Val Ala Ala Ala His Asp Cys Asp Asp Pro
1               5                   10                  15
```

```
Ser Leu Arg Leu Arg Arg Ala Asp Gly Gly Ser Ser Gly Val His Gly
            20                  25                  30

Glu Ala Arg Pro Gln Glu Gln Pro Gln Arg Gln His Glu Met Pro Cys
        35                  40                  45

Tyr Arg Ala Ser Ala Pro Ala His Arg Arg Val Lys Glu Ser Pro Leu
    50                  55                  60

Ser Ser Asp Ala Ile Phe Arg Gln Ser His Ala Gly Leu Leu Asn Leu
65                  70                  75                  80

Cys Ile Val Val Leu Ile Ala Val Asn Ser Arg Leu Ile Ile Glu Asn
                85                  90                  95

Leu Met Lys Tyr Gly Leu Leu Ile Arg Ala Gly Phe Trp Phe Ser Ala
            100                 105                 110

Arg Ser Leu Gly Asp Trp Pro Leu Leu Met Cys Cys Leu Thr Leu Pro
        115                 120                 125

Ile Phe Pro Leu Ala Ala Leu Met Thr Glu Lys Trp Ala Gln Arg Lys
    130                 135                 140

Leu Ile Arg Asp His Val Ser Ile Leu Leu His Ile Ile Ile Thr Ala
145                 150                 155                 160

Thr Val Leu Ile Tyr Pro Val Val Val Ile Leu Lys Cys Glu Ser Ala
                165                 170                 175

Val Leu Ser Gly Phe Val Leu Met Phe Ile Ala Ser Ile Thr Trp Leu
            180                 185                 190

Lys Leu Val Ser Phe Ala His Thr Asn His Asp Ile Arg Val Leu Ser
        195                 200                 205

Gln Ser Ile Glu Lys Gly Ala Thr His Gly Ser Ser Ile Asp Glu Glu
    210                 215                 220

Thr Ile Lys Gly Pro Thr Thr Asn Ser Val Val Tyr Phe Met Leu Ala
225                 230                 235                 240

Pro Thr Leu Cys Tyr Gln Pro Ser Tyr Pro Arg Thr Ala Phe Val Arg
                245                 250                 255

Lys Gly Trp Val Ala Gln Gln Leu Ile Lys Cys Ile Val Phe Thr Gly
            260                 265                 270

Leu Met Gly Phe Ile Ile Glu Gln Tyr Ile Asn Pro Ile Val Gln Asn
        275                 280                 285

Ser Lys His Pro Leu Lys Gly Asn Phe Leu Asp Ala Ile Glu Arg Val
    290                 295                 300

Leu Lys Leu Ser Val Pro Thr Leu Tyr Val Trp Leu Cys Met Phe Tyr
305                 310                 315                 320

Cys Phe Phe His Leu Trp Leu Asn Ile Leu Ala Glu Leu Leu Arg Phe
                325                 330                 335

Gly Asp Arg Glu Phe Tyr Lys Asp Trp Trp Asn Ala Arg Thr Val Glu
            340                 345                 350

Glu Tyr Trp Arg Met Trp Asn Met Pro Val His Lys Trp Ile Val Arg
        355                 360                 365

His Ile Tyr Phe Pro Cys Ile Arg Asn Gly Leu Ser Lys Gly Cys Ala
    370                 375                 380

Ile Leu Ile Ser Phe Leu Val Ser Ala Val Phe His Glu Leu Cys Ile
385                 390                 395                 400

Ala Val Pro Cys His Ile Phe Lys Leu Trp Ala Phe Ser Gly Ile Met
                405                 410                 415

Phe Gln Ile Pro Leu Leu Phe Leu Thr Lys Tyr Leu Gln Asp Lys Phe
            420                 425                 430

Lys Asn Thr Met Ala Gly Asn Met Ile Phe Trp Phe Phe Phe Ser Ile
```

```
        435                 440                 445

Val Gly Gln Pro Met Cys Val Leu Leu Tyr Tyr His Asp Val Met Asn
    450                 455                 460

Arg Gln Ala Gln Thr Asn Gly
465                 470


<210> SEQ ID NO 15
<211> LENGTH: 1434
<212> TYPE: DNA
<213> ORGANISM: Oryza sativa

<400> SEQUENCE: 15

atggccccgc cccctcgct cgcccccgat cgcggcggcg gcgaacccga cgacgccctc      60

cgcctgcggg cccgcgccgc cgccgccgcc ggtgacgctc ccgctccgca gcagcagcag     120

gagcagaggc atcaggagca gcagcagcag ctgctctggt accgcgcgtc ggcgcccgcc     180

caccgccgcg tcagggagag ccccctcagc tccgacgcca tcttccgcca gagccatgca     240

ggccttctga acctatgcat tgttgtgctg gttgctgtga acagcagact tattattgag     300

aatttaatga agtatggcct actaattaga gctggatttt ggtttagtgg aacatcgctg     360

gcagattggc ctcttctcat gtgctgtctc actttaccaa ctttcccgct tgctgcactt     420

atggttgaga agttggctca aagaaaactt attagtaaac atgtggttat tcttctccat     480

atcgttatta caacatctgt ccttgtctat ccagttgttg tgattctaaa gtgtgattcg     540

gcagtattat ctggatttgt gttgatgttt cttgcaagca ttatttggtt gaagcttgtt     600

tcttttgctc atacaaatta tgatataaga atgctgtcca aaagtattga aaagggcgtg     660

acacatgaca tttctataga tccggagaac attaaatggc caacctttaa aaggctatcc     720

tacttcatgt tggccccaac actttgttac cagccaagtt atccccgaac tacatatatt     780

agaaaaggtt gggtggtccg acaactgata aaatgccttg tttttacagg cttgatgggt     840

tttataattg agcaatacat aaatccaatt gtgaagaatt cgaagcatcc attgaaaggg     900

aatttcttga atgctataga gagagtattg aaattatcag tgccaacatt atatgtctgg     960

ctttgcatgt tctactgttt tttccatctc tggttgaata ttcttgctga gctcctctgt    1020

tttggtgatc gtgaattcta caaggactgg tggaatgcca aaacagttga agagtattgg    1080

agaatgtgga atatgcctgt tcacaagtgg gtcattcgac atatatattt tccatgcata    1140

aggaatggtt tttcaaaggg tgttgctatc ctaatctcgt tcctggtttc agctgcattt    1200

catgagctat gtgttgctgt tccatgccac atttttaaat tctgggcatt tattgggatc    1260

atgtttcaga ttcccctggt attcttgacg aaataccttc aagataaatt caataacaca    1320

atggtgggca acatgatatt ttggttcttc ttcagcatcc tggggcaacc aatgtgtgtt    1380

ctcttatact accatgatgt catgaacagg caacaagccc aaacaaatag atag          1434


<210> SEQ ID NO 16
<211> LENGTH: 538
<212> TYPE: PRT
<213> ORGANISM: Oryza sativa

<400> SEQUENCE: 16

Met Val Gly Ser Asp Gly Asp Gly Asp Gly Gly Gly Gly Glu Ala His
1               5                   10                  15

Ala Pro Ala Ala Pro Ala His His His Arg Arg Pro Pro Arg Pro Arg
            20                  25                  30

Gly Gly Ser Gly Ala Ile Val Glu Gly Phe Ala Ala Ala Leu Arg Arg
```

```
        35                  40                  45

Arg Ile Arg Ser Gly Ala Ala Ala Ala Ala Arg Ala Ser Phe Gly Gly
    50                  55                  60

Asp Ser Gly Asp Glu Ala Ala Ser Gly Glu Pro Ser Ser Ser Ser Ser
65                  70                  75                  80

Ser Ser Pro Ser Arg Arg Arg Gly Gly Asp Ser Asn Gly Ala Glu Ala
                85                  90                  95

Ser Ser Ala Ala Gly Gly Gly Gly Gly Arg Gly Gly Gly Gly Asp Phe
            100                 105                 110

Ser Ala Phe Thr Phe Arg Ala Ala Ala Pro Val His Arg Lys Ala Lys
        115                 120                 125

Glu Ser Pro Leu Ser Ser Asp Ala Ile Phe Lys Gln Ser His Ala Gly
    130                 135                 140

Leu Phe Asn Leu Cys Ile Val Val Leu Val Ala Val Asn Ser Arg Leu
145                 150                 155                 160

Ile Ile Glu Asn Leu Met Lys Tyr Gly Leu Leu Ile Arg Ala Gly Phe
                165                 170                 175

Trp Phe Asn Asp Lys Ser Leu Arg Asp Trp Pro Leu Leu Met Cys Cys
            180                 185                 190

Leu Ser Leu Pro Ala Phe Pro Leu Gly Ala Phe Ala Val Glu Lys Leu
        195                 200                 205

Ala Phe Asn Asn Val Ile Thr Asp Ala Val Ala Thr Cys Leu His Ile
    210                 215                 220

Phe Leu Ser Thr Thr Glu Ile Val Tyr Pro Val Leu Val Ile Leu Lys
225                 230                 235                 240

Cys Asp Ser Ala Val Leu Ser Gly Phe Leu Leu Ile Phe Ile Ala Cys
                245                 250                 255

Ile Val Trp Leu Lys Leu Val Ser Phe Ala His Thr Asn His Asp Ile
            260                 265                 270

Arg Gln Leu Thr Met Gly Gly Lys Lys Val Asp Asn Glu Leu Ser Thr
        275                 280                 285

Val Asp Met Asp Asn Leu Gln Pro Pro Thr Leu Gly Asn Leu Ile Tyr
    290                 295                 300

Phe Met Met Ala Pro Thr Leu Cys Tyr Gln Pro Ser Tyr Pro Arg Thr
305                 310                 315                 320

Ser Cys Val Arg Lys Gly Trp Leu Ile Arg Gln Ile Ile Leu Tyr Leu
                325                 330                 335

Ile Phe Thr Gly Leu Gln Gly Phe Ile Ile Glu Gln Tyr Ile Asn Pro
            340                 345                 350

Ile Val Val Asn Ser Gln His Pro Leu Lys Gly Gly Leu Leu Asn Ala
        355                 360                 365

Val Glu Thr Val Leu Lys Leu Ser Leu Pro Asn Val Tyr Leu Trp Leu
    370                 375                 380

Cys Met Phe Tyr Ala Phe Phe His Leu Trp Leu Ser Ile Leu Ala Glu
385                 390                 395                 400

Ile Leu Arg Phe Gly Asp Arg Glu Phe Tyr Lys Asp Trp Trp Asn Ala
                405                 410                 415

Lys Thr Ile Asp Glu Tyr Trp Arg Lys Trp Asn Met Pro Val His Lys
            420                 425                 430

Trp Val Val Arg His Ile Tyr Phe Pro Cys Met Arg Asn Gly Ile Ser
        435                 440                 445

Lys Glu Val Ala Val Leu Ile Ser Phe Leu Val Ser Ala Val Leu His
    450                 455                 460
```

```
Glu Ile Cys Val Ala Val Pro Cys Arg Ile Leu Lys Phe Trp Ala Phe
465                 470                 475                 480

Leu Gly Ile Met Leu Gln Ile Pro Leu Ile Val Leu Thr Ala Tyr Leu
                485                 490                 495

Lys Ser Lys Phe Arg Asp Thr Met Val Gly Asn Met Ile Phe Trp Phe
            500                 505                 510

Phe Phe Cys Ile Tyr Gly Gln Pro Met Cys Leu Leu Leu Tyr Tyr His
        515                 520                 525

Asp Val Met Asn Arg Ile Glu Lys Ala Arg
    530                 535
```

```
<210> SEQ ID NO 17
<211> LENGTH: 1473
<212> TYPE: DNA
<213> ORGANISM: Sorghum bicolor

<400> SEQUENCE: 17

atggccccgc cccctccat ggccgccgcc tccgatcgcg ccgtccccgg cgccgacgcg      60

accgaggcgt cctccctccg cctccgccgc gccccctcag ccgacgccgg cgaccttgcc     120

gacgattcct caggagaccg gcgggagaac ggcgagccgc aaccgccgca ggagcagcag     180

cagcagcacg agatgctgta ctaccgcgcg tcggcgcccg cccaccgccg cgtcaaggag     240

agccccctca gctccgacgc catcttccgg cagagccatg ctggtcttct gaatctatgc     300

atcgttgttc tgattgcagt gaacagcaga ctcattattg agaatttaat gaagtatggc     360

ctattgataa gagctggatt tggtttagt gcaagatcgc tgggtgactg gcccccttcta     420

atgtgctgcc tcactttacc agttttccca cttgttgccc tcatggctga gaagctgatt     480

agaagaaagc tcattggtga acatgtggtt attctactcc atatcattat tacaacatct     540

gtcattgtct atccagttgt tgtgactctt aagtgcgact cagcagtgct atctggattc     600

ttgctaatgt ttcttgcgag catcatgtgg atgaagcttg tctcttatgc acatacaaat     660

tatgatataa gggcattgtc caaaagtact gaaaagggtg ctgcatatgg aaattatgtc     720

gatcctgaga gtatgaaaga tccaaccttt aaaagtctag tgtacttcat gttggcccca     780

acactttgtt accagccaac ttatccccga actacatgta ttaggaaggg ttgggtgacc     840

cgacaactta taaagtgcct ggtttttaca ggcttgatgg gcttcataat tgagcaatat     900

ataaacccaa ttgtgaagaa ttccaaacat ccactgaaag ggaatttctt gaatgctata     960

gaaagagtct taaaactctc agtgccaaca ttatatgtat ggctttgcat gttctattgc    1020

ttttttcatt tatggctgaa cattctagct gaactcctct gtttcggtga ccgtgaattc    1080

tacaaggact ggtggaatgc caaaactgtt gaagagtact ggaggatgtg gaacatgcct    1140

gttcataaat ggatcatcag acacatatat tttccatgta taaggaaagg cttttccagg    1200

ggtgtagcta ttctagtctc gtttctggtt tcagctgtat ttcatgagat atgtattgcg    1260

gtgccgtgcc acattttcaa attctgggca ttttctggga tcatgtttca gataccgttg    1320

gtattcttga caagatatct ccaggctacg ttcaagaata taatggtggg caacatgata    1380

ttttggttct tcttcagtat agtcgggcag ccgatgtgtg tccttttata ctaccatgat    1440

gtcatgaaca ggcaggccca ggcaagtaga taa                                 1473
```

```
<210> SEQ ID NO 18
<211> LENGTH: 515
<212> TYPE: PRT
<213> ORGANISM: Sorghum bicolor
```

<400> SEQUENCE: 18

```
Met Ala Asp Thr Asp Asp Ala Pro Pro Ala Pro Ala Val His Arg Arg
1               5                   10                  15

Pro Pro Arg Pro Ala Arg Gly Ala Ala Ala Ala Gln Gly Phe Ala Ala
            20                  25                  30

Lys Leu Arg Arg Arg Leu Ser Ser Gly Ala Ala Ala Ala Ala Arg Ala
        35                  40                  45

Ser Phe Ala Ala Asp Ser Gly Asp Glu Ser Gly Pro Gly Glu Pro Ser
    50                  55                  60

Ser Ser Arg Arg Arg Asp Asn Gly Gly Asp Ala Ser Ser Ala Ala Asp
65                  70                  75                  80

Gly Gly Arg Gly Gly Ala Gly Asp Phe Ser Ala Phe Thr Phe Arg Ala
                85                  90                  95

Ala Ala Pro Val His Arg Lys Ala Lys Glu Ser Pro Leu Ser Ser Asp
            100                 105                 110

Ala Ile Phe Lys Gln Ser His Ala Gly Leu Phe Asn Leu Cys Ile Val
        115                 120                 125

Val Leu Val Ala Val Asn Ser Arg Leu Ile Ile Glu Asn Leu Met Lys
    130                 135                 140

Tyr Gly Leu Leu Ile Arg Ser Gly Phe Trp Phe Asn Ala Thr Ser Leu
145                 150                 155                 160

Arg Asp Trp Pro Leu Leu Met Cys Cys Leu Ser Leu Pro Val Phe Pro
                165                 170                 175

Leu Gly Ala Phe Ala Val Glu Lys Leu Ala Phe Asn Asn Leu Ile Thr
            180                 185                 190

Asp Ala Ala Ala Thr Cys Phe His Ile Phe Leu Thr Thr Leu Glu Ile
        195                 200                 205

Val Tyr Pro Val Leu Val Ile Leu Lys Cys Asp Ser Ala Val Leu Ser
    210                 215                 220

Gly Phe Val Leu Met Phe Ile Ala Cys Ile Val Trp Leu Lys Leu Val
225                 230                 235                 240

Ser Phe Ala His Thr Asn His Asp Ile Arg Lys Leu Ile Thr Ser Gly
                245                 250                 255

Lys Lys Val Asp Asn Glu Leu Thr Val Ala Asp Ile Asp Asn Leu Gln
            260                 265                 270

Ala Pro Thr Leu Gly Ser Leu Thr Tyr Phe Met Met Ala Pro Thr Leu
        275                 280                 285

Cys Tyr Gln Pro Ser Tyr Pro Arg Thr Pro Tyr Val Arg Lys Gly Trp
    290                 295                 300

Leu Val Arg Gln Val Ile Leu Tyr Leu Ile Phe Thr Gly Leu Gln Gly
305                 310                 315                 320

Phe Ile Ile Glu Gln Tyr Ile Asn Pro Ile Val Val Asn Ser Gln His
                325                 330                 335

Pro Leu Lys Gly Gly Leu Leu Asn Ala Val Glu Thr Val Leu Lys Leu
            340                 345                 350

Ser Leu Pro Asn Val Tyr Leu Trp Leu Cys Met Phe Tyr Cys Leu Phe
        355                 360                 365

His Leu Trp Leu Asn Ile Leu Ala Glu Ile Leu Arg Phe Gly Asp Arg
    370                 375                 380

Glu Phe Tyr Lys Asp Trp Trp Asn Ala Lys Thr Ile Asp Glu Tyr Trp
385                 390                 395                 400

Arg Lys Trp Asn Met Pro Val His Lys Trp Met Leu Arg His Ile Tyr
```

```
            405                 410                 415

Phe Pro Cys Ile Arg Asn Gly Ile Ser Lys Glu Val Ala Ala Phe Ile
            420                 425                 430

Ala Phe Phe Val Ser Ala Val Phe His Glu Leu Cys Val Ala Val Pro
        435                 440                 445

Cys His Ile Leu Lys Phe Trp Ala Phe Leu Gly Ile Met Leu Gln Ile
    450                 455                 460

Pro Leu Ile Ile Leu Thr Ser Tyr Leu Lys Asn Lys Phe Asn Asp Thr
465                 470                 475                 480

Met Val Gly Asn Met Ile Phe Trp Phe Phe Phe Cys Ile Tyr Gly Gln
                485                 490                 495

Pro Met Cys Val Leu Leu Tyr Tyr His Asp Val Met Asn Arg Thr Glu
            500                 505                 510

Lys Thr Lys
        515
```

<210> SEQ ID NO 19
<211> LENGTH: 1536
<212> TYPE: DNA
<213> ORGANISM: Triticum aestivum

<400> SEQUENCE: 19

```
atgtcaaaag ggaacccaga cccgccacct ccccggcagc ttcctccctt cccacggcgg     60

gccgcccacc gaaacccaaa accccgcccc gaaccttccg gaacctcccc tccagttcca    120

cccatggccc cgcccccgtc cgtggccgct gcccacgatc gcgacgaccc ctccctccgc    180

ctccgccgcg cccctgccgc cgacggcgtc cacggagagg cggagccgca ggagcagccg    240

cagcggcagc acgagatgcc ctgctaccgg gcgtcggcgc ccgcccaccg ccgggtcaag    300

gagagcccgc ttagctccga cgccatcttc cgacagagcc atgcaggtct tctgaatcta    360

tgcattgttg tgctgattgc agtgaacagc aggctcatta tcgagaactt aatgaagtat    420

ggcctattaa taagagctgg gttttggttt agtgcaagat cgctgggaga ttggccactt    480

ctgatgtgct gcctcacttt acccattttc ccacttgctg cactcatgac cgagaagtgg    540

gctcaaagaa agctcatccg tgatcatgtg tctattcttc tccatataat tattacaacc    600

actgtcctta tctatccggt tgttgtgatt cttaagtgtg aatcagcagt attatctgga    660

tttgtgttaa tgttcattgc aagcattact tggttgaagc ttgtctcttt tgctcataca    720

aattatgata taagggtgtt gtcccaaagt attgaaaagg gtgctacaca tggcagttct    780

atcgatgagg aaaacattaa aggcccaact atcaacagtg ttgtgtattt catgttggcc    840

ccaacacttt gttaccagcc aagttatccc cggacagcat ttactaggaa aggctgggtc    900

actcggcagc ttataaaatg cgtagttttt acaggcttga tgggcttcat aattgagcaa    960

tacattaatc caattgtgca gaattccaag catccattaa aaggaaattt cttggatgct   1020

attgagagag tcttgaaact gtcagtgcca acattatatg tatggctttg tatgttctat   1080

tcctttttcc atctgtggtt gaatattctt gccgaactcc tccgttttgg tgatcgtgaa   1140

ttctacaagg actggtggaa tgccaaaaca gttgaagagt actggagaat gtggaatatg   1200

cctgttcata agtggatcgt tcgccatata tattttccat gcataaggaa tggcttgtca   1260

aagggttgtg ccattctcat cgcatttctg gtttcagctg tatttcatga gctatgtatt   1320

gctgttccat gccacatttt caaattatgg gcgttttctg gaatcatgtt tcagattccc   1380

ctgctattct tgacgaaata tcttcaagaa aagttcaaga acacaatggt gggcaacatg   1440
```

```
atattttggt tcttcttcag catagttggg cagccaatgt gtgttctctt gtactaccat   1500

gatgtcatga acagacaggc tcagacaaat ggctag                             1536


<210> SEQ ID NO 20
<211> LENGTH: 511
<212> TYPE: PRT
<213> ORGANISM: Triticum aestivum

<400> SEQUENCE: 20

Met Ser Lys Gly Asn Pro Asp Pro Pro Pro Pro Arg Gln Leu Pro Pro
1               5                   10                  15

Phe Pro Arg Arg Ala Ala His Arg Asn Pro Lys Pro Arg Pro Glu Pro
            20                  25                  30

Ser Gly Thr Ser Pro Pro Val Pro Pro Met Ala Pro Pro Pro Ser Val
        35                  40                  45

Ala Ala Ala His Asp Arg Asp Asp Pro Ser Leu Arg Leu Arg Arg Ala
    50                  55                  60

Pro Ala Ala Asp Gly Val His Gly Glu Ala Glu Pro Gln Glu Gln Pro
65                  70                  75                  80

Gln Arg Gln His Glu Met Pro Cys Tyr Arg Ala Ser Ala Pro Ala His
                85                  90                  95

Arg Arg Val Lys Glu Ser Pro Leu Ser Ser Asp Ala Ile Phe Arg Gln
            100                 105                 110

Ser His Ala Gly Leu Leu Asn Leu Cys Ile Val Val Leu Ile Ala Val
        115                 120                 125

Asn Ser Arg Leu Ile Ile Glu Asn Leu Met Lys Tyr Gly Leu Leu Ile
    130                 135                 140

Arg Ala Gly Phe Trp Phe Ser Ala Arg Ser Leu Gly Asp Trp Pro Leu
145                 150                 155                 160

Leu Met Cys Cys Leu Thr Leu Pro Ile Phe Pro Leu Ala Ala Leu Met
                165                 170                 175

Thr Glu Lys Trp Ala Gln Arg Lys Leu Ile Arg Asp His Val Ser Ile
            180                 185                 190

Leu Leu His Ile Ile Ile Thr Thr Thr Val Leu Ile Tyr Pro Val Val
        195                 200                 205

Val Ile Leu Lys Cys Glu Ser Ala Val Leu Ser Gly Phe Val Leu Met
    210                 215                 220

Phe Ile Ala Ser Ile Thr Trp Leu Lys Leu Val Ser Phe Ala His Thr
225                 230                 235                 240

Asn Tyr Asp Ile Arg Val Leu Ser Gln Ser Ile Glu Lys Gly Ala Thr
                245                 250                 255

His Gly Ser Ser Ile Asp Glu Glu Asn Ile Lys Gly Pro Thr Ile Asn
            260                 265                 270

Ser Val Val Tyr Phe Met Leu Ala Pro Thr Leu Cys Tyr Gln Pro Ser
        275                 280                 285

Tyr Pro Arg Thr Ala Phe Thr Arg Lys Gly Trp Val Thr Arg Gln Leu
    290                 295                 300

Ile Lys Cys Val Val Phe Thr Gly Leu Met Gly Phe Ile Ile Glu Gln
305                 310                 315                 320

Tyr Ile Asn Pro Ile Val Gln Asn Ser Lys His Pro Leu Lys Gly Asn
                325                 330                 335

Phe Leu Asp Ala Ile Glu Arg Val Leu Lys Leu Ser Val Pro Thr Leu
            340                 345                 350

Tyr Val Trp Leu Cys Met Phe Tyr Ser Phe Phe His Leu Trp Leu Asn
```

```
        355                 360                 365

Ile Leu Ala Glu Leu Leu Arg Phe Gly Asp Arg Glu Phe Tyr Lys Asp
    370                 375                 380

Trp Trp Asn Ala Lys Thr Val Glu Glu Tyr Trp Arg Met Trp Asn Met
385                 390                 395                 400

Pro Val His Lys Trp Ile Val Arg His Ile Tyr Phe Pro Cys Ile Arg
                405                 410                 415

Asn Gly Leu Ser Lys Gly Cys Ala Ile Leu Ile Ala Phe Leu Val Ser
            420                 425                 430

Ala Val Phe His Glu Leu Cys Ile Ala Val Pro Cys His Ile Phe Lys
        435                 440                 445

Leu Trp Ala Phe Ser Gly Ile Met Phe Gln Ile Pro Leu Leu Phe Leu
    450                 455                 460

Thr Lys Tyr Leu Gln Glu Lys Phe Lys Asn Thr Met Val Gly Asn Met
465                 470                 475                 480

Ile Phe Trp Phe Phe Phe Ser Ile Val Gly Gln Pro Met Cys Val Leu
                485                 490                 495

Leu Tyr Tyr His Asp Val Met Asn Arg Gln Ala Gln Thr Asn Gly
            500                 505                 510


<210> SEQ ID NO 21
<211> LENGTH: 1485
<212> TYPE: DNA
<213> ORGANISM: Zea mays

<400> SEQUENCE: 21

atggccccgc ccccctccat gcctgccgcc tccgatcgcg ccggccctgg ccgcgacgcg     60

ggcgactcgt cctcccttcg cctccgccgc gccccctcag ccgacgccgg cgaccttgcc    120

ggcgattcct cgggaggctt gcgggagaac ggcgagccgc aatcgccgac gaatccgccg    180

ccgcaggagc agcagcagca cgagatgcta tactaccgcg cgtcggcgcc cgcccaccgc    240

cgcgtcaagg agagccccct cagctctgac gccatcttcc ggcagagcca tgctggtctt    300

ctgaatctat gcattgttgt tctgatcgca gtgaacagca gactcattat tgagaattta    360

atgaagtatg gcctgttgat aagagctgga ttttggttta gtgcaagatc gctgggtgac    420

tggcccettc taatgtgctg cctcactcta ccagttttcc cactagttgc actcatggct    480

gagaagctga tcacaagaaa gctcattggt gaacatgtgg ttattctact ccatatcatt    540

attacaacat ctgccattgt ctatccagtt gttgtgactc ttaagtgtga ctcagcagta    600

ctatctggat ttgtgctaat gtttcttgcg agcatcatgt ggatgaagct tgtctcttat    660

gcacatacaa attatgatat aagggtattg tccaaaagta ctgaaaaggg tgctgcatat    720

ggaaattatg tcgatcctga gaatatgaaa gatccaacct ttaaaagtct agtgtacttt    780

atgttggccc caacactttg ttaccagcca acttatcctc aaactacatg tattagaaag    840

ggttgggtga cccagcaact cataaagtgc gtggttttta caggcttgat gggcttcata    900

attgagcaat atataaaccc aattgtgaag aattccaaac atccactgaa agggaatttt    960

ttgaatgcta tagaaagagt cttaaaactc tcagtgccaa cattatatgt atggctttgc   1020

atgttctatt gctttttttca tttatggctg aacattgtag ctgaactcct ctgtttcggt   1080

gaccgtgaat tctataagga ctggtggaat gccaaaactg ttgaagagta ctggaggatg   1140

tggaacatgc ctgttcataa gtggatcatc agacacatat attttccatg tataaggaaa   1200

ggcttttcca ggggtgtagc tattctaatc tcgtttctgg tttcagctgt atttcatgag   1260
```

```
atatgtattg cggtgccttg ccacattttc aaattctggg cattttctgg gatcatgttt   1320

cagataccct tggtattctt gacaagatat ctccatgcta cgttcaagca tgtaatggtg   1380

ggcaacatga tattttggtt cttcttcagt atagtcggac agccgatgtg tgtccttcta   1440

tactaccatg acgtcatgaa caggcaggcc caggcaagta gatag                   1485
```

```
<210> SEQ ID NO 22
<211> LENGTH: 494
<212> TYPE: PRT
<213> ORGANISM: Zea mays

<400> SEQUENCE: 22

Met Ala Pro Pro Pro Ser Met Pro Ala Ala Ser Asp Arg Ala Gly Pro
1               5                   10                  15

Gly Arg Asp Ala Gly Asp Ser Ser Ser Leu Arg Leu Arg Arg Ala Pro
            20                  25                  30

Ser Ala Asp Ala Gly Asp Leu Ala Gly Asp Ser Ser Gly Gly Leu Arg
        35                  40                  45

Glu Asn Gly Glu Pro Gln Ser Pro Thr Asn Pro Pro Pro Gln Glu Gln
    50                  55                  60

Gln Gln His Glu Met Leu Tyr Tyr Arg Ala Ser Ala Pro Ala His Arg
65                  70                  75                  80

Arg Val Lys Glu Ser Pro Leu Ser Ser Asp Ala Ile Phe Arg Gln Ser
                85                  90                  95

His Ala Gly Leu Leu Asn Leu Cys Ile Val Val Leu Ile Ala Val Asn
            100                 105                 110

Ser Arg Leu Ile Ile Glu Asn Leu Met Lys Tyr Gly Leu Leu Ile Arg
        115                 120                 125

Ala Gly Phe Trp Phe Ser Ala Arg Ser Leu Gly Asp Trp Pro Leu Leu
    130                 135                 140

Met Cys Cys Leu Thr Leu Pro Val Phe Pro Leu Val Ala Leu Met Ala
145                 150                 155                 160

Glu Lys Leu Ile Thr Arg Lys Leu Ile Gly Glu His Val Val Ile Leu
                165                 170                 175

Leu His Ile Ile Ile Thr Thr Ser Ala Ile Val Tyr Pro Val Val Val
            180                 185                 190

Thr Leu Lys Cys Asp Ser Ala Val Leu Ser Gly Phe Val Leu Met Phe
        195                 200                 205

Leu Ala Ser Ile Met Trp Met Lys Leu Val Ser Tyr Ala His Thr Asn
    210                 215                 220

Tyr Asp Ile Arg Val Leu Ser Lys Ser Thr Glu Lys Gly Ala Ala Tyr
225                 230                 235                 240

Gly Asn Tyr Val Asp Pro Glu Asn Met Lys Asp Pro Thr Phe Lys Ser
                245                 250                 255

Leu Val Tyr Phe Met Leu Ala Pro Thr Leu Cys Tyr Gln Pro Thr Tyr
            260                 265                 270

Pro Gln Thr Thr Cys Ile Arg Lys Gly Trp Val Thr Gln Gln Leu Ile
        275                 280                 285

Lys Cys Val Val Phe Thr Gly Leu Met Gly Phe Ile Ile Glu Gln Tyr
    290                 295                 300

Ile Asn Pro Ile Val Lys Asn Ser Lys His Pro Leu Lys Gly Asn Phe
305                 310                 315                 320

Leu Asn Ala Ile Glu Arg Val Leu Lys Leu Ser Val Pro Thr Leu Tyr
                325                 330                 335
```

-continued

```
Val Trp Leu Cys Met Phe Tyr Cys Phe Phe His Leu Trp Leu Asn Ile
            340                 345                 350

Val Ala Glu Leu Leu Cys Phe Gly Asp Arg Glu Phe Tyr Lys Asp Trp
        355                 360                 365

Trp Asn Ala Lys Thr Val Glu Glu Tyr Trp Arg Met Trp Asn Met Pro
    370                 375                 380

Val His Lys Trp Ile Ile Arg His Ile Tyr Phe Pro Cys Ile Arg Lys
385                 390                 395                 400

Gly Phe Ser Arg Gly Val Ala Ile Leu Ile Ser Phe Leu Val Ser Ala
                405                 410                 415

Val Phe His Glu Ile Cys Ile Ala Val Pro Cys His Ile Phe Lys Phe
            420                 425                 430

Trp Ala Phe Ser Gly Ile Met Phe Gln Ile Pro Leu Val Phe Leu Thr
        435                 440                 445

Arg Tyr Leu His Ala Thr Phe Lys His Val Met Val Gly Asn Met Ile
    450                 455                 460

Phe Trp Phe Phe Phe Ser Ile Val Gly Gln Pro Met Cys Val Leu Leu
465                 470                 475                 480

Tyr Tyr His Asp Val Met Asn Arg Gln Ala Gln Ala Ser Arg
                485                 490


<210> SEQ ID NO 23
<211> LENGTH: 1539
<212> TYPE: DNA
<213> ORGANISM: Elaeis guineensis

<400> SEQUENCE: 23

atggcggtct cgaagaatcc agaaacccta gcccccgatc aagaaccgtc gaaggagtcg      60

gatctccgcc ggaggccggc ttcctccccc tcctccaccg ccgcttcgcc ggcggttccg     120

gactcgtctt caagaacgag ctcttccatc accgggagct ggaccacggc gttagatgga     180

gattctggtg caggagctgt ccgcattggt gatccaaagg atcggatagg cgaggcgaac     240

gatattggtg aaaagaagaa ggcctgttcg ggtgaagttc cggtggggtt cgtggaccgg     300

ccttcagctc cggtgcatgt gagagtggtg gagagcccgc tgagctcgga tacgatcttt     360

caacagagcc atgcaggtct cttgaacctt tgtgtagtag ttctgattgc agttaacagc     420

aggcttatta ttgagaactt gatgaagtat ggtttactaa taggaagtgg atttttcttc     480

agttcaagat tactgaggga ttggccacta cttatatgta gtctcactct acctgttttc     540

cctcttggat cttacatggt tgaaaagctg gcatataaga agttcatttc tgaacctgtt     600

gttgtctcac ttcatgtaat actcataata gctaccatca tgtatccagt tttcgtgatt     660

ctaaggtgcg attctcctat tttatctggc atcaatctaa tgctctttgt gagctctatt     720

tgcctaaagc ttgtttcata tgcacatgca aattacgatt taaggtcatc atccaactct     780

attgataagg ggatacacaa gtctcaaggt gttagcttca aaagtttggt gtattttata     840

atggctccca cgctatgtta ccagccaagt tatcctcgga ctacgtgcat cagaaagggt     900

tgggtgattt gtcagcttgt taagttggtg atatttactg ggtgatggg cttcatcatt      960

gagcagtaca ttgacccgat tatcaagaat tctcaacatc ctctaaaagg aaatgtctta    1020

aatgctatgg agagagtctt gaagctatca ataccaactt tgtacgtgtg gctttgtgta    1080

ttctattgca ccttccattt gtggttaaac attcttgctg agctcctttg ttttggtgat    1140

cgtgaattct ataaagattg gtggaatgca aaaacaattg aagagtattg gagaatgtgg    1200

aacatgcctg ttcataaatg gatgcttcgc catgtttatc ttccatgcat acggaatggt    1260
```

```
ataccaaagg gagttgcgat ggtcatctca tttttcattt ctgctatatt ccatgagcta   1320

tgcattggta tcccctgcca tatattcaag ttctgggctt tcatagggat aatgtttcag   1380

gttccacttg tcatcttgac aaagtacctc cagaataaat ttaaaagtgc catggtggga   1440

aacatgatct tctggttctt cttcagcata tatggacagc ctatgtgtgt tctgctttac   1500

taccatgatg tgatgaacag aaaagtggga acagagtaa                          1539


<210> SEQ ID NO 24
<211> LENGTH: 512
<212> TYPE: PRT
<213> ORGANISM: Elaeis guineensis

<400> SEQUENCE: 24

Met Ala Val Ser Lys Asn Pro Glu Thr Leu Ala Pro Asp Gln Glu Pro
1               5                   10                  15

Ser Lys Glu Ser Asp Leu Arg Arg Arg Pro Ala Ser Ser Pro Ser Ser
            20                  25                  30

Thr Ala Ala Ser Pro Ala Val Pro Asp Ser Ser Ser Arg Thr Ser Ser
        35                  40                  45

Ser Ile Thr Gly Ser Trp Thr Thr Ala Leu Asp Gly Asp Ser Gly Ala
    50                  55                  60

Gly Ala Val Arg Ile Gly Asp Pro Lys Asp Arg Ile Gly Glu Ala Asn
65                  70                  75                  80

Asp Ile Gly Glu Lys Lys Lys Ala Cys Ser Gly Glu Val Pro Val Gly
                85                  90                  95

Phe Val Asp Arg Pro Ser Ala Pro Val His Val Arg Val Val Glu Ser
            100                 105                 110

Pro Leu Ser Ser Asp Thr Ile Phe Gln Gln Ser His Ala Gly Leu Leu
        115                 120                 125

Asn Leu Cys Val Val Val Leu Ile Ala Val Asn Ser Arg Leu Ile Ile
    130                 135                 140

Glu Asn Leu Met Lys Tyr Gly Leu Leu Ile Gly Ser Gly Phe Phe Phe
145                 150                 155                 160

Ser Ser Arg Leu Leu Arg Asp Trp Pro Leu Leu Ile Cys Ser Leu Thr
                165                 170                 175

Leu Pro Val Phe Pro Leu Gly Ser Tyr Met Val Glu Lys Leu Ala Tyr
            180                 185                 190

Lys Lys Phe Ile Ser Glu Pro Val Val Val Ser Leu His Val Ile Leu
        195                 200                 205

Ile Ile Ala Thr Ile Met Tyr Pro Val Phe Val Ile Leu Arg Cys Asp
    210                 215                 220

Ser Pro Ile Leu Ser Gly Ile Asn Leu Met Leu Phe Val Ser Ser Ile
225                 230                 235                 240

Cys Leu Lys Leu Val Ser Tyr Ala His Ala Asn Tyr Asp Leu Arg Ser
                245                 250                 255

Ser Ser Asn Ser Ile Asp Lys Gly Ile His Lys Ser Gln Gly Val Ser
            260                 265                 270

Phe Lys Ser Leu Val Tyr Phe Ile Met Ala Pro Thr Leu Cys Tyr Gln
        275                 280                 285

Pro Ser Tyr Pro Arg Thr Thr Cys Ile Arg Lys Gly Trp Val Ile Cys
    290                 295                 300

Gln Leu Val Lys Leu Val Ile Phe Thr Gly Val Met Gly Phe Ile Ile
305                 310                 315                 320
```

```
Glu Gln Tyr Ile Asp Pro Ile Ile Lys Asn Ser Gln His Pro Leu Lys
                325                 330                 335

Gly Asn Val Leu Asn Ala Met Glu Arg Val Leu Lys Leu Ser Ile Pro
            340                 345                 350

Thr Leu Tyr Val Trp Leu Cys Val Phe Tyr Cys Thr Phe His Leu Trp
        355                 360                 365

Leu Asn Ile Leu Ala Glu Leu Leu Cys Phe Gly Asp Arg Glu Phe Tyr
    370                 375                 380

Lys Asp Trp Trp Asn Ala Lys Thr Ile Glu Glu Tyr Trp Arg Met Trp
385                 390                 395                 400

Asn Met Pro Val His Lys Trp Met Leu Arg His Val Tyr Leu Pro Cys
                405                 410                 415

Ile Arg Asn Gly Ile Pro Lys Gly Val Ala Met Val Ile Ser Phe Phe
            420                 425                 430

Ile Ser Ala Ile Phe His Glu Leu Cys Ile Gly Ile Pro Cys His Ile
        435                 440                 445

Phe Lys Phe Trp Ala Phe Ile Gly Ile Met Phe Gln Val Pro Leu Val
    450                 455                 460

Ile Leu Thr Lys Tyr Leu Gln Asn Lys Phe Lys Ser Ala Met Val Gly
465                 470                 475                 480

Asn Met Ile Phe Trp Phe Phe Phe Ser Ile Tyr Gly Gln Pro Met Cys
                485                 490                 495

Val Leu Leu Tyr Tyr His Asp Val Met Asn Arg Lys Val Gly Thr Glu
            500                 505                 510


<210> SEQ ID NO 25
<211> LENGTH: 1449
<212> TYPE: DNA
<213> ORGANISM: Artificial Sequence
<220> FEATURE:
<223> OTHER INFORMATION: soybean DGAT1A with 48 bp deletion

<400> SEQUENCE: 25

atggcgattt ccgatgagcc tgaaactgta gccactgctc tcaaccactc ttccctgcgc     60

cgccgtccca ccgccgactt ggccaaggat tccggttccg acgactccat cagcagcgac    120

gccgccaatt cgcaaccgca acaaaaacaa gacactgatt tctccgtcct caaattcgcc    180

taccgtcctt ccgtccccgc tcatcgcaaa gtgaaggaaa gtccgctcag ctccgacacc    240

attttccgtc agagtcacgc gggcctcttc aacctctgta tagtagtcct tgttgctgtg    300

aatagccgac tcatcattga gaatttaatg aagtatggtt ggttgatcaa atctggcttt    360

tggtttagct caaagtcatt gagagactgg cccctcttca tgtgttgtct ttctcttgtg    420

gtatttcctt ttgctgcatt tatagtggag aagttggcac agcagaagtg tatacccgaa    480

ccagttgttg ttgtacttca tataatcatt acctcagctt cacttttcta tccagtttta    540

gtaattctca ggtgtgattc tgcttttcta tcaggtgtta cgttaatgct atttgcttgt    600

gttgtatggt taaaattggt gtcttatgca catacaaact atgatatgag agcacttacc    660

aaatcagttg aaaagggaga agctctgccc gatactctga acatggacta tccttacaat    720

gtaagcttca agagcttagc atatttcctg gttgccccta cattatgtta ccagccaagc    780

tatcctcgca caccttatat tcgaaagggt tggctgtttc gccaacttgt caagctgata    840

atatttacag gagttatggg atttataata gaacaataca ttaatcccat tgtacaaaat    900

tcacagcatc ctctcaaggg aaaccttctt tacgccatcg agagagttct gaagctttct    960

gttccaaatt tatatgtgtg gctctgcatg ttctattgct tttccacctt ttggttaaat   1020
```

```
atattggcag agcttcttcg atttggtgat cgtgaattct accaggattg gtggaatgcc   1080

aaaactgttg aagattattg gaggatgtgg aatatgcctg ttcacaaatg gatgatccgc   1140

cacctatatt ttccatgttt aaggcacggt ataccaaagg ccgttgctct tttaattgcc   1200

ttcctggttt ctgctttatt ccatgagctg tgcatcgctg ttccttgcca catattcaag   1260

ttgtgggctt tcggtggaat tatgtttcag gttcctttgg tcttcatcac taattatctg   1320

caaaataaat tcagaaactc gatggttgga aatatgattt tttggttcat attcagtatt   1380

cttggtcaac ctatgtgcgt actgctatat taccatgact taatgaatag gaaaggcaaa   1440

cttgactga                                                           1449
```

<210> SEQ ID NO 26
<211> LENGTH: 1455
<212> TYPE: DNA
<213> ORGANISM: Artificial Sequence
<220> FEATURE:
<223> OTHER INFORMATION: soybean DGAT1B with 60 bp deletion

<400> SEQUENCE: 26

```
atggcgattt ccgatgagcc tgaaagtgta gccactgctc tcaaccactc ttccctgcgc     60

cgccgtccct ccgacttggc caaggattct ggttccgacg actccatcaa cagcgacgac    120

gccgccgtca attcccaaca gcaaaacgaa aaacaagaca ctgatttctc cgtcctcaaa    180

ttcgcctacc gtccttccgt ccccgctcac cgcaaagtga aggaaagtcc gctcagctcc    240

gacactattt tccgtcagag tcacgcgggc ctcttcaacc tttgtatagt agtccttgtt    300

gctgtgaata gccgactcat cattgagaat ttaatgaagt atggttggtt gatcaaatct    360

ggcttttggt ttagttcaaa gtcattgaga gactggcccc ttttcatgtg ttgtctttct    420

cttgtggtat ttcctttcgc tgcctttata gtggagaagt tggcacaacg gaagtgtata    480

cccgaaccag ttgttgttgt acttcatata atcattacct caacttcgct tttctatcca    540

gttttagtta ttctcaggtg tgattctgct tttgtatcag gtgtcacgtt aatgctgttt    600

tcttgtgttg tatggttaaa attggtgtct tatgcacata caaactatga tatgagagca    660

cttaccaaat tagttgaaaa gggagaagca ctgctcgata ctctgaacat ggactatcct    720

tacaacgtaa gcttcaagag cttggcatat ttcctggttg cccctacatt atgttaccag    780

ccaagctatc ctcgcacacc ttatattcga aagggttggt tgtttcgcca acttgtcaag    840

ctgataatat ttacaggagt tatgggattt ataatagaac aatatattaa tcccatagta    900

caaaattcac agcatcctct caagggaaac cttctttacg ccaccgagag agttctgaag    960

ctttctgttc caaatttata tgtgtggctc tgcatgttct attgcttttt ccacctttgg   1020

ttaaatatcc tggcagagct tcttcgattt ggtgatcgtg aattctacaa ggattggtgg   1080

aatgccaaaa ctgtcgaaga ttattggagg atgtggaata tgcctgttca caaatggatg   1140

atccgccacc tatattttcc atgtttaagg cacggtctac caaaggctgc tgctctttta   1200

attgccttcc tggtttctgc tttattccat gagctgtgca ttgctgttcc ttgccacata   1260

ttcaagttgt gggctttcgg tggaattatg tttcaggttc ctttggtctt gatcactaat   1320

tatctgcaaa ataaattcag aaactcaatg gttggaaata tgattttttg gttcatattc   1380

agtatccttg gtcaacctat gtgtgtactg ctatactacc atgacttgat gaataggaaa   1440

ggcaaacttg actga                                                    1455
```

<210> SEQ ID NO 27

```
<211> LENGTH: 504
<212> TYPE: PRT
<213> ORGANISM: Artificial Sequence
<220> FEATURE:
<223> OTHER INFORMATION: soybean DGAT1b with 60bp deletion

<400> SEQUENCE: 27

Met Ala Ile Ser Asp Glu Pro Glu Ser Val Ala Thr Ala Leu Asn His
1               5                   10                  15

Ser Ser Leu Arg Arg Arg Pro Ser Ala Thr Ser Thr Ala Gly Leu Phe
            20                  25                  30

Asn Ser Pro Glu Thr Thr Thr Asp Ser Ser Gly Asp Asp Leu Ala Lys
        35                  40                  45

Asp Ser Gly Ser Asp Asp Ser Ile Asn Asn Asp Asp Ala Ala Val Asn
    50                  55                  60

Ser Gln Gln Gln Asn Glu Lys Gln Asp Thr Asp Phe Ser Val Leu Lys
65                  70                  75                  80

Phe Ala Tyr Arg Pro Ser Val Pro Ala His Arg Lys Val Lys Glu Ser
                85                  90                  95

Pro Leu Ser Ser Asp Thr Ile Phe Arg Gln Ser His Ala Gly Leu Phe
            100                 105                 110

Asn Leu Cys Ile Val Val Leu Val Ala Val Asn Ser Arg Leu Ile Ile
        115                 120                 125

Glu Asn Leu Met Lys Tyr Gly Trp Leu Ile Lys Ser Gly Phe Trp Phe
    130                 135                 140

Ser Ala Lys Ser Leu Arg Asp Trp Pro Leu Phe Met Cys Cys Leu Ser
145                 150                 155                 160

Leu Val Val Phe Pro Phe Ala Ala Phe Met Val Glu Lys Leu Ala Gln
                165                 170                 175

Arg Lys Cys Ile Pro Glu Pro Val Val Val Val Leu His Ile Ile Ile
            180                 185                 190

Thr Ser Thr Ser Leu Phe Tyr Pro Val Leu Val Ile Leu Lys Cys Asp
        195                 200                 205

Ser Ala Phe Val Ser Gly Val Thr Leu Met Leu Phe Ser Cys Val Val
    210                 215                 220

Trp Leu Lys Leu Val Ser Phe Ala His Thr Asn Tyr Asp Met Arg Ala
225                 230                 235                 240

Leu Thr Lys Leu Val Glu Lys Gly Glu Ala Leu Leu Asp Thr Leu Asn
                245                 250                 255

Met Glu Tyr Pro Tyr Asn Val Thr Phe Lys Ser Leu Ala Tyr Phe Leu
            260                 265                 270

Leu Ala Pro Thr Leu Cys Tyr Gln Pro Ser Tyr Pro Arg Thr Pro Tyr
        275                 280                 285

Ile Arg Lys Gly Trp Leu Phe Arg Gln Leu Val Lys Leu Ile Val Phe
    290                 295                 300

Thr Gly Val Met Gly Phe Ile Ile Glu Gln Tyr Ile Asn Pro Ile Val
305                 310                 315                 320

Gln Asn Ser Gln His Pro Leu Lys Gly Asn Leu Leu Tyr Ala Thr Glu
                325                 330                 335

Arg Val Leu Lys Leu Ser Val Pro Asn Leu Tyr Val Trp Leu Cys Met
            340                 345                 350

Phe Tyr Cys Phe Phe His Leu Trp Leu Asn Ile Val Ala Glu Leu Leu
        355                 360                 365

Arg Phe Gly Asp Arg Glu Phe Tyr Lys Asp Trp Trp Asn Ala Lys Thr
    370                 375                 380
```

```
Val Glu Asp Tyr Trp Arg Met Trp Asn Met Pro Val His Lys Trp Met
385                 390                 395                 400

Ile Arg His Leu Tyr Phe Pro Cys Leu Arg His Gly Leu Pro Lys Ala
                405                 410                 415

Ala Ala Leu Leu Ile Ser Phe Leu Val Ser Ala Leu Phe His Glu Leu
            420                 425                 430

Cys Ile Ala Val Pro Cys His Met Phe Lys Leu Trp Ala Phe Gly Gly
        435                 440                 445

Ile Met Phe Gln Val Pro Leu Val Leu Ile Thr Asn Tyr Leu Gln Asn
    450                 455                 460

Lys Phe Lys Asn Ser Met Val Gly Asn Met Ile Phe Trp Phe Ile Phe
465                 470                 475                 480

Ser Ile Val Gly Gln Pro Met Cys Val Leu Leu Tyr Tyr His Asp Leu
                485                 490                 495

Met Asn Arg Lys Gly Lys Leu Asp
            500


<210> SEQ ID NO 28
<211> LENGTH: 498
<212> TYPE: PRT
<213> ORGANISM: Artificial Sequence
<220> FEATURE:
<223> OTHER INFORMATION: soybean DGAT1A with 48 bp deletion

<400> SEQUENCE: 28

Met Ala Ile Ser Asp Glu Pro Glu Thr Val Ala Thr Ala Leu Asn His
1               5                   10                  15

Ser Ser Leu Arg Arg Arg Pro Thr Ala Ala Gly Leu Phe Asn Ser Pro
            20                  25                  30

Glu Thr Thr Thr Asp Ser Ser Gly Asp Asp Leu Ala Lys Asp Ser Gly
        35                  40                  45

Ser Asp Asp Ser Ile Ser Asn Asp Ala Ala Asn Ser Gln Pro Gln Gln
    50                  55                  60

Lys Gln Asp Thr Asp Phe Ser Val Leu Lys Phe Ala Tyr Arg Pro Ser
65                  70                  75                  80

Val Pro Ala His Arg Lys Val Lys Glu Ser Pro Leu Ser Ser Asp Thr
                85                  90                  95

Ile Phe Arg Gln Ser His Ala Gly Leu Phe Asn Leu Cys Ile Val Val
            100                 105                 110

Leu Val Ala Val Asn Ser Arg Leu Ile Ile Glu Asn Leu Met Lys Tyr
        115                 120                 125

Gly Trp Leu Ile Lys Ser Gly Phe Trp Phe Ser Ala Lys Ser Leu Arg
    130                 135                 140

Asp Trp Pro Leu Phe Met Cys Cys Leu Ser Leu Val Val Phe Pro Phe
145                 150                 155                 160

Ala Ala Phe Met Val Glu Lys Leu Ala Gln Gln Lys Cys Ile Pro Glu
                165                 170                 175

Pro Val Val Val Val Leu His Ile Ile Ile Thr Ser Ala Ser Leu Phe
            180                 185                 190

Tyr Pro Val Leu Val Ile Leu Lys Cys Asp Ser Ala Phe Leu Ser Gly
        195                 200                 205

Val Thr Leu Met Leu Phe Ala Cys Val Val Trp Leu Lys Leu Val Ser
    210                 215                 220

Phe Ala His Thr Asn Tyr Asp Met Arg Ala Leu Thr Lys Ser Val Glu
225                 230                 235                 240
```

```
Lys Gly Glu Ala Leu Pro Asp Thr Leu Asn Met Glu Tyr Pro Tyr Asn
                245                 250                 255

Val Thr Phe Lys Ser Leu Ala Tyr Phe Leu Leu Ala Pro Thr Leu Cys
            260                 265                 270

Tyr Gln Pro Ser Tyr Pro Arg Thr Pro Tyr Ile Arg Lys Gly Trp Leu
        275                 280                 285

Phe Arg Gln Leu Val Lys Leu Ile Val Phe Thr Gly Val Met Gly Phe
    290                 295                 300

Ile Ile Glu Gln Tyr Ile Asn Pro Ile Val Gln Asn Ser Gln His Pro
305                 310                 315                 320

Leu Lys Gly Asn Leu Leu Tyr Ala Ile Glu Arg Val Leu Lys Leu Ser
                325                 330                 335

Val Pro Asn Leu Tyr Val Trp Leu Cys Met Phe Tyr Cys Phe Phe His
            340                 345                 350

Leu Trp Leu Asn Ile Val Ala Glu Leu Leu Arg Phe Gly Asp Arg Glu
        355                 360                 365

Phe Tyr Gln Asp Trp Trp Asn Ala Lys Thr Val Glu Asp Tyr Trp Arg
    370                 375                 380

Met Trp Asn Met Pro Val His Lys Trp Met Ile Arg His Leu Tyr Phe
385                 390                 395                 400

Pro Cys Leu Arg His Gly Ile Pro Lys Ala Val Ala Leu Leu Ile Ser
                405                 410                 415

Phe Leu Val Ser Ala Leu Phe His Glu Leu Cys Ile Ala Val Pro Cys
            420                 425                 430

His Met Phe Lys Leu Trp Ala Phe Gly Gly Ile Met Phe Gln Val Pro
        435                 440                 445

Leu Val Phe Ile Thr Asn Tyr Leu Gln Asn Lys Phe Lys Asn Ser Met
    450                 455                 460

Val Gly Asn Met Ile Phe Trp Phe Ile Phe Ser Ile Val Gly Gln Pro
465                 470                 475                 480

Met Cys Val Leu Leu Tyr Tyr His Asp Leu Met Asn Arg Lys Gly Lys
                485                 490                 495

Leu Asp
```

<210> SEQ ID NO 29
<211> LENGTH: 8217
<212> TYPE: DNA
<213> ORGANISM: Glycine max

<400> SEQUENCE: 29

```
ggagaagaga agactgagtt agaaaacacg ctcggtcttc ttctccaatg gcgatttccg      60

atgagcctga aagtgtagcc actgctctca accactcttc cctgcgccgc cgtccctccg     120

ccacctccac cgccggcctc ttcaattcgc ctgagacaac caccgacagt tccggtgatg     180

acttggccaa ggattctggt tccgacgact ccatcaacag cgacgacgcc gccgtcaatt     240

cccaacagca aaacgaaaaa caagacactg atttctccgt cctcaaattc gcctaccgtc     300

cttccgtccc cgctcaccgc aaagtgaagg aaagtccgct cagctccgac actattttcc     360

gtcaggttct cgccgttaac ttctacttta cgattactac aactctttaa ctatttcaaa     420

ctcaaccaga acggtgccgt tttgttcccg ttctgcataa taaacttctc aatctcaatg     480

caagcgaatc gtagtctttg aggtgcttaa aatagtgtat gctactgcta gttagttctt     540

gtttatttaa tttatgtgta ctagaaacta gttatcaatt tatgatttga atttaataca     600
```

```
attgaattgg tggatcaggt ttttgtagca attatcgtgg tttggtttat aaataggtgt    660

gatgagtctg atatgtaatt atatttcttt actaattatt gaatcggttg cagagtcacg    720

cgggcctctt caacctttgt atagtagtcc ttgttgctgt gaatagccga ctcatcattg    780

agaatttaat gaaggttttg cttcttccat gtttaaattg tacattcacc tgcaacaatt    840

tttctgttct tttatttatg gtcttgattt tgacggttca ggttttattg tctgctttaa    900

tgagtgtttt atttgttctg cagtatggtt ggttgatcaa atctggcttt tggtttagtt    960

caaagtcatt gagagactgg ccccttttca tgtgttggta atgagtgatg aattcccttg   1020

tggattaact gtgtactgtg taattgtttt gacggttgct tcttgaaatg ttgtttaaca   1080

gtatgtggtt gtgcgcttgg tttgcagtct ttctcttgtg gtatttcctt tcgctgcctt   1140

tatagtggag aagttggcac aacggaagtg tatacccgaa ccagtaagtg accaggccat   1200

gtgagctttt attagatttc attcgttgta taatctaaaa tagttttggg atatggttag   1260

ttgtatgtgc tattattaac tgtttaatct ttaatatttg catacattgg aatattatat   1320

tacttgaata ttgcaggttg ttgttgtact tcatataatc attacctcaa cttcgctttt   1380

ctatccagtt ttagttattc tcaggtcagt ttagttcttt gtatacattc ttcaaaattt   1440

attctagggc tgcagttgat gaccttttcg ttttgacatg tgcggttaca ccatgtgtcc   1500

attttgaaag aatttgctta tagaatatgg ttttaagttg ataatggtgt tatataacaa   1560

actttgtcac tatactgcac aggaatttta aaaactttta tcatttatta aaattatttg   1620

agaaaaaatt taaagccgtt gggtgaacct tagtttaatg tttggttctt atgattttgc   1680

aattgaattg ttgcaaaata ttattgcatt gctatatgaa cattgagcaa tgaagttgaa   1740

tgctgcggga taaagtaatt atacagttgt gcgttcttag tcatttcata gataaggata   1800

tcccagaaag atgattacta acttgtagca ttcctttgca ggtgtgattc tgcttttgta   1860

tcaggtgtca cgttaatgct gttttcttgt gttgtatggt taaaattggt gtcttatgca   1920

catacaaact atgatatgag agcacttacc aaattagttg aaaaggtaat aaatactctc   1980

tgtttaaatg gagagaaaat gagggggaga gaaaatttg aattttttt cttgaagtca   2040

acttttccct cttctcttta actaaacaaa agaaaatgta tgattatgtg ttttttcttt   2100

catctaattt tttccttaac caaacatatt cttaagttcc acttgacact tgtaagtggc   2160

tagataaata tcacaaaatg tcatcttcac ttatttgtat actttaaaga tgacagtttg   2220

ttgtacaatg attagttttt gaaccagaac atcctgcttg acttagcagt agcttatgga   2280

tcatgtacta ttaaaacttc ataatatgct aaagtacagt tttatttcat ctaaattcga   2340

attacttcca tcctatgttc ccctttattg cttccttata tctagatgat tagctcttca   2400

catgtgtgaa tgtgccatag ataaaccatc tgttttccct ccttattcaa acatgtttgc   2460

tgtgttatag ggagaagcac tgctcgatac tctgaacatg gactatcctt acaacgtaag   2520

cttcaagagc ttggcatatt tcctggttgc ccctacatta tgttaccagg tagcagtact   2580

ttcaagtgat ttagttaatt tttggaagca atttcttttt atttgtaatt gttgtggtgt   2640

tgcctcattt agattggcct attttacatt tgcattcatt tttcttgtct tagattgctt   2700

ataggcacaa ccatgtgcag ttgcttaccc atatatcttt ggtgtggact atgtctgagg   2760

tttttagtca gtgtctaatt ggacatgctg ttgggaaccc agaaacagaa tacaagaaaa   2820

gaatgcttct tgtactgaaa aattgaatga caacaaagaa aagaggagaa ttttgctcaa   2880

agggtttctc cacagcagag attctcagtt tacaaatgct aacaaatttg aatgacttcc   2940

cccccccccc cccccccaaa aaaaaaggta taattgctct aactaataat caaactaatt   3000
```

```
gctctaacca tcccaactaa tttccccttc cctctctcct aactccgtaa cagggtgaac   3060
ataattacac tgctaggaat taagttccca tctaaaaggt ataattgatc cagaatgttg   3120
agttggctgt gtgatcactt gattcttaca tagtaggatt tctccgaatg actttaatta   3180
ttgtctattc tattcctttc agcaaatttc tccatttatc atcctgtctt tcctttccat   3240
cttctaattt tggccatttg accttgttca tctcacattc aatactcttt tctatttttt   3300
tggcatgcgc ttagacaaca caacattttg tagcataaaa tattgtgtaa tgaaatctat   3360
agcaggaatc tcccgaacct ttctcatgct ccccctttac ttccattcat acaaaattcc   3420
caatgtacaa ttcctattgc aatctgctag tttctagaca caacctgcta atcaatgcaa   3480
gggggagggg agggggggta gtagccactg ttagtcaatg tgttcttcaa tctgcttata   3540
attctgcttg cttcttgctt ttatatgatt agaagctaag aataagattt taagggaatg   3600
ggtattacat gactccctgg cataaaatgt agcatacatt tctaatgctt tgtgagaata   3660
ctggattggc tttggcatct tcagtgttta cctaagttgc agaaattttg cttgcggttc   3720
tttaagtagg tttctgcagt tcatttgtct ttgccttttc ctgcataaat gtatatccat   3780
gtagattgca tttgttattt ttttcttctg tgagcaaggt tttcacatt tttatttgca    3840
tctattttgt tttatgaact gctcttttag ccaagctatc ctcgcacacc ttatattcga   3900
aagggttggt tgtttcgcca acttgtcaag ctgataatat ttacaggagt tatgggattt   3960
ataatagaac aagtaagcag ttcctgttaa taaattgtgt tcatttctac ttttttttcct  4020
ttcttttttt tttgtgcatt tttttcttca ggtttatttc accaattcta ctggtattct   4080
gacattattt tgattgtaaa attctgcagt atattaatcc catagtacaa aattcacagc   4140
atcctctcaa gggaaacctt ctttacgcca ccgagagagt tctgaagctt tctgttccaa   4200
atttatatgt gtggctctgc atgttctatt gctttttcca cctttggtat tccatctctt   4260
gtttggttca acatgtgtgt gtgcattttt cttataagat attagtctga actatgaagt   4320
taatttcacc tgccataaat tgaatagctg tagttcttgt atcttttgtt taatgccttg   4380
acttttgtac cctggcaatt ttcagatgat gatgatgtta taagtttgta attgattaat   4440
ctttcaaatc atcgttgaaa tgatatccac cttcctaaac accttaaata gtaattacat   4500
catcaatggg aggatctagc taatttaaag gtgtgcatgt agagactatt gttgtctgga   4560
ctctggagta tatacttctt aagatataaa attaacttta tagcctgttt ggtgtgccac   4620
aattgattaa tttaagtgac actctgacag atatacgaag ggattttaga gccttatttt   4680
attgatggat ttgtatattt ttcctgtggc cagtgaggat attttattca tgtatgcttg   4740
atttttctcc tctttaatag aactactatt agaaaaaact agatctcttt gtgcatgcgt   4800
aaatgttgat ctgattgtct catttctaga tattagaaaa tgttcacctt tgttttttta   4860
agatttagtt catatttgag gcagcttatc attggagtga ctgttccaat gtaggttaaa   4920
tatcctggca gagcttcttc gatttggtga tcgtgaattc tacaaggatt ggtggaatgc   4980
caaaactgtc gaagatgcaa gttatttgtc ctgatatttt gttgtttact tacagtattt   5040
tcagtctttc ataaagagaa tttgtgactt attgttttct tgtatttttg ctgttgttgc   5100
tgcttccatc agtattggag gatgtggaat atggtatgtc tctttttcag acttaatttt   5160
gatgaacaaa ttgattttct tgttgtcagc aaaatgattt tctggtttct tgttgggatg   5220
aaattcaagt gaacacacac acacacacat atatttgata taactatccc ttaagtgtat   5280
aatgagggtt gactactctc cgagactatt ttaacaaagg aagaaagaga agttacaaca   5340
```

-continued

```
ttttgccatc ttactgaata aatggtttta aaactgtctt tcagaacata tcattgatta   5400
ttcatcactt aaagttccaa accattagta taatctgagt ggaatctttt acattgcagc   5460
ctgttcacaa atggatgatc cgccacctat attttccatg tttaaggcac ggtctaccaa   5520
aggtaatcaa gcatcctcct gtgttgctga atggatcctg aatttatttg gtctaaactc   5580
taaaacattt ttaggatttg tcagtctctg tttaccatct caggttgcca ctaagatgat   5640
cacatttaac atagttaaat taaaaggaac atgtatgtta gttatatcct aataatcaca   5700
gttatgtaaa aacttatcaa taaacctatt acataagttt ttttttttta aaaagtatgt   5760
atatattttt tttgcactaa ttgtatggtt tgatatgttt gatgcactgg aggaatatgt   5820
agaaagtttg caattggtag acaatagttg aacttcattt ctgttctgtc gtttcagata   5880
aatgactttg gaatgtataa acttgactaa cacaaacaag aactgcaaac gaactccatt   5940
attttttttt cttatgtaat catggttgat atctttgtga tttttttcct tggtctttgc   6000
tatcaacaat ttcctatcaa catagttgtt tctcattggt taatattttg attggctctt   6060
gtttttaaa gcattattgg tattttaatt ttcagttcta gataatgttt tgatttttca   6120
tcattgtaca ggctgctgct cttttaattg ccttcctggt ttctgcttta ttccatgagg   6180
tgtgttgttc atctctctgt acagccttct ctcttccttt tttggtatta tgtcattatg   6240
gttttctgct tgagtatttg tctgcattct acactgatca atgtcaggaa gcatcttgca   6300
atcaatatat ttttggaata ttctttcctt cttttccttg ggctgtttgg actgtgttag   6360
gagttagata gaagggaagg gaaaattatt tacagacggt tagagttgtt aattagtcag   6420
ttacaggatt tggttagata taaatagggg gtattaagag gaaatgatcc attctatttg   6480
ttatcatttg agaattgagc tttgctattt tgaaaggaaa aatcctttgt gagggggaaa   6540
cccttggagg agagttatct ttcctatttt ctgttttaga tgataaaagt gttcttttat   6600
ttctttcttt gctttgggtt cgtaacagac tgtgggagag aactgaaaat tagatactaa   6660
gttgtggctg atttgttaaa aattggtata ggacctacgt tacttgtctt tgaactatct   6720
acaacctcat atggcctcag aaaccttagc cttaggcagc tagttaccaa aatctcaagt   6780
aacttgtagc ctgtctgtac cttggcatgt gtagatgtta cagcttccat atcttaaaat   6840
agattgacat aacaattatg agggactgtc acattttcta gtttccacct gagttcttgc   6900
aatattaact ttggcaccaa aatttcccta catgtactca aggatgcttt ctttagccat   6960
gaataatttt tttcacatgt tgtaattatg ttttcaatta atcctgtcat cttttcctcc   7020
tgaaaaaggt acatacgcag ataagaataa tttgataact taattgtcac agacagttgt   7080
gcaatttttt tcacgatatc tctatcatct gagtgcagct gtgcattgct gttccttgcc   7140
acatattcaa gttgtgggct ttcggtggaa ttatgtttca ggtaaaatca aattaccgta   7200
ttatacttct gttttcccat cttctattat taaactaaag tattttaatt tagagcaaga   7260
gtaacacaaa ttttccaaga aaccaaactt ctcccctctt ccctcacgaa gaaggtgaag   7320
gattgcccag attttgtctt ttcctgttct tttatggcca aatgaaagaa agtattctct   7380
gaagtaatga atctgtgcca tgtttgaagt agttgatgat tatgatatca tccatacttt   7440
tggttcaatt gacatgatca tgaatgcccg gtttttaggt tcctttggtc ttgatcacta   7500
attatctgca aaataaattc agaaactcaa tggtacgtct gctatttaag tatatcagtt   7560
cataaatcat aatgtatctt ataactccca tcatcttgaa tttgattcgt tggtttttta   7620
atgttatttt cttcatgcca ggttggaaat atgatttttt ggttcatatt cagtatcctt   7680
ggtcaaccta tgtgtgtact gctatactac catgacttga tgaataggaa aggcaaactt   7740
```

```
gactgaagct acggccatta cattttaaag gtgcacatgg atgagctttt cagttttcag   7800

attgtaaaat tgatgtggat atgttggtca atatttgttt tctacgaatg ctttcatcta   7860

ccatggcatt ggctgctctg aaggaattcc acgggatatg ccagttcacg aggctaattc   7920

attatcttga tctatgtact taccaactct cctctggcaa ttgtatcaaa atatgcaatt   7980

ttgagagcca tacactggca ttgataactg ccaaggaaca ctctaactgt tttctgttaa   8040

ctgttaatta gtagagggct agatgtaaat ggtttatgct caatatattt atttcctcct   8100

agtcttcaag ttccacggat gaatgatgtc tttatagcag ttttttcttt ctacaaaact   8160

tgcatatcac tttaaaggta ttgtttgtgt tgtttttgct gatcataatt gaagttt      8217
```

<210> SEQ ID NO 30
<211> LENGTH: 8243
<212> TYPE: DNA
<213> ORGANISM: Glycine max

<400> SEQUENCE: 30

```
tagaaatctg ttgtttattt tttggtgaag agaagactga gttagtaaac acgctcgctc     60

ggtcttcttt tccaatggcg atttccgatg agcctgaaac tgtagccact gctctcaacc    120

actcttccct gcgccgccgt cccaccgccg ctggcctctt caattcgccc gagacgacca    180

ccgacagttc cggtgatgac ttggccaagg attccggttc cgacgactcc atcagcagcg    240

acgccgccaa ttcgcaaccg caacaaaaac aagacactga tttctccgtc ctcaaattcg    300

cctaccgtcc ttccgtcccc gctcatcgca aagtgaagga aagtccgctc agctccgaca    360

ccattttccg tcaggttctc gccgttaact tctactttac aattattaca attccgtaac    420

tatttcaaac tcaaccagaa cggtaccgtt tcgttcccgt tctgcattaa taaactactc    480

aatctcaatg catgactcat gaatgcaagc gactcgtagt cttttaggtg cttaaaatag    540

tgtatgctac tgctagttag ttaatttgtg tgtacgggaa actagttatc aatttatgat    600

ttgaatttaa tacaattgaa ttggtggatc aggtttttgt acctgctatt gtgtttggtt    660

tataattagg tgtgatgagt ctgatatgta attatatttc tttactaatt attcaatcag    720

ttgcagagtc acgcgggcct cttcaacctc tgtatagtag tccttgttgc tgtgaatagc    780

cgactcatca ttgagaattt aatgaaggtt ttgcctcttc catgtttaat tgtgcattca    840

cctgcaacaa ttttctgttc tttttattta tgaccttgat tttgacggtt cgggttttgt    900

tgtctgcttt aatgagtgtt ttatttgttc tgcagtatgg ttggttgatc aaatctggct    960

tttggtttag ctcaaagtca ttgagagact ggcccctctt catgtgttgg taatgagtgt   1020

aatgaattcc ctaaagaatt aactatgtac tatgtaatta ttctgaaatg ttgttcaaca   1080

gtatgtggtt gtgcacttgg tttgcagtct ttctcttgtg gtatttcctt ttgctgcatt   1140

tatagtggag aagttggcac agcagaagtg tatacccgaa ccagttaagt gatcaggcca   1200

tatgagcttt tattagattt cattcgtttt ataacctaaa atatttttgg gatatggtta   1260

gttgtgatgt gctattctta actgttcaat ctttaatatt tgcatacatg agaatattat   1320

attactttaa tattgcaggt tgttgttgta cttcatataa tcattacctc agcttcactt   1380

ttctatccag ttttagtaat tctcaggtca gttaagttct tttgtatata ttctggggct   1440

gcagttgagg caccttttgt tttgacatgg gtggttacac aatgtgtcca ttttgaaaga   1500

atttggtaat agaatatggt tttaagttga tagtggtgtt aagtaacaaa ctttgtcact   1560

atcctgcaca ggaatttaaa ttttttttatt atattttaaa attacttgag aagaaattta   1620
```

```
aagcatttgg gtgaacctta gtttaatgtt tggttcttat catgttggaa ttgaattatg   1680
ttgcaaaata tgaagatgaa tgctgaggga tgaaataatt atacagttgt gcattcttag   1740
tcatttcata gataaggata tcccagaaag atgattactg acttgtaaca ttctttgcag   1800
gtgtgattct gcttttctat caggtgttac gttaatgcta tttgcttgtg ttgtatggtt   1860
aaaattggtg tcttatgcac atacaaacta tgatatgaga gcacttacca aatcagttga   1920
aaaggtaata aatactctct gtttaaacgg agagaaaatt ttgaattttt ttttcttaaa   1980
agtcaacttt tctctcttgt ctttaactaa acaaaagaaa atctatcttt acgtgttttt   2040
tctttcatct aattttttcc ttaaccaaac atattcttaa attctacttg gcacttgtaa   2100
gtgggtagat aactatcaca aaatatcatc gtcacttatt tgtatacttt aaagatgacc   2160
atatgttgta caatgtttgt gatgattagt ttttgaacct gaacatcctg cttgacttag   2220
cagtagctta tggatcatgt actcttaaaa cttcattata tgctgaagta cagttttatt   2280
tcatcttcat ttgaattact tccatcctgt gttccgcttt attgcttcct tctatctaga   2340
tggttagctc ttcaaacgtg tgaatgtgtg atagataaac catctgcttt ccctccttat   2400
tcaaacatgt ttcatgtgtt atagggagaa gctctgcccg atactctgaa catggactat   2460
ccttacaatg taagcttcaa gagcttagca tatttcctgg ttgcccctac attatgttac   2520
caggtagcag tactttcaag tgatttagtt aatttttgga agcaattttt tttaattgtt   2580
gtggtgttgc ctcatttaga ttcgcctatt ttacatttgc attcactttt ctagtcttag   2640
attgcttata ggcacaacca tgtggagttg cttactcata tatctttggt gtggaatatg   2700
tctgaggttt ttagtcagtg tctaattgga catgctgttg ggaacccaga aacagagtat   2760
gagaaaagaa tgcttcttgt actaattaca gaatattgaa tgacaacaaa gaaaagggga   2820
aaattttgct caaagagttt ctcctttcac aacacagatg cttaattgaa tgactccccc   2880
ccccaaaaaa aaaaaaaaat cttcctatat gtttctcact aaccccctct aactaagaat   2940
caaactaatt gctctaacca tcccaactaa tttcactgct aggaattaag ttcccatcta   3000
acaagtataa ttgatccaga atgttgggtt ggctacatag taggatttct ctgaatgact   3060
ctttaatcat tgtcttcaat acattctata cctttcagca aatttctcca tttattatcc   3120
tttctttcct ttccatcttc taattttggc catttgacct cgttcatctc acattcaata   3180
ctcctttcta ttttgtagca tagaatattg tgtaatgaaa tctatagcag gaatccccca   3240
aacccttctc atgccccccc tttacttcct tcgtacaaaa ttcccattgc aatctgctag   3300
tttctagaca caacctgcta gtcaatgcac ggtgtaggag ccacaatctg ttagtctatg   3360
tgttcctcaa tctgcatata atacttcttg cttcttgctt ttatatgaag ctaagaataa   3420
gattttaagg gaatgagtat tacatgactc cccggcataa aatgtagcat gcatttctaa   3480
tgctttgtga gaatactgga ttggctttgg catcttcagt gtttacctac gttgcagaaa   3540
ttttgcttgg ggttctttaa gtaggtttct gcagttcatt tgtctttgca ttttcctgca   3600
taaatgtatc tccatgtgaa ttgcatttgt tattttttt attctgagag caaggtcttt   3660
cacattttta tttgcatgta ttttgtttta tgaactgctc ttttagccaa gctatcctcg   3720
cacaccttat attcgaaagg gttggctgtt tcgccaactt gtcaagctga taatatttac   3780
aggagttatg ggatttataa tagaacaagt aagcagttcc tgttaataaa ttgtgttcat   3840
ttctaccttt ttttcatttc ttttttatg tacattttt tcttgaggtc tatttcacca   3900
attctactgg tattctgaca ttattttgac tgtaattttg cagtacatta atcccattgt   3960
acaaaattca cagcatcctc tcaagggaaa ccttctttac gccatcgaga gagttctgaa   4020
```

```
gctttctgtt ccaaatttat atgtgtggct ctgcatgttc tattgctttt tccacctttg   4080
gtattccatc tcttgtttgg ttcaacatgt gtgtatgtgt gtgcattttc cttacaagat   4140
attagtatga agttatcttc acctgccata aattgaataa ttatagttct agtttatttt   4200
gtttgatgcc ttgacttttg taccctggca attttctgat gatgatgatg ttataagtta   4260
gtaattgatt aatctttcaa atcatccttg aagtgatatc caccttccta aacaccttaa   4320
aatagtaatt acatcatcaa tgggaagatc tagctgatct aaaggtgtgc atgtagagac   4380
tattggtgtc ttgagtgtac acttctaaag atataaaata aactttatag cctgtttggt   4440
gtgccaccaa tgattaattt aagtgacact ctgacggata tgtgaaagga tttgagagcc   4500
ttattttatt gatggatttg aatatttttc ctttggccag tgaggatata ttattcttca   4560
tttatgctct tttttctcct ctttaagaac tactcttaga aaaaaaacta gatctttttt   4620
tgcaagcata aatgctgatc tgcttgtctc atttgtagat attagaaaag gttcaccttt   4680
gattttttaa gatttagtta atatttgagg aagcttatca ttggagtgac tgtcgtaatg   4740
taggttaaat atattggcag agcttcttcg atttggtgat cgtgaattct accaggattg   4800
gtggaatgcc aaaactgttg aagatgtaag ttatttgtcc tgatattttg tcgtttactt   4860
acagtatttt cagtcttcat aaagagaaat tgtgactttt tgtttttgtt tctgtatttg   4920
tgctgttgtt gctgcttcca tcagtattgg aggatgtgga atatggtatg tctctttttc   4980
agacttaatt ttgatgaaca aattgatttt cttgtgttca gcaaaatgat tttcaggtct   5040
cctgttggga tgaaattcat gtgaacacac gtacatatat ttgatataac tatcccttta   5100
aatgtataat gagggttgac aactctccaa gactatttta acaacggaag aaagagaagt   5160
tacaactttt ttccatctta ctgactaaat ggttttaaaa ctgtctttca gaacatatca   5220
ttaattattt atcacgtaaa gttccaaacc attagtataa tctgagcgga atcttttaca   5280
ttgcagcctg ttcacaaatg gatgatccgc cacctatatt ttccatgttt aaggcacggt   5340
ataccaaagg taatcaagca tccttctgcg ttgctgaatg gatcctgaac ttatttggta   5400
ctgtaaaaca tttttaggat ttgtcagcct ctgtttacca tctcgggttg ctactaagat   5460
catcacattt aacatagttg aattaaaatg aacatgttac ttttatccta ataatcacac   5520
ttatgtaaaa acttatcaat aaacctatta cataagtttt ttttcaaaaa ataagtattt   5580
gcactaattg tatggtttga tatgtttggt gcactggggg agctatatgt agaaagtttg   5640
caattggtag acagtaattt agcttcatct tctgttctgt catttcagat aaattacttt   5700
ggagtgcata aacatgacta aaacaagaat tgcaaaggaa ctccattaaa aaaaaaaaaa   5760
atcttatgta atcatgttca atagctttgt gatttttttc cttggtcttt gccatcaaca   5820
atttcctatt aacatatagt tgtttctcat tggttaatat ttggattggc tctttttttg   5880
tcaagcatta ttggtatttc aatttttagt tctagataaa atttttattt ttcatcattg   5940
tacaggccgt tgctctttta attgccttcc tggtttctgc tttattccat gaggtgtgtt   6000
gctcatctct ctgtacagcc ttctctcttc tttttttggt attatgtcat tatggttgtt   6060
ctgcttgagt gtttgtctgc atcctacact gattgaagtc aaactgtatc ttgcaattaa   6120
tatatttttg gagtatcctt tcctcctttt ccttgggctg tttggacttt gctaagagtt   6180
agatagaagg gaagggaaaa ttagttacag atggttagag tagttgatta gtcagttata   6240
ggatttggtt agatattaat tacggggatt aagaggaaag gatccattct atctagttga   6300
ttagtcagtt ataggatcca ttctatctag tatcatttga gaattgagct tggctctttt   6360
```

```
gaaaggagaa atcctttgtg agggggaaac ccttggagga gaattatctc ttcttttttc   6420
tgttctagat gataaaactg cccttttatt tctttctttg ctttgggttc gtaacagact   6480
gtgggagagg actgaaaatt agatactaag ttgtggctga tttgttaaaa attggtatag   6540
gacccatgct acttgtcttt gaactatcta caacccacta tggccccaga aaccttaggc   6600
agctagctac caaaatctgt agtaacttgc agcctgtctg tctgtacctt ggcaggtgta   6660
gatgttacag cttccatatc ttatatctta aatatagact gacataacaa ttatgacaaa   6720
ctgttatatt ttctagttgc tagttcttgc aatattaatt ttggcaccaa aatttcccta   6780
catgtactca aggatgctta ctttagccat gaataatttt tttttcacg tgttgtaatt    6840
atattttcaa tttatcctgt catttttcc tgaaaaaggt acatacacag aataatttga    6900
taacttaagg tggcgcttgg tttgagtgtt ttgtgttttc attttcaaag aaaatagaaa   6960
ataagagtga aaatatgttt gcctaaaatt tagaaaacat tttctatgaa aatatttcaa   7020
aaacaagccc aaaactgaaa acaaccaata aactttttca gcctttttct gaagaagtga   7080
aaacacgatg tcactttaga gtactttctt ctcaaaacac gttttctaaa tcttgaaaat   7140
ctgaaaatga aaataaaaat tattttgaga aaatgaaaac agaaaataaa cattcaaatc   7200
aaacgccacc ttaattgtca tagacagttg tgcaattttt ctcacgatat ctctttcgtc   7260
tgagtgcagc tgtgcatcgc tgttccttgc cacatattca agttgtgggc tttcggtgga   7320
attatgtttc aggtaaaatc aaattaccgc actaaacttt tgttttccca tcttctatta   7380
ttaaactaaa gcattttaat tcagagtaag agtaacacga attttccaag aaaccaaact   7440
tctcccctct tccctcacga agaaggtgaa ggattgccga gattttttt tcctgttctt    7500
ttatggccaa acgatagaaa gtattctctg gaataatgaa tttgtgccat gtttgaaagt   7560
tgatgattat gatatcatcc atctttttgg ttcaattaac atgataagga atgacttttt   7620
tctaggttcc tttggtcttc atcactaatt atctgcaaaa taaattcaga aactcgatgg   7680
tacgtctgct atttaagcat attgattcat aatatatctt attactccat catcttgaat   7740
ttgattcatt ggttttttaa tttgtttttg tcttcatgcc aggttggaaa tatgattttt   7800
tggttcatat tcagtattct tggtcaacct atgtgcgtac tgctatatta ccatgactta   7860
atgaatagga aaggcaaact tgactgaagg tgcacgtgga taagcttttc tgtttttgga   7920
gtgtataatt gatgtcgata tgttgatcaa tattgttttc cacgagtact ttcatctacc   7980
atggcagtgg ctgctctgaa ggatttccac ctgatatacc aggtcgcgag gctaattcat   8040
cttgatctat gtacttatca actctcctct ggcaattgta tcgatatatg caattttgag   8100
agccatacac tggcattgat aactgccaag gaacagtgta gctgttttct gttaaatgtt   8160
aattagtaga gagctagatg taaataattt atgctcaata tatttatttc ttcctattct   8220
tcaagttcca cggatgaatg atg                                           8243
```

```
<210> SEQ ID NO 31
<211> LENGTH: 20
<212> TYPE: DNA
<213> ORGANISM: Artificial Sequence
<220> FEATURE:
<223> OTHER INFORMATION: GM-DGAT-CR1 (synthesized almost complement of
      native sequence)

<400> SEQUENCE: 31

ggaattgaag aggccagcgg                                                 20


<210> SEQ ID NO 32
```

```
<211> LENGTH: 20
<212> TYPE: DNA
<213> ORGANISM: Artificial Sequence
<220> FEATURE:
<223> OTHER INFORMATION: GM-DGAT-CR3 (synthesized almost complement of
      native sequence)

<400> SEQUENCE: 32

gcggcggtgg aggtggcgga                                                   20


<210> SEQ ID NO 33
<211> LENGTH: 20
<212> TYPE: DNA
<213> ORGANISM: Artificial Sequence
<220> FEATURE:
<223> OTHER INFORMATION: GM-DGAT-CR4 (synthesized almost complement of
      native sequence)

<400> SEQUENCE: 33

ggacagttcc ggtgatgact                                                   20


<210> SEQ ID NO 34
<211> LENGTH: 25
<212> TYPE: DNA
<213> ORGANISM: Artificial Sequence
<220> FEATURE:
<223> OTHER INFORMATION: DGAT1a primer

<400> SEQUENCE: 34

agactgagtt agtaaacacg ctcgc                                             25


<210> SEQ ID NO 35
<211> LENGTH: 25
<212> TYPE: DNA
<213> ORGANISM: Artificial Sequence
<220> FEATURE:
<223> OTHER INFORMATION: DGAT1a primer

<400> SEQUENCE: 35

tacgagtcgc ttgcattcat gagtc                                             25


<210> SEQ ID NO 36
<211> LENGTH: 25
<212> TYPE: DNA
<213> ORGANISM: Artificial Sequence
<220> FEATURE:
<223> OTHER INFORMATION: DGAT1b primer

<400> SEQUENCE: 36

agactgagtt agaaaacacg ctcgg                                             25


<210> SEQ ID NO 37
<211> LENGTH: 30
<212> TYPE: DNA
<213> ORGANISM: Artificial Sequence
<220> FEATURE:
<223> OTHER INFORMATION: DGAT1b primer

<400> SEQUENCE: 37

tttctagtac acataaatta aataaacaag                                        30


<210> SEQ ID NO 38
<211> LENGTH: 7
<212> TYPE: PRT
<213> ORGANISM: Artificial Sequence
<220> FEATURE:
<223> OTHER INFORMATION: Glycine max derived peptide
```

<400> SEQUENCE: 38

```
Ala Pro Thr Leu Cys Tyr Gln
1               5
```

<210> SEQ ID NO 39
<211> LENGTH: 13
<212> TYPE: PRT
<213> ORGANISM: Artificial Sequence
<220> FEATURE:
<223> OTHER INFORMATION: Glycine max derived peptide
<220> FEATURE:
<221> NAME/KEY: misc_feature
<222> LOCATION: (8)..(8)
<223> OTHER INFORMATION: Xaa is any amino acid

<400> SEQUENCE: 39

```
Phe Gly Asp Arg Glu Phe Tyr Xaa Asp Trp Trp Asn Ala
1               5                   10
```

<210> SEQ ID NO 40
<211> LENGTH: 6
<212> TYPE: PRT
<213> ORGANISM: Artificial Sequence
<220> FEATURE:
<223> OTHER INFORMATION: Glycine max derived peptide

<400> SEQUENCE: 40

```
Leu Leu Tyr Tyr His Asp
1               5
```

<210> SEQ ID NO 41
<211> LENGTH: 44
<212> TYPE: PRT
<213> ORGANISM: Artificial Sequence
<220> FEATURE:
<223> OTHER INFORMATION: Glycine max derived peptide
<220> FEATURE:
<221> NAME/KEY: misc_feature
<222> LOCATION: (8)..(8)
<223> OTHER INFORMATION: Xaa is any amino acid
<220> FEATURE:
<221> NAME/KEY: misc_feature
<222> LOCATION: (11)..(11)
<223> OTHER INFORMATION: Xaa is any amino acid
<220> FEATURE:
<221> NAME/KEY: misc_feature
<222> LOCATION: (18)..(18)
<223> OTHER INFORMATION: Xaa is any amino acid
<220> FEATURE:
<221> NAME/KEY: misc_feature
<222> LOCATION: (22)..(22)
<223> OTHER INFORMATION: Xaa is any amino acid
<220> FEATURE:
<221> NAME/KEY: misc_feature
<222> LOCATION: (26)..(26)
<223> OTHER INFORMATION: Xaa is any amino acid
<220> FEATURE:
<221> NAME/KEY: misc_feature
<222> LOCATION: (30)..(30)
<223> OTHER INFORMATION: Xaa is any amino acid
<220> FEATURE:
<221> NAME/KEY: misc_feature
<222> LOCATION: (42)..(42)
<223> OTHER INFORMATION: Xaa is any amino acid

<400> SEQUENCE: 41

```
Glu Ser Pro Leu Ser Ser Asp Xaa Ile Phe Xaa Gln Ser His Ala Gly
1               5                   10                  15

Leu Xaa Asn Leu Cys Xaa Val Val Leu Xaa Ala Val Asn Xaa Arg Leu
            20                  25                  30
```

```
Ile Ile Glu Asn Leu Met Lys Tyr Gly Xaa Leu Ile
        35                  40


<210> SEQ ID NO 42
<211> LENGTH: 19
<212> TYPE: PRT
<213> ORGANISM: Artificial Sequence
<220> FEATURE:
<223> OTHER INFORMATION: Glycine max derived peptide
<220> FEATURE:
<221> NAME/KEY: misc_feature
<222> LOCATION: (13)..(13)
<223> OTHER INFORMATION: Xaa is any amino acid
<220> FEATURE:
<221> NAME/KEY: misc_feature
<222> LOCATION: (16)..(16)
<223> OTHER INFORMATION: Xaa is any amino acid

<400> SEQUENCE: 42

Gly Phe Ile Ile Glu Gln Tyr Ile Asn Pro Ile Val Xaa Asn Ser Xaa
1               5                   10                  15

His Pro Leu
```